United States Patent
Starck et al.

(10) Patent No.: US 11,833,162 B2
(45) Date of Patent: Dec. 5, 2023

(54) MACROCYCLIC DERIVATIVES, PROCESS FOR PREPARING SAME AND PHARMACEUTICAL COMPOSITIONS CONTAINING SAME

(71) Applicants: LES LABORATOIRES SERVIER, Suresnes (FR); VERNALIS (R&D) LTD, Cambridge (GB)

(72) Inventors: Jérôme-Benoît Starck, Rueil-Malmaison (FR); Didier Durand, Chambourcy (FR); I-Jen Chen, Cambridge (GB); Arnaud Le Tiran, Croissy sur Seine (FR); Jean-Claude Ortuno, Bois D'arcy (FR); Miklós Nyerges, Leányfalu (HU); Melinda Ligeti, Budapest (HU); Imre Fejes, Budapest (HU)

(73) Assignees: LES LABORATOIRES SERVIER, Suresnes (FR); VERNALIS (R&D) LTD, Cambridge (GB)

(*) Notice: Subject to any disclaimer, the term of this patent is extended or adjusted under 35 U.S.C. 154(b) by 0 days.

(21) Appl. No.: 16/757,052

(22) PCT Filed: Oct. 24, 2018

(86) PCT No.: PCT/EP2018/079113
§ 371 (c)(1),
(2) Date: Apr. 17, 2020

(87) PCT Pub. No.: WO2019/081559
PCT Pub. Date: May 2, 2019

(65) Prior Publication Data
US 2020/0253993 A1    Aug. 13, 2020

(30) Foreign Application Priority Data
Oct. 25, 2017    (FR) .................................... 1760078

(51) Int. Cl.
| | | |
|---|---|---|
| *C07D 498/18* | (2006.01) |
| *A61K 31/675* | (2006.01) |
| *A61P 35/02* | (2006.01) |
| *A61K 31/4748* | (2006.01) |
| *A61K 31/5377* | (2006.01) |
| *A61K 45/06* | (2006.01) |
| *C07D 498/22* | (2006.01) |
| *C07F 9/6533* | (2006.01) |

(52) U.S. Cl.
CPC ........ *A61K 31/675* (2013.01); *A61K 31/4748* (2013.01); *A61K 31/5377* (2013.01); *A61K 45/06* (2013.01); *A61P 35/02* (2018.01); *C07D 498/18* (2013.01); *C07D 498/22* (2013.01); *C07F 9/65335* (2013.01)

(58) Field of Classification Search
CPC ............................ A61K 31/675; C07D 498/18
See application file for complete search history.

(56) References Cited

FOREIGN PATENT DOCUMENTS

| WO | WO2014022752 | 2/2014 |
|---|---|---|
| WO | WO2015011397 | 1/2015 |

OTHER PUBLICATIONS

McMahon et al. (2000).*
Pinedo et al. (2000).*
Cancer Drug Design and Discovery Neidle, Stephen, ed. (Elsevier/Academic Press, 2008) pp. 427-431.*
International Search Report for PCT/EP2018/079113 dated Jan. 14, 2019.
Azmi, et al., Tumor Biology 2000, 21, 3-10.
Barassa, et al., Biochimica et Biophysica Acta, 2012, 1823, 2201-2209.
Bray, et al., Mol. Cancer Res., 2009, 7(9), 1487-1496.
Catz, et al., Apoptosis, 2003, 8, 29-37.
Chen. et al., Biochemical Pharmacology, 2012, 84, 268-277.
Cooke, BJU International, 2000, 85, 829-835.
Deng, et al., Cancer Cell, 2007, 12, 171-185.
Fassl, et al., Oncogene, 2012, 31, 4698-4708.
Goldsmith, et al., Cancer Research, 2012, 72(10), 2565-2577.
Hanada, et al., Blood, 1993, 82, 1820-1828.
Hanahan and Weinberg, Cell, 2011, 144, 646-674.
Jiang, et al., Journal of Pathology, 1995, 177, 135-138.
Juin, et al., Nature Reviews Cancer, 2013, 13, 455-465.
Kelly, et al., Cell Death and Differentiation, 2011, 18, 1414-1424.
Kirkin, et al., Biochimica et Biophysica Acta, 2004, 1644, 229-249.
Lestini, et al., Cancer Biol. Ther., 2009, 8(16), 1587-1595.
Letai, et al., Blood, 2005, 106, 5008.
Liu, et al., Blood, 2003, 101(10), 4105-4114.

(Continued)

*Primary Examiner* — Paul V Ward
(74) *Attorney, Agent, or Firm* — HUESCHEN AND SAGE

(57) ABSTRACT

Compound of formula (I):

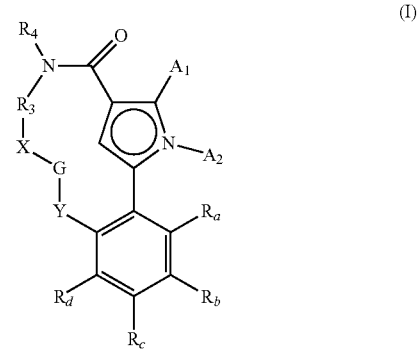

wherein $A_1$, $A_2$, $R_a$, $R_b$, $R_c$, $R_d$, $R_3$, $R_4$, X, Y and G are as defined in the description,
and their use in the manufacture of medicaments.

15 Claims, No Drawings
Specification includes a Sequence Listing.

(56) References Cited

OTHER PUBLICATIONS

Maamer-Azzabi, et al., Cell Death and Disease, 2013, 4, e801.
Mano, et al., European Journal of Cancer, 1999, 35, 1214-1219.
Miyake, British Journal of Cancer, 1999, 79(11/12), 1651-1656.
Monni, et al., Blood, 1997. 90, 1168-1174.
Sarbia, et al., American Journal of Pathology, 1999, 155(4), 1027-1032.
Slavov, et al.. Proc. Natl. Acad. Sci. USA, 2009, 106, 4079-4084.
Tsujimoto, et al., Science, 1985, 22B, 1440-1443.
Valiant. et al., Cancer Cell, 2013, 24, 120-129.
Vaux, et al., Nature, 1988, 335, 440-442.
Witham, et al., Clin. Cancer Res., 2007, 13(23), 7191-7198.
Yip, et al., Oncogene, 2008. 27, 6398-6406.
Zhao, et al., Plos One, 2011, 6(8), e21980.

\* cited by examiner

MACROCYCLIC DERIVATIVES, PROCESS FOR PREPARING SAME AND PHARMACEUTICAL COMPOSITIONS CONTAINING SAME

The present invention relates to new macrocyclic compounds, to a process for their preparation, and to pharmaceutical compositions containing them.

The compounds, of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer, 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in auto-immune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colorectal cancer, breast cancer, small-cell lung cancer, non-small-cell lung cancer, bladder cancer, ovarian cancer, prostate cancer, chronic lymphoid leukaemia, follicular lymphoma, myeloma, etc. Overexpression of the anti-apoptotic proteins of the Bcl-2 family is involved in tumorigenesis, in resistance to chemotherapy and in the clinical prognosis of patients affected by cancer. There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer, auto-immune diseases and diseases of the immune system.

The invention relates in the first embodiment (E1) to the compounds of formula (I):

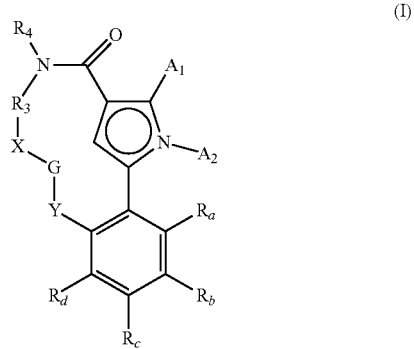

wherein:
$A_1$ and $A_2$ independently of one another represent a hydrogen or halogen atom, a linear or branched polyhalo-$(C_1$-$C_6)$alkyl, a linear or branched $(C_1$-$C_6)$alkyl group or a cycloalkyl group,
or $A_1$ and $A_2$ form together with the atoms carrying them an aromatic or non-aromatic heterocycle Het composed of 5, 6 or 7 ring members, which may contain, in addition to nitrogen, from one to 3 hetero atoms selected independently from oxygen, sulphur and nitrogen, it being understood that the nitrogen in question may be substituted by a group representing a hydrogen atom, a linear or branched $(C_1$-$C_6)$alkyl group or a group —C(O)—O-Alk wherein Alk is a linear or branched $(C_1$-$C_6)$alkyl group,
G represents a group —$NR_7$—, a group 1,2,3,4-tetrahydroisoquinolinylene optionally substituted by a group T, a group 2,3-dihydro-1H-isoindolylene optionally substituted by a group T, or a piperidinylene group.
T represents a hydrogen atom, a linear or branched $(C_1$-$C_6)$alkyl optionally substituted by from one to three halogen atoms, a $(C_1$-$C_4)$alkyl-$NR_1R_2$ group, or a $(C_1$-$C_4)$alkyl-$OR_6$ group,
X represents a $(C_2$-$C_8)$alkylene group in which from 1 to 3 ring members may be replaced by a hetero atom selected from oxygen, sulphur and N—$R_5$, or by an arylene or heteroarylene group,
Y represents a group —$CH_2$— or —CO—,
$R_1$ and $R_2$ independently of one another represent a hydrogen atom or a linear or branched $(C_1$-$C_6)$alkyl group,
or $R_1$ and $R_2$ form with the nitrogen atom carrying them a heterocycloalkyl,
$R_3$ and $R_4$ are such that:
one of them represents a phenyl group of the following formula

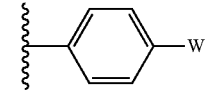

wherein W represents a hydroxy group or a phosphate group selected from —OPO(OM (OM'), —OPO(OM)(O$^-M_1^+$), —OPO(O$^-M_1^+$)(O$^-M_2^+$), —OPO(O$^-$)(O$^-$)$M_3^{2+}$, —OPO(OM)(O[$CH_2CH_2O$]$_n$$CH_3$) and —OPO(O$^-M_1^+$)(O[$CH_2CH_2O$]$_n$$CH_3$), wherein M and M' independently of one another represent a hydrogen atom, a linear or branched $(C_1$-$C_6)$alkyl group, a linear or branched $(C_2$-$C_6)$alkenyl group, a linear or branched $(C_2$-$C_6)$alkynyl group, a cycloalkyl or a heterocycloalkyl, both composed of from 5 to 6 ring members, while $M_1^+$ and $M_2^+$ independently of one another represent a pharmaceutically acceptable monovalent cation, $M_3^{2+}$ represents a pharmaceutically acceptable divalent cation and n is an integer from 1 to 5.
while the other represents an aryl, heteroaryl, heterocycloalkyl, cycloalkyl or linear or branched $(C_1$-$C_6)$alkyl group, it being understood that one or more carbon atoms of the preceding groups, or of their possible substituents, may be deuterated,
$R_5$ represents a hydrogen atom or a linear or branched $(C_1$-$C_6)$alkyl group,
$R_6$ and $R_7$ independently of one another represent a hydrogen atom or a linear or branched $(C_1$-$C_6)$alkyl group, $R_a$, $R_b$, $R_c$ and $R_d$ independently of one another represent a hydrogen atom, a linear or branched ($C_1$-$C_6$)alkyl group, a halogen atom, a linear or branched ($C_1$-$C_6$) alkoxy group, a hydroxy group, a linear or branched polyhalo-($C_1$-$C_6$)alkyl group, a trifluoromethoxy group, or the substituents of one of the pairs ($R_a$,$R_b$), ($R_b$,$R_c$) or ($R_c$,$R_d$) form together with the carbon atoms carrying them a ring composed of from 5 to 7 ring members, which may contain from one to 2 hetero atoms selected from oxygen and sulphur, it also being understood that one or more carbon atoms of the ring defined hereinbefore may be deuterated or substituted by from one to 3 groups selected from halogen and linear or branched ($C_1$-$C_6$)alkyl, it being understood that:
- "aryl" means a phenyl, naphthyl, biphenyl or indenyl group,
- "heteroaryl" means any mono- or bi-cyclic group composed of from 5 to 10 ring members, having at least one aromatic moiety and containing from 1 to 4 hetero atoms selected from oxygen, sulphur, nitrogen and quaternary nitrogen.
- "cycloalkyl" means any mono- or bi-cyclic, non-aromatic, carbocyclic group containing from 3 to 10 ring members,
- "heterocycloalkyl" means any mono- or bi-cyclic, fused or spiro, non-aromatic group composed of from 3 to 10 ring members, which may contain from 1 to 3 hetero atoms selected from oxygen, sulphur, SO, $SO_2$ and nitrogen,
- arylene, heteroarylene, 1,2,3,4-tetrahydroisoquinolinylene, 2,3-dihydro-1H-isoindolylene or piperidinylene mean a divalent aryl, heteroaryl, 1,2,3,4-tetrahydroisoquinoline or piperidine group, it being possible for the aryl, heteroaryl, cycloalkyl and heterocycloalkyl groups so defined and the groups alkyl, alkenyl, alkynyl and alkoxy to be substituted by from 1 to 3 groups selected from: linear or branched ($C_1$-$C_6$)alkyl optionally substituted by a hydroxy, morpholinyl, 3,3-difluoropiperidinyl or 3,3-difluoropyrrolidinyl group; ($C_3$-$C_6$) spiro; linear or branched ($C_1$-$C_6$)alkoxy optionally substituted by a morpholinyl group; ($C_1$-$C_6$)alkyl-S—; hydroxy; oxo; N-oxide; nitro, cyano; —COOR'; —OCOR'; NR'R"; linear or branched polyhalo-($C_1$-$C_6$)alkyl; trifluoromethoxy; ($C_1$-$C_6$)alkylsulphonyl; halogen; aryl optionally substituted by one or more halogen atoms; heteroaryl; aryloxy; arylthio; cycloalkyl; heterocycloalkyl optionally substituted by one or more halogen atoms or linear or branched ($C_1$-$C_6$)alkyl groups; it being understood that R' and R" independently of one another represent a hydrogen atom or a linear or branched ($C_1$-$C_6$)alkyl group optionally substituted by a methoxy group, their enantiomers and diastereoisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned, without implying any limitation, sodium hydroxide, potassium hydroxide, triethylamine, tert-butylamine, etc.

Different specific embodiments of the invention (E) are detailed hereinbelow. It should be noted that the features of the different embodiments may be combined with one another to produce new embodiments:

E2. Compound of formula (I) according to embodiment E1 wherein $A_1$ and $A_2$ each represent a methyl group, or one of the groups $A_1$ or $A_2$ represents methyl while the other represents a hydrogen atom.

E3. Compound of formula (I) according to embodiment E1 wherein $A_1$ and $A_2$ form together with the atoms carrying them a heterocycle composed of 6 ring members.

E4 Compound of formula (I) according to one of embodiments E1 to E3 wherein $R_a$, $R_c$ and $R_d$ each represent a hydrogen atom and $R_b$ represents a hydrogen or halogen atom.

E5. Compound of formula (I) according to one of embodiments E1 to E4 wherein Y represents a group —CO—.

E6. Compound of formula (I) according to one of embodiments E1 to E5 wherein G represents a group selected from the following groups:

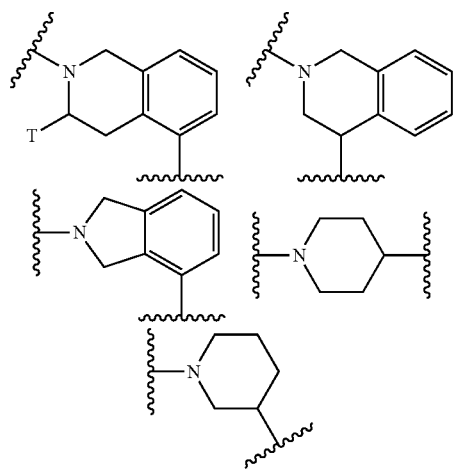

wherein T represents a methyl group or a (4-morpholinyl) methyl group.

E7. Compound of formula (I) according to one of embodiments E1 to E6 wherein X represents a group selected from the following groups:

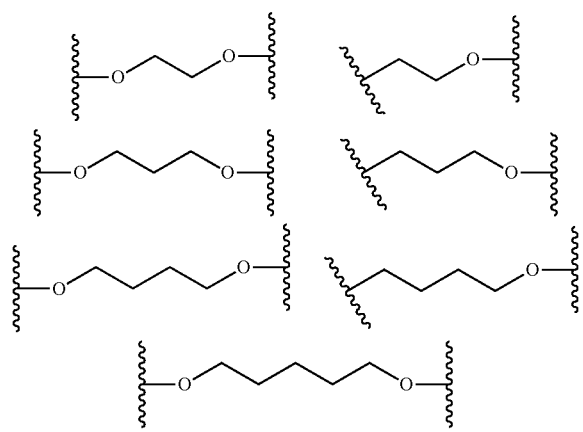

-continued

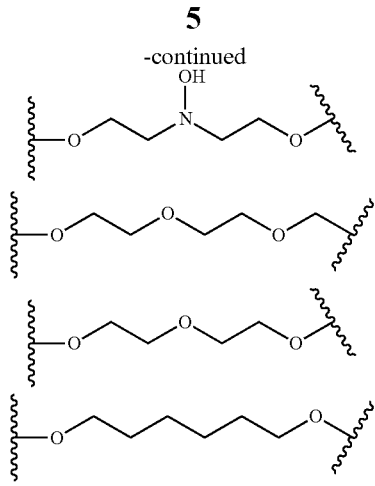

E8. Compound of formula (I) according to one of embodiments E1 to E7 wherein one of the groups $R_3$ or $R_4$ represents a 4-hydroxyphenyl group while the other represents an aryl, heteroaryl or linear or branched ($C_1$-$C_6$)alkyl group.

E9. Compound of formula (I) according to embodiment E8 wherein one of the groups $R_3$ or $R_4$ represents a 4-hydroxyphenyl group while the other represents a group selected from the following list:
a phenyl group optionally substituted by a cyano group,
a pyrazolyl group,
a 1-methyl-1H-pyrazolyl group,
a 1-(tetrahydrofuran-3-yl)-1H-pyrazolyl group,
a 5-methyl-2-cyano-1H-pyrrolyl group,
a 1-methyl-2-cyano-1H-pyrrolyl group,
a 1,2-dimethyl-1H-pyrrolyl group,
a 1,5-dimethyl-2-cyano-1H-pyrrolyl group,
a pyrimidinyl group,
an ethyl group,
a pyridinium group.

In some embodiments of the invention, $R_3$ or $R_4$ represents a group 4-[(NaO)$_2$OPO]phenyl.

E10. Compound of formula (I) according to embodiment E9 wherein $R_4$ represents a 4-hydroxyphenyl group.

E11. Compound of formula (I) according to embodiment E9 wherein $R_3$ represents a 4-hydroxyphenyl group.

E12 Compound of formula (I) according to embodiment E11 wherein $R_3$ represents a 4-hydroxyphenyl group and G represents a piperidinylene group.

E13. Compound of formula (I) according to embodiment E1 selected from the following group:
6-chloro-14-(4-hydroxyphenyl)-10,11-dimethyl-2,13-dioxo-20,23-dioxa-1,10,14-triazahexacyclo[26.3.1.1~9,12~.1~15,19~.0~3,8~.0~24,29~]tetratriaconta-3,5,7,9(34), 11,15(33), 16,18,24,26,28-undecaene-17-carbonitrile,
11-chloro-4-(4-hydroxyphenyl)-1,7,8-trimethyl-4,16,17,23,24,25-hexahydro-1H,14H-15,18-methano-6,9-(metheno)dibenzo[b,h]pyrazolo[4,3-p][1,6,11,15]oxatriazacycloicosine-5,14(8H)-dione,
6-chloro-14-(4-hydroxyphenyl)-10,11-dimethyl-2,13-dioxo-23-oxa-1,10,14-triazahexacyclo[26.3.1.1~9,12~.1~15, 19~.0~3,8~.0~24,29~]tetratriaconta-3,5,7,9(34), 11,15(33), 16,18,24,26,28-undecaene-17-carbonitrile,
11-chloro-4-(4-hydroxyphenyl)-1,7,8-trimethyl-5,14-dioxo-4,5,8,16,17,23,24,25-octahydro-1H,14H-15,18-metheno-6,9-(metheno)dibenzo[b,h]pyrrolo[3,2-p][1,6,11,15]oxatriazacycloicosine-2-carbonitrile,
11-chloro-4-(4-hydroxyphenyl)-1,7,8-trimethyl-5,14-dioxo-1,4,5,8,16,17,23,24-octahydro-14H-15,18-methano-6,9-(metheno)dibenzo[l,r]pyrrolo[2,3-d][1,6,10,15]oxatriazacyclononadecine-2-carbonitrile,
11-chloro-4-(4-hydroxyphenyl)-1,7,8-trimethyl-1,4,16,21,22,23-hexahydro-14H-15,21-methano-6,9-(metheno)dibenzo[j,o]pyrazolo[3,4-b][1,4,8,13]oxatriazacyclononadecine-5,14(8H)-dione,
(16S or R)-11-chloro-4-(4-hydroxyphenyl)-1,7,8,16-tetramethyl-5,14-dioxo-4,5,8,16,17,23,24,25-octahydro-1H,14H-15,18-methano-6,9-(metheno)dibenzo[b,h]pyrrolo[3,2-p][1,6,11,15]oxatriazacycloicosine-2-carbonitrile,
4-[16-chloro-3-hydroxy-19,20-dimethyl-13,22-dioxo-6,7,8,9,10,11,19,22-octahydro-13H,23H-8,12-methano-21,18-(metheno)dibenzo[b,j][1,4,8,13]oxatriazacyclononadecin-23-yl]-1,5-dimethyl-1H-pyrrole-2-carbonitrile,
10-fluoro-2-(4-hydroxyphenyl)-5,6-dimethyl-24,27,30-trioxa-2,6,15,32,35-pentaazahexacyclo[29.2.2.1~4,7~.1~15,19~.0~8,13~.0~18,23~]heptatriaconta-1(33),4,7(37),8,10,12,18,20,22,31,34-undecaene-3,14-dione,
10-chloro-2-(4-hydroxyphenyl)-5,6-dimethyl-24,30-dioxa-2,6,15,32,35-pentaazahexacyclo[29.2.2.1~4,7~.1~15, 19~.0~8,13~.0~18,23~]heptatriaconta-1(33),4,7(37),8, 10,12,18,20,22,31,34-undecaene-3,14-dione,
10-chloro-2-(4-hydroxyphenyl)-5,6,27-trimethyl-24,30-dioxa-2,6,15,27,32,35-hexaazahexacyclo[29.2.2.1~4, 7~.1~15,19~.0~8, 13~.0~18,23~]heptatriaconta-1(33),4,7(37),8,10,12,18,20,22,31,34-undecaene-3,14-dione,
11-chloro-4-(4-hydroxyphenyl)-1,7,8-trimethyl-1,4,16,17,23,24-hexahydro-14H-15,18-methano-6,9-(metheno)dibenzo[l,r]pyrazolo[3,4-d][1,6,10,15]oxatriazacyclononadecine-5,14(8H)-dione.

E14. Process for the preparation of a compound or formula (I) according to embodiment E1, characterised in that there is used as starting material the compound of formula (II):

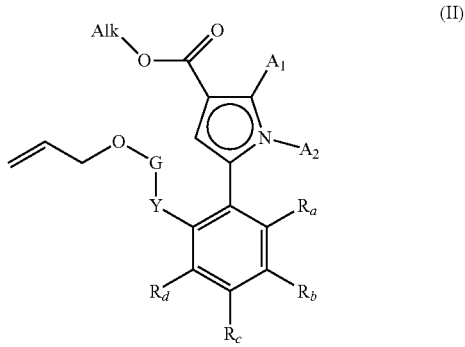

wherein $A_1$, $A_2$, $R_a$, $R_b$, $R_c$, $R_d$, Y and G have the same meaning as for formula (I) defined in E1, and Alk represents a linear or branched ($C_1$-$C_6$)alkyl group, the ester function —OAlk of which compound of formula (II) is hydrolysed to yield the corresponding carboxylic acid or carboxylate, which may be converted into the corresponding acyl chloride or anhydride before being coupled with an amine NHR$_{3A}$R$_4$, wherein R$_4$ has the same meaning as for formula (I) and R$_{3A}$ represents:
a group R$_3$ as defined in formula (I)
or a group R$_3$—O-Alk'-Z, R$_3$-Alk'-Z or R$_3$—Z wherein Alk' represents a linear or branched ($C_1$-$C_6$)alkyl group and Z represents a halogen atom or a —OH group.

to form the compound of formula (III):

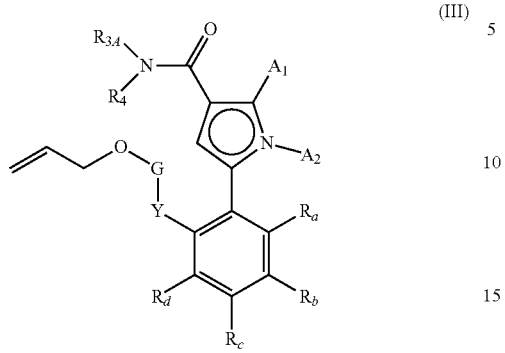

(III)

wherein $A_1$, $A_2$, $R_a$, $R_b$, $R_c$, $R_4$, Y and G have the same meaning as for formula (I), which is subjected to a reaction of deprotection of the alcohol function, followed either by an intramolecular nucleophilic substitution or by a Mitsunobu reaction or by an aromatic nucleophilic substitution, to yield the compound of formula (I), which compound of formula (I) may be purified according to a conventional separation technique, which may be converted into its addition salts with a pharmaceutically acceptable acid or base and which is optionally separated into its isomers according to a conventional separation technique, it being understood that, at any time considered appropriate in the course of the above-described process, the hydroxy and amino groups of the reagents or intermediates of synthesis may be protected and then deprotected according to the requirements of synthesis.

E15. Process for the preparation of a compound of formula (I) according to embodiment E1, characterised in that there is used as starting material the compound of formula (IV):

(IV)

wherein $R_3$, $R_4$ and X have the same meaning as for formula (I) and $G_A$ represents a group selected from the following list:

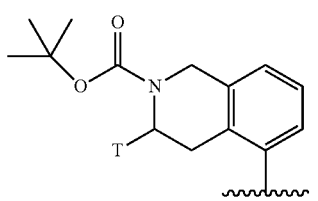

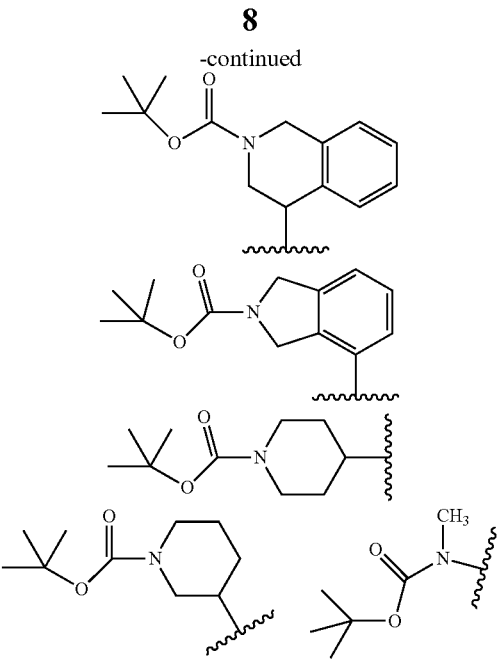

which compound of formula (IV) is then coupled with a compound of formula (V):

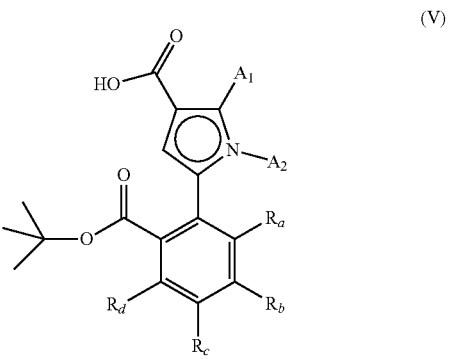

(V)

wherein $A_1$, $A_2$, $R_a$, $R_b$, $R_c$ and $R_d$ have the same meaning as for formula (I), to yield the compound of formula (VI):

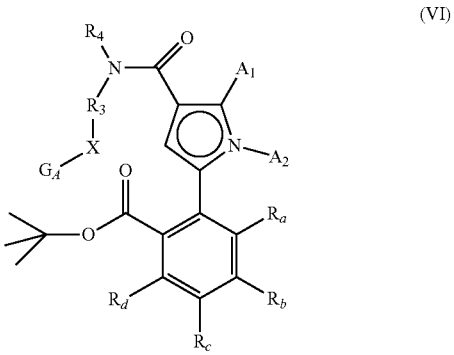

(VI)

wherein $A_1$, $A_2$, $R_a$, $R_b$, $R_c$, $R_d$, $R_3$, $R_4$ and X have the same meaning as for formula (I), which is subjected to a deprotection reaction followed by an intramolecular coupling to yield the compound of formula (I), which compound of formula (I) may be purified according to a conventional separation technique, which may be converted into its addition salts with a pharmaceutically acceptable acid or base and which is optionally separated into its isomers according to a conventional separation technique, it being understood that, at any time considered appropriate in the course of the above-described process, the hydroxy and amino groups of the reagents or intermediates of synthesis may be protected and then deprotected according to the requirements of synthesis.

E16. Pharmaceutical composition comprising a compound of formula (I) according to one of embodiments E1 to E13, or an addition salt thereof with a pharmaceutically acceptable acid or base, in combination with one or more pharmaceutically acceptable excipients.

E17. Pharmaceutical composition according to embodiment E16 for use as a pro-apoptotic agent.

E18. Pharmaceutical composition according to embodiment E16 for use in the treatment of cancers, auto-immune diseases and diseases of the immune system.

E19. Pharmaceutical composition according to embodiment E18 wherein the cancer is selected from the following list: cancer of the bladder, brain, breast and uterus, chronic lymphoid leukaemia, colorectal cancer, cancer of the esophagus and liver, lymphoblastic leukaemia, non-Hodgkin lymphoma, melanoma, malignant haemopathy, myeloma, ovarian cancer, non-small-cell lung cancer, prostate cancer and small-cell lung cancer.

E20. Use of a compound of formula (I) according to one of embodiments E1 to E13 in the manufacture of a medicament for use as a pro-apoptotic agent.

E21. Use of a compound of formula (I) according to one of embodiments E1 to E13 in the manufacture of a medicament for the treatment of cancers, immune diseases and auto-immune diseases.

E22. Use of a compound of formula (I) according to embodiment E21 wherein the cancer is selected from the following list: cancer of the bladder, brain, breast and uterus, chronic lymphoid leukaemia, colorectal cancer, cancer of the oesophagus and liver, lymphoblastic leukaemia, non-Hodgkin lymphoma, melanoma, malignant haemopathy, myeloma, ovarian cancer, non-small-cell lung cancer, prostate cancer and small-cell lung cancer.

E23. Combination of a compound of formula (I) according to one of embodiments E1 to E13 with an anti-cancer agent selected from genotoxic agents, mitotic poisons, anti-metabolites, proteasome inhibitors, kinase inhibitors and antibodies.

E24. Pharmaceutical composition comprising a combination according to embodiment E23 in combination with one or more pharmaceutically acceptable excipients.

E25. Combination according to embodiment E23 for use in the treatment of cancers.

E26. Use of a combination according to embodiment E23 in the manufacture of a medicament for use in the treatment of cancers.

E27. Compound of formula (I) according to one of embodiments E1 to E13 for use in association with radiotherapy in the treatment of cancers.

Among the pharmaceutical compositions according to the invention there may be mentioned more especially those that are suitable for oral, parenteral, nasal, per- or trans-cutaneous, rectal, perlingual, ocular or respiratory administration, especially tablets or dragdes, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn., 13, 2000, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol., 2001, 74(4):257-75), the protein Z derivative from the domain B of staphylococcal protein A, thioredoxin A or any protein with a repeated domain such as an "ankyrin repeat" (Kohl et al., PNAS, 2003, vol. 100, No. 4, 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention without limiting it in any way.

Preparation 1a: 4-Chloro-2-[4-(ethoxycarbonyl)-1,5-dimethyl-1H-pyrrol-2-yl]benzoic acid Step A: Ethyl 1,2-dimethyl-1H-pyrrole-3-carboxylate 60% sodium hydride (2.61 g; 65.3 mmol) is added, in 3 portions, to a solution of ethyl 2-methyl-1H-pyrrole-3-carboxylate (10 g; 65.3 mmol) and methyl iodide (8.95 mL; 130.6 mmol) in N,N-dimethylformamide (70 mL) placed at 0° C. The whole is then stirred at 0° C. for 1 hour. The reaction mixture is hydrolysed by addition of ice-water (420 mL) and then diluted with ethyl acetate. After decantation, the organic phase is washed in succession with 0.1 N aqueous hydrochloric acid solution, saturated aqueous lithium chloride solution and saturated aqueous sodium chloride solution and then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 6.65 (d, 1H), 6.3 (1d, 1H), 4.1 (1q, 2H); 3.5 (s, 3H), 2.4 (s, 3H), 1.5 (11, 3H).

IR: ν: >C=O: 1688 cm$^{-1}$; C—O—C: 1172 cm$^{-1}$.

Step B: Ethyl 5-(5-chloro-2-formylphenyl)-1,2-dimethyl-1H-pyrrole-3-carboxylate To a solution of the compound obtained in Step A (10 g; 62.8 mmol) in N,N-dimethylacetamide (65 mL) there are added in succession 2-bromo-4-chlorobenzaldehyde (15.2 g; 69 mmol), potassium acetate (12.3 g; 125.6 mmol), and then the whole is stirred under argon for 20 minutes. Dichlorobis(triphenylphosphine)palladium(II) (2.2 g; 3.14 mmol) is then added. The reaction mixture is then heated at 130° C. overnight. After returning to ambient temperature, the reaction mixture is diluted in dichloromethane, and bone black (2 g) is then added thereto. The whole is stirred at ambient temperature for 1 hour and then filtered. The organic phase is then washed with water, dried over magnesium sulphate and concentrated to dryness. The residue is purified by chromatography over silica gel using dichloromethane and ethanol as eluants to obtain the title product.

$^1$H NMR (400 MHz, dmso-d6, 300 K) δ ppm: 9.8 (s, 1H), 7.91-7.69-7.61 (d, 3H), 6.5 (s, 1H), 4.2 (q, 2H,), 3.4 (s, 3H), 2.55 (s, 3H), 1.28 (t, 3H).

Step C: 4-Chloro-2-[1-(ethoxycarbonyl)-1,5-dimethyl-1H-pyrrol-2-yl]benzoic acid The compound obtained in Step B (12.85 g; 42 mmol) and 2-methyl-2-butene (35.7 mL; 336 mmol) are dissolved in a mixture of acetone (20 mL) and tetrahydrofuran (20 mL). 200 mL of an aqueous solution containing a mixture of sodium chlorite (13.3 g; 147 mmol) and sodium hydrogen phosphate (14.5 g; 105 mmol) are added dropwise thereto. The whole is then stirred vigorously at ambient temperature for 7 hours. The reaction mixture is concentrated to remove the acetone and then diluted with ethyl acetate. After decantation, the organic phase is washed with water and concentrated to dryness. The residue is then taken up in a minimum amount of ethyl ether. The solid then obtained is filtered off, washed with ethyl ether and then dried in vacuo at 40° C. overnight. The title product is used subsequently without being purified further.

$^1$H NMR (400 MHz, dmso-d6, 300 K) δ ppm: 13 (m, 1H), 7.85 (d, 1H), 7.60 (dd, 1H), 7.41 (d, 1H), 6.3 (s, 1H), 4.15 (q, 2H), 3.25 (s, 3H), 2.5 (s, 3H), 1.25 (t, 3H).

IR: ν: —OH: 3100–2500 cm$^{-1}$; >C=O: 1681 cm$^{-1}$.

Preparation 2a: 5-(5-Chloro-2-formylphenyl)-1,2-dimethyl-1H-pyrrole-3-carboxylic acid

Step A: Ethyl 1,2-dimethyl-1H-pyrrole-3-carboxylate

A 50% by mass aqueous solution of chloroacetaldehyde (1206 g; 7.68 mol) is added over a period of 1 hour to a solution of ethyl acetoacetate (1000 g; 7.68 mol) in tetrahydrofuran (3 L) placed at −10° C. A 40% by mass aqueous solution of methylamine (1495 g; 19.2 mol) is then added over a period of 3 hours at −10° C. Then, the reaction mixture is heated at 30° C. over a period of 1.5 hours and stirred at that temperature for 16 hours. After returning to ambient temperature, the mixture is diluted in ethyl acetate (3 L) and the phases are separated. The basic aqueous phase is kept for extraction. The organic phase is cooled to 10° C. and 1 N aqueous hydrochloric acid solution (2.5 L) is added over a period of 15 minutes. The phases are separated and the organic phase is again washed with 1 N aqueous hydrochloric acid solution (2.5 L) and then with saturated aqueous sodium chloride solution (1 L). The basic and acidic aqueous phases are combined and washed with ethyl acetate (1.5 L). The organic phases are combined and washed with saturated aqueous sodium chloride solution (1 L), dried over sodium sulphate, filtered and concentrated to dryness. The product is purified by distillation in vacuo to obtain the title product.

$^1$H NMR (400 MHz, CDCl$_3$, 300 K) δ ppm: 6.50 (d, 1H), 6.45 (d, 1H), 4.25 (q, 2H), 3.51 (s, 3H), 2.49 (s, 3H), 1.33 (t, 3H).

Step B: 1,2-Dimethyl-1H-pyrrole-3-carboxylic acid

Lithium hydroxide monohydrate (251 g; 5.98 mmol) is added to a solution of the compound obtained in Step A (500 g; 2.99 mol) in water (5 L), and the mixture is heated at 100° C. for 2 hours. After returning to ambient temperature, the reaction mixture is washed with toluene (I L) and methylfen-butyl ether (I L). The aqueous phase is acidified with aqueous hydrochloric acid solution (530 mL) to pH=1 at a temperature of between 10 and 15° C., stirred for 1 hour and then filtered. The solid obtained is washed three times with water and dried in vacuo at a temperature of between 60 and 65° C. for 36 hours.

$^1$H NMR (400 MHz, CDCl$_3$, 300 K) δ ppm: 11.52 (s, 1H), 6.62 (d, 1H), 6.29 (d, 1H), 3.50 (s, 3H), 2.41 (s, 3H).

Step C: 5-(5-Chloro-2-formylphenyl)-1,2-dimethyl-M-pyrrole-3-carboxylic acid The title compound is obtained in accordance with the process described in Step B of Preparation 1a using 2-bromo-4-chlorobenzaldehyde acid and the compound obtained in the preceding step.

$^1$H NMR (400 MHz, dmso-d6, 300 K) δ ppm: 9.8 (s, 1H), 7.91 (d, 1H), 7.69 (dd, 1H), 7.61 (d, 1H), 6.5 (s, 1H), 4.2 (quad., 2H), 3.4 (s, 3H), 2.55 (s, 3H), 1.28 (t, 3H).

Preparation 1a': 5-(Prop-2-en-1-yloxy)-1,2,3,4-tetrahydroisoquinoline, hydrochloride (1:1)

Step A: tert-Butyl 5-hydroxy-3,4-dihydroisoquinoline-2(1H)-carboxylate

Platinum dioxide (2 g; 8.8 mmol) is added to a solution of 5-hydroxyisoquinoline (20 g; 137 mmol) in acetic acid (120 mL). The whole is placed under a hydrogen atmosphere (2 bar) for 24 hours. The reaction mixture is filtered and the catalyst is washed with toluene. The filtrate so obtained is concentrated to dryness. The residue obtained is used subsequently without being purified further.

To a solution of the residue obtained (1.95 g: 13 mmol) in dichloromethane (110 mL) there are added diisopropylethylamine (9.7 mL; 57 mmol) and di-tert-butyl dicarbonate (3.69 g, 16.9 mmol), and then the whole is stirred for 2 hours at ambient temperature. The reaction mixture is diluted with saturated aqueous ammonium chloride solution. After decantation, the organic phase is washed with saturated aqueous sodium hydrogen carbonate solution and then with saturated aqueous sodium chloride solution. It is then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 9.41 (m, 1H), 6.97 (t, 1H), 6.64/6.54 (2d, 2H), 4.42 (m, 2H), 3.53 (t, 2H), 2.59 (t, 2H), 1.42 (s, 9H).

IR: ν: —OH: 3294 cm$^{-1}$; >C=O: 1652 cm$^{-1}$.

Step B: tert-Butyl 5-(prop-2-en-1-yloxy)-3,4-dihydroisoquinoline-2(1H)-carboxylate To a solution of the compound obtained in Step A (10 g; 40.1 mmol) in acetonitrile (110 mL) there are added allyl bromide (6 mL; 60.2 mmol) and potassium carbonate (14.6 g, 120.3 mmol), and then the whole is stirred for 20 hours at ambient temperature. The reaction mixture is diluted with ethyl acetate. After decantation, the organic phase is washed with water and saturated aqueous sodium chloride solution and then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 7.8 (d, 1H), 7.12 (t, 1H), 6.75 (d, 1H), 6.05 (m, 1H), 5.41 (dquad, 1H), 5.28 (dquad, 1H), 4.58 (dt, 2H), 4.49 (s, 2H), 3.55 (t, 2H), 2.68 (t, 2H), 1.43 (s, 9H).

IR: ν: >C=O: 1691 cm$^{-1}$; >C—O—C<: 1162 cm$^{-1}$.

Step C: 5-(Prop-2-en-1-yloxy)-1,2,3,4-tetrahydroisoquinoline, hydrochloride (1:1)

4 N Hydrochloric acid solution in dioxane (33.4 mL; 133.5 mmol) is added to a solution of the compound obtained in Step B (9.7 g; 33.4 mmol) in dioxane (30 mL), and then the whole is stirred for 48 hours at ambient temperature. The reaction mixture is concentrated to dryness and the residue obtained is taken up in ethyl acetate and then filtered. The title product is obtained in the form of a solid, which is used without being purified further.

$^1$H NMR (400 MHz, dmso-d6, 300 K) δ ppm: 9.4 (s, 2H), 7.21 (t, 1H), 6.92 (d, 1H), 6.8 (d, 1H), 6.08 (m, 1H), 5.41 (dt, 1H), 5.29 (dt, 1H), 4.62 (m, 2H), 4.25 (s, 2H), 3.35 (t, 2H), 2.86 (t, 2H).

IR: ν: >NH$_2$+: 3250–2250 cm$^{-1}$.

Preparation 2a': 1,2,3,4-Tetrahydroisoquinolin-4-ylmethanol

Step A: Methyl 1,2,3,4-tetrahydroisoquinoline-4-carboxylate

Trimethylchlorosilane (5.4 mL; 42.3 mmol) is added to a solution of 1,2,3,4-tetrahydro-4-isoquinolinecarboxylic acid (5 g; 28.2 mmol) in methanol (40 mL), and then the whole is stirred for 16 hours at ambient temperature. After a second addition of trimethylchlorosilane (4 mL; 31.35 mmol), the reaction mixture is stirred for 16 hours at ambient temperature. The reaction mixture is then concentrated to dryness and the residue is taken up in methanol, and then the mixture is concentrated again. This operation is carried out twice to provide the title product, which is used subsequently without being purified further.

$^1$H NMR (400 MHz, dmso-d6, 300 K) δ ppm: 9.75-9.6 (unresolved peak, 2H), 7.4-7.25 (unresolved peak, 4H), 4.3 (s, 2H), 4.29 (m, 1H), 3.72 (s, 3H), 3.65/3.55 (ABx, 2H).

IR: ν: —NH2+: 3200–2150 cm$^{-1}$; >C=O: 1731 cm$^{-1}$.

Step B: 1,2,3,4-Tetrahydroisoquinolin-4-ylmethanol

The compound obtained in Step A (3.47 g; 18.1 mmol) in solution in tetrahydrofuran (50 mL) is added dropwise to a mixture of lithium aluminium hydride (1.24 g; 32.7 mmol) in tetrahydrofuran (50 mL) placed at 0° C. The reaction mixture is stirred for 2 hours at 0° C. and then hydrolysed with a mixture of water (11 mL) and 1 N aqueous sodium hydroxide solution (15 mL). After addition of ethyl acetate, the whole is stirred for 16 hours at ambient temperature. The insoluble material is then filtered off and the filtrate is extracted with ethyl acetate. The organic phases are combined and washed with saturated aqueous sodium chloride solution and then dried over magnesium sulphate, filtered and concentrated to dryness to provide the title product, which is used subsequently without being purified further.

$^1$H NMR (400 MHz, dmso-d6, 300 K) δ ppm: 7.2-6.95 (m, 4H), 3.8 (s, 2H), 3.6 (d, 2H), 3.3 (m, 2H), 3.18/2.85 (2dd, 2H), 2.65 (m, 1H).

IR: ν: —NH/—OH+: 3295 cm$^{-1}$; >C=C<: 1626 cm$^{-1}$.

Preparation 1a'': N-(4-{[tert-Butyl(dimethyl)silyl]oxy}phenyl)-3-(2-chloroethoxy)aniline

Step A: 1-Bromo-3-(2-chloroethoxy)benzene

Potassium carbonate (12 g; 86.7 mmol) is added to a solution of 3-bromophenol (5 g; 18.9 mmol) and bromochloroethane (3.7 mL; 43.3 mmol) in acetonitrile (80 mL), and then the whole is stirred at 80° C. for 24 hours. The reaction mixture is diluted with a mixture of ethyl acetate and water. After decantation, the organic phase is washed with water and saturated aqueous sodium chloride solution and then dried over magnesium sulphate, filtered and concentrated to dryness. The residue is purified by chromatography over silica gel using petroleum ether and ethyl acetate as eluants to obtain the title product.

$^1$H NMR (400 MHz, CDCl$_3$, 300 K) δ ppm: 7.15 (m, 2H), 7.09 (m, 1H), 6.85 (dt, 1H), 4.21 (t, 2H), 3.8 (t, 2H).

IR: ν: Ar: 1588 cm$^{-1}$; >C—O—C<: 1227 cm$^{-1}$; γ: >CH—Ar: 764 and 678 cm$^{-1}$.

Step B: 4-{[tert-Butyl)dimethyl)silyl]oxy}aniline

The title compound is obtained starting from 4-aminophenol in tetrahydrofuran in the presence of imidazole and tert-butyl(dimethyl)silyl chloride in accordance with the protocol described in the literature (S. Knaggs et al., *Organic car Bimolecular Chemistry*, 3(21), 4002-4010; 2005).

$^1$H NMR (400 MHz, dmso-d6, 300 K) δ ppm: 6.45-6.55 (dd, 4H), 4.60 (m, 2H), 0.90 (s, 9H), 0.10 (s, 6H).

IR: ν: —NH$_2$$^+$: 3300–3400 cm$^{-1}$

Step C: N-(4-{[tert-Butyl(dimethyl)silyl]oxy}phenyl)-3-(2-chloroethoxy)aniline A solution of the compounds obtained in Step A (4.8 g; 20.8 mmol) and in Step B (5.6 g; 24.9 mmol) in toluene (70 mL) is degassed by bubbling through argon for 10 minutes.

Sodium tert-butylate (2.4 g; 24.9 mmol) and chloro(2-di-tert-butylphosphino-2',4',6'-triisopropyl-1,1'-biphenyl)[2-(2-aminoethyl)phenyl]palladium(II) (0.7 g; 1 mmol) are added thereto. The whole is then stirred at 80° C. for 1 hour. The reaction mixture is filtered over Celite®. After rinsing with ethyl acetate, the filtrate is washed with water and saturated aqueous sodium chloride solution and then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 7.88 (s, 1H), 7.08 (t, 1H), 7 (d, 2H), 6.79 (d, 2H), 6.54 (dd, 1H), 6.49 (1, 1H), 6.32 (dd, 1H), 4.19 (t, 2H), 3.91 (t, 2H), 0.95 (s, 9H), 0.2 (s, 6H)

IR: ν: >NH: 3393 cm$^{-1}$; δ: Si—CH$_3$: 1250 cm$^{-1}$.

Preparation 2a": N-(4-{[tert-Butyl(dimethyl)silyl]oxy}phenyl)-3-(3-chloropropoxy)-aniline The title compound is obtained in accordance with the process of Preparation 1a", replacing bromochloroethane with bromochloropropane in Step A.

$^1$H NMR (400 MHz, dmso-d6, 300 K) δ ppm: 7.85 (s, 1H), 7.05 (t, 1H), 6.99 (d, 2H), 6.77 (d, 2H), 6.52 (dd, 1H), 6.48 (t, 1H), 6.31 (dd, 1H), 4.02 (t, 2H), 3.8 (t, 2H), 2.13 (quint., 2H), 0.95 (s, 9H), 0.2 (s, 6H).

IR: ν: >NH: 3398 cm$^{-1}$; δ: NH: 1504 cm$^{-1}$; δ: Si—CH$_3$: 1250 cm$^{-1}$.

Preparation 3a": N-(4-{[tert-Butyl(dimethyl)silyl]oxy}phenyl)-3-(4-chlorobutoxy)aniline The title compound is obtained in accordance with the process of Preparation 1a", replacing bromochloroethane with bromochlorobutane in Step A.

$^1$H NMR (400 MHz, dmso-d6, 300 K) δ ppm: 7.81 (m, 1H), 7.05 (in, 1H), 7 (m, 2H), 6.77 (m, 2H), 6.5 (m, 1H), 6.47 (m, 1H), 6.3 (m, 1H), 3.92 (m, 2H), 3.7 (m, 2H), 1.8 (m, 4H), 0.97 (m, 9H), 0.2 (m, 6H).

IR: ν: >NH: 3401 cm$^{-1}$.

Preparation 4a": 3-[(4-{[tert-Butyl(dimethyl)silyl]oxy}phenyl)amino]-5-(2-chloro-ethoxy)benzonitrile Step A: (3-Bromo-5-methoxyphenyl)methanol Borane-dimethyl sulphide complex (32.5 mL; 64.9 mmol) is added dropwise to a solution of 3-bromo-5-methoxybenzoic acid (10 g; 43.3 mmol) in tetrahydrofuran (280 mL), and then the whole is stirred for 2 hours. The reaction mixture is acidified dropwise with 2 N aqueous hydrochloric acid solution to pH=1. After extraction with ether, the organic phase is washed with 1 N aqueous sodium hydroxide solution and saturated aqueous sodium chloride solution and then dried over magnesium sulphate, filtered and concentrated to dryness. The title product is obtained in the form of an oil, which is used in the following step without being purified.

$^1$H NMR (400 MHz, dmso-d6, 300 K) δ ppm: 7.08 (m, 1H), 6.99 (m, 1H), 6.89 (m, 1H), 5.3 (br. s, 1H), 4.47 (s, 2H), 3.75 (s, 3H). "br" means "broad".

IR: ν: —OH: 1588 cm$^{-1}$; >C—O: 1268 and 1038 cm$^{-1}$; γ: >CH—Ar: 811 cm$^{-1}$.

Step B: 3-Bromo-5-methoxybenzaldehyde

Dess-Martin reagent (20.3 mL; 47.8 mmol) is added to a solution of the compound obtained in Step A (8.6 g; 39.8 mmol) in dichloromethane (400 mL), and then the whole is stirred for 2 hours. After addition of ether, the reaction mixture is filtered over a bed of silica. The filtrate is concentrated, taken up in a mixture of heptane and ethyl acetate and then again filtered over a bed of silica. After concentration of the filtrate, the title product is obtained in the form of a pale yellow solid, which is used in the following step without being purified.

$^1$H NMR (400 MHz, dmso-d6, 300 K) δ ppm: 9.5 (s, 1H), 7.69 (t, 1H), 7.5 (t, 1H), 7.42 (t, 1H), 3.85 (s, 3H).

IR: ν: >C=O: 1691 cm$^{-1}$.

Step C: (E)-1-(3-Bromo-5-methoxyphenyl)-N-hydroxymethanimine

To a solution of the compound obtained in Step B (7.8 g; 36.4 mmol) in ethanol (10 mL) there are added in succession hydroxylamine hydrochloride (12.6 g; 182 mmol) and pyridine (6.27 mL; 87.4 mmol), and then the whole is stirred at 65° C. for 1 hour. After returning to ambient temperature, the reaction mixture is diluted with a mixture of ethyl acetate and water. After decantation, the organic phase is washed with water and saturated aqueous sodium chloride solution and then dried over magnesium sulphate, filtered and concentrated to dryness. The title product is obtained in the form of a white solid, which is used in the following step without being purified.

$^1$H NMR (400 MHz, dmso-d6, 300 K) δ ppm: 11.45 (s, 1H), 8.1 (s, 1H), 7.35 (t, 1H), 7.16 (d, 2H), 3.8 (s, 3H).

IR: ν: —OH: 3300–3000 cm$^{-1}$; Ar: 1600 and 1564 cm$^{-1}$; >C—O: 1220 and 1059 cm$^{-1}$; —N—O: 960 cm$^{-1}$; γ: >CH—Ar: 831 cm$^{-1}$.

Step D: 3-Bromo-5-methoxybenzonitrile

To a solution of the compound obtained in Step C (8.1 g; 35.2 mmol) in dioxane (70 mL) there are added at 0° C. pyridine (22 mL; 211 mmol) and, dropwise, trifluoroacetic anhydride (1.4 mL; 70.4 mmol), and then the whole is stirred at ambient temperature for 24 hours. The reaction mixture is placed at 0° C. and then a second portion of trifluoroacetic anhydride (1.4 mL; 70.4 mmol) is added dropwise. The whole is then stirred at ambient temperature for 24 hours. The reaction mixture is again placed at 0° C. and then a third portion of trifluoroacetic anhydride (1.4 mL; 70.4 mmol) is added dropwise. The whole is stirred at 60° C. for 1 hour. After returning to ambient temperature, the reaction mixture is diluted with a mixture of dichloromethane and water. After decantation, the organic phase is washed with 1 N aqueous hydrochloric acid solution and saturated sodium chloride solution and then dried over magnesium sulphate, filtered and concentrated to dryness. The title product is obtained in the form of a pale yellow solid, which is used in the following step without being purified.

$^1$H NMR (400 MHz, dmso-d6, 300 K) δ ppm: 7.69 (t, 1H), 7.53 (dd, 1H), 7.5 (dd, 1H), 3.82 (s, 3H).

IR: ν: —CN: 2232 cm$^{-1}$; Ar: 1597 and 1562 cm$^{-1}$; >C—O—C<: 1278 and 1051 cm$^{-1}$; γ: >CH—Ar: 848, 814 and 671 cm$^{-1}$.

Step E: 3-Bromo-5-hydroxybenzonitrile

Lithium iodide (11.2 g; 83.7 mmol) is added to a solution of the compound obtained in Step D (5.9 g; 27.9 mmol) in 2,4,6-collidine (55 mL), and then the whole is stirred at 150° C. for 16 hours. After returning to ambient temperature, the reaction mixture is poured into ice-water. After extraction with dichloromethane, the organic phases are combined, washed with water and then dried over magnesium sulphate, filtered and concentrated to dryness. The title product is obtained in the form of a brown-orange solid, which is used in the following step without being purified.

$^1$H NMR (400 MHz, dmso-d6, 300 K) δ ppm: 10.7 (br. s, 1H), 7.51 (t, 1H), 7.3 (t, 1H), 7.18 (dd, 1H).

IR: ν: —OH: 3283 cm$^{-1}$; —CN: 2245 cm$^{-1}$.

Step F: 3-[(4-{[tert-Butyl(dimethyl)silyl]oxy}phenyl)amino]-5-(2-chloroethoxy)benzonitrile The title compound is obtained in accordance with the processes of Steps A and C of Preparation 1a" using the compound obtained in the preceding step and bromochloroethane as starting materials.

$^1$H NMR (400 MHz., dmso-d6, 300 K) δ ppm: 8.29 (s, 1H), 7.04 (d, 2H), 6.82 (d, 2H), 6.79/6.75/6.67 (3*m, 3H), 4.24 (dd, 2H), 3.91 (dd, 2H), 1.19 (s, 6H), 0.95 (s, 9H).

IR: ν: >NH: 3332 cm$^{-1}$; —CN: 2232 cm$^{-1}$; Ar: 1595 and 1504 cm$^{-1}$; >C—O—C<: 1250 cm$^{-1}$; γ: —Si—C: 828 cm$^{-1}$.

Preparation 5a": 3-[(4-{[tert-Butyl(dimethyl)silyl]oxy}phenyl)amino]-5-(3-chloro-propoxy)benzonitrile The title compound is obtained in accordance with the process of Preparation 4a", replacing bromochloroethane with bromochloropropane in Step F.

$^1$H NMR (400 MHz, dmso-d6, 300 K) δ ppm: 8.3 (m, 1H), 7.05-6.85 (m, 4H), 6.8-6.6 (m, 3H), 4.1 (m, 2H), 3.8 (m, 2H), 2.05 (m, 2H), 0.95 (m, 9H), 0.2 (m, 6H).

IR: ν: >NH: 3345 cm$^{-1}$; —CN: 2229 cm$^{-1}$.

Preparation 6a": N-(4-{[tert-Butyl(dimethyl)silyl]oxy}phenyl)-5-(3-chloropropyl)-1-methyl-1H-pyrazol-4-amine Step A: 5-(3-{[tert-Butyl(dimethyl)silyl]oxy}propyl)-1-methyl-1H-pyrazole A solution of n-butyllithium in hexane (26.8 mL; 42.9 mmol) is added dropwise at −78° C. to a solution of N-methylpyrazole (3.2 g; 39 mmol) in tetrahydrofuran (65 mL), and then the whole is stirred for 1 hour until it reaches a temperature of 0° C. again. The reaction mixture is then placed at −78° C., and (3-bromopropoxy)-tert-butyldimethylsilane (10.6 mL; 46.8 mmol) is added. The whole is stirred at ambient temperature for 16 hours and poured into a mixture of ice-water and ethyl acetate. After extraction with ethyl acetate, the organic phase is washed with saturated aqueous sodium chloride solution and then dried over magnesium sulphate, filtered and concentrated to dryness. The residue is purified by chromatography over silica gel using heptane and ethyl acetate as eluants to obtain the title product.

$^1$H NMR (400 MHz, CDCl$_3$, 300 K) δ ppm: 7.35 (d, 1H), 7 (d, 1H), 3.8 (s, 3H), 3.65 (t, 2H), 2.7 (m, 2H), 1.85 (m, 2H), 0.9 (s, 9H), 0.5 (s, 6H).

IR: γ: CH$_3$: 1254 cm$^{-1}$; ν: —Si—O—: 1098 cm$^{-1}$; —Si—C—: 834 and 772 cm$^{-1}$.

Step B: 3-(4-Bromo-1-methyl-1H-pyrazol-5-yl)propan-1-ol

Pyridinium tribromide (6.6 g; 20.8 mmol) is added at 0° C. to a solution of the compound obtained in Step A (4.8 g; 18.9 mmol) in methanol (200 mL). The whole is stirred for 1 hour at 0° C. and then for 16 hours at ambient temperature. After concentration of the reaction mixture, the residue is taken up in a mixture of 10% aqueous potassium carbonate solution and dichloromethane. After extraction with dichloromethane, the organic phase is washed with saturated aqueous sodium chloride solution and then dried over magnesium sulphate, filtered and concentrated to dryness. The residue is purified by chromatography over silica gel using dichloromethane and ammonia in methanol as eluants to obtain the title product.

$^1$H NMR (400 MHz, dmso-d6, 300 K) δ ppm: 7.45 (s, 1H), 4.59 (t, 1H), 3.79 (s, 3H), 3.4 (quad, 2H), 2.7 (t, 2H), 1.65 (m, 2H).

IR: ν: —OH: 3348 cm$^{-1}$.

Step C: 4-Bromo-5-(3-chloropropyl)-1-methyl-1H-pyrazole

Thionyl chloride (2.6 mL; 36.4 mmol) is added dropwise at 0° C. to a solution of the compound obtained in Step B (3.9 g; 17.2 mmol) in tetrahydrofuran (40 mL), and then the whole is stirred for 1 hour at 50° C. After concentration of the reaction mixture, the residue is taken up in a mixture of water and ethyl acetate. After extraction with ethyl acetate, the organic phase is washed with saturated aqueous sodium chloride solution and then dried over magnesium sulphate, filtered and concentrated to dryness. The residue is purified by chromatography over silica gel using dichloromethane and ammonia in methanol as eluants to obtain the title product.

$^1$H NMR (400 MHz, dmso-d6, 300 K) δ ppm: 7.48 (s, 1H), 3.8 (s, 3H), 3.69 (t, 2H), 2.8 (t, 2H), 1.95 (m, 2H).

Step D: N-(4-{[tert-Butyl(dimethyl)silyl]oxy}phenyl)-5-(3-chloropropyl)-1-methyl-1H-pyrazol-4-amine A solution of the compounds obtained in Step C (3.6 g; 15.2 mmol) and in Step B (3.4 g; 15.2 mmol) of Preparation 1a" in a mixture of toluene (25 mL) and tetrahydrofuran (25 mL) is degassed by bubbling through argon for 10 minutes. Sodium tert-butylate (1.75 g; 18.2 mmol) and chloro(2-di-tert-butylphosphino-2',4',6'-triisopropyl-1,1'-biphenyl)[2-(2-aminoethyl)phenyl]palladium(II) (0.5 g; 0.76 mmol) are added thereto, and then the whole is stirred at ambient temperature for 2 hours. The reaction mixture is filtered over Celite® and then concentrated after being rinsed with tetrahydrofuran. The residue is taken up in a mixture of water and dichloromethane and then extracted with dichloromethane, dried over magnesium sulphate, filtered and concentrated to dryness. The residue is purified by a first chromatography over silica gel using heptane and ethyl acetate as eluants and then a second chromatography using dichloromethane and ethyl acetate as eluants to obtain the title product.

$^1$H NMR (400 MHz, dmso-d6, 300 K) δ ppm: 7.21 (s, 1H), 6.59 (d, 2H), 6.45 (d, 2H), 3.72 (s, 3H), 155 (t, 2H), 2.89 (quint, 2H), 2.65 (t, 2H), 0.91 (s, 9H), 0.1 (s, 6H).

Preparation 7a": 4-[(4-{[tert-Butyl(dimethyl)silyl]oxy}phenyl)amino]-1-(4-chlorobutyl)-5-methyl-M-pyrrole-2-carbonitrile Step A: 5-Methyl-1H-pyrrole-2-carbonitrile Sodium ethanoate (100 g; 1.47 mol) is added to a solution of ethyl acetamidocyanoacetate (50.0 g; 0.29 mol) in ethanol (1.25 L), and then the whole is stirred for 10 minutes at 30° C. and then for 10 minutes at 50° C. At that temperature, a solution of 1,4-dichloro-2-butyne (72.3 g; 0.587 mol) in ethanol (250 mL) is added dropwise over a period of 2 hours, and then the whole is stirred at reflux for 100 minutes. After returning to ambient temperature, 2 N aqueous hydrochloric acid solution is added (588 mL), and then the ethanol is concentrated. After extraction with ethyl acetate, the organic phase is washed with saturated aqueous sodium chloride solution and then dried over magnesium sulphate, filtered and concentrated to dryness. The residue obtained is distilled in vacuo to obtain the title product.

$^1$H NMR (400 MHz, CDCl$_3$, 300 K) δ ppm: 8.76 (br. s, 1H), 6.76 (t, 1H), 5.93-5.96 (m, 1H), 2.3 (s, 3H).

Step B: 4-Bromo-5-methyl-1H-pyrrole-2-carbonitrile

A solution of bromine (59.9 g; 0.374 mol) in acetic acid (163 mL) is added at 10° C., over a period of 75 minutes, to a solution of the compound obtained in Step A (40.7 g; 0.341 mol) in a mixture of acetic acid (325 mL) and dichloromethane (122 mL). The whole is then stirred for 30 minutes at that temperature and then for 1 hour at ambient temperature. The reaction mixture is hydrolysed (200 mL) and the dichloromethane is concentrated. After returning to ambient temperature, water (400 mL) is added and the suspension obtained is stirred for 2 hours at 0° C. The precipitate is filtered off and dried in vacuo to obtain the title product without purification.

$^1$H NMR (400 MHz, CDCl$_3$, 300 K) δ ppm: 9.37 (br. s, 1H), 6.78 (d, 1H), 2.27 (s, 3H).

Step C: 4-Bromo-1-(4-chlorobutyl)-5-methyl-1H-pyrrole-2-carbonitrile

The compound obtained in Step B (4 g; 21.6 mmol) in N,N-dimethylformamide (120 mL) is added to a mixture of 60% sodium hydride in oil (0.95 g; 23.8 mmol) in a minimum amount of N,N-dimethylformamide, and then the whole is stirred for 15 minutes at ambient temperature before 1,4-dichlorobutane (4.7 mL; 43.2 mol) is added. The reaction mixture is allowed to act at ambient temperature for 3 days before being diluted in water (1.5 L). The product is then extracted with ethyl acetate. The organic phases are washed with saturated aqueous sodium chloride solution and then dried over magnesium sulphate, filtered and concentrated to dryness. The residue is purified by chromatography over silica gel using heptane and ethyl acetate as eluants to obtain the title product.

$^1$H NMR (400 MHz, CDCl$_3$, 300 K) δ ppm: 6.76 (s, 1H), 4.05 (1, 2H), 3.56 (t, 2H), 2.27 (s, 3H), 1.87-1.95 (in, 2H).

Step D: 4-[(4-{[tert-Butyl(dimethyl)silyl]oxy}phenyl)amino]-1-(4-chlorobutyl)-5-methyl-1H-pyrrole-2-carbonitrile The title compound is obtained in accordance with the process described in Step C of Preparation 1a'' starting from the compound obtained in the preceding step.

$^1$H NMR (400 MHz, CDCl$_3$, 300 K) δ ppm: 6.64-6.69 (m, 3H), 6.46-6.51 (m, 2H), 4.67 (br. s, 1H), 4.04 (t, 2H), 3.57 (t, 2H), 2.15 (s, 3H), 1.89-1.99 (m, 2H), 1.79-1.88 (m, 2H), 0.96 (s, 9H), 0.15 (s, 6H).

Preparation 8a'': 4-[(4-{[tert-Butyl(dimethyl)silyl]oxy}phenyl)amino]-1-(3-chloro-propyl)-5-methyl-1H-pyrrole-2-carbonitrile The title compound is obtained in accordance with the process of Preparation 7a'', replacing 1,4-dichlorobutane with bromochloropropane in Step C.

$^1$H NMR (400 MHz, CDCl$_3$, 300 K) δ ppm: 6.68 (s, 1H), 6.67 (d, 2H), 6.48 (d, 2H), 4.67 (br. s, 1H), 4.18 (t, 2H), 3.56 (t, 2H), 2.26 (quint., 2H), 2.18 (m, 3H), 0.96 (s, 9H), 0.15 (s, 6H).

Preparation 9a'': 3-[(4-{[tert-Butyl(dimethyl)silyl]oxy}phenyl)amino]-5-(3-chloro-propyl)benzonitrile Step A: (3-Bromo-5-iodophenyl)methanol 1 M borane-tetrahydrofuran complex in tetrahydrofuran (61.1 mL; 61.1 mmol) is added dropwise at 0° C. to a solution of 3-bromo-5-iodobenzoic acid (10 g; 30.58 mmol) in tetrahydrofuran (70 mL), and then the whole is stirred for 16 hours at ambient temperature. The reaction mixture is diluted in methanol (10 mL) and hydrolysed with 1 M aqueous sodium hydroxide solution (100 mL). Alter extraction with dichloromethane, the organic phase is washed with saturated aqueous sodium chloride solution and then dried over magnesium sulphate, filtered and concentrated to dryness. The title product is obtained in the form of a pale brown solid, which is used in the following step without being purified.

$^1$H NMR (400 MHz, CDCl$_3$, 300 K) δ ppm: 7.76-7.79 (m, 1H), 7.63-7.66 (m, 1H), 7.47-7.50 (m, 1H), 4.64 (s, 2H).

Step B: 3-Bromo-5-iodobenzaldehyde

Pyridinium dichromate (12.3 g; 32.8 mmol) is added to a solution of the compound obtained in Step A (7.89 g; 25.2 mmol) in dichloromethane (80 mL), and then the whole is stirred for 16 hours at ambient temperature. The reaction mixture is filtered over silica gel and then the filtrate is concentrated to provide the title product without purification.

$^1$H NMR (400 MHz, CDCl$_3$, 300 K) δ ppm: 9.87 (s, 1H), 8.12 (t, 1H), 8.10 (t, 1H), 7.96 (t, 1H).

Step C: 3-Bromo-5-iodobenzonitrile

To a solution of the compound obtained in Step B (6.95 g; 22.3 mmol) in tetrahydrofuran (60 mL) there are added 28% aqueous ammonium hydroxide solution (30 mL) and iodine (6.81 g; 26.8 mmol), and then the whole is stirred until the starting compound has disappeared. The reaction mixture is diluted with aqueous sodium sulphite solution until the orange colour has disappeared. After extraction with ethyl acetate, the organic phase is washed with saturated aqueous sodium chloride solution and then dried over sodium sulphate, filtered and concentrated to dryness with silica. The product so deposited on silica is purified by chromatography over silica gel using dichloromethane and heptane as eluants to obtain the title product.

$^1$H NMR (400 MHz, CDCl$_3$, 300 K) δ ppm: 8.10 (s, 1H), 7.92 (s, 1H), 7.76 (s, 1H).

Step D: 3-Bromo-5-(3-oxopropyl)benzonitrile

To a solution of the compound obtained in Step C (6.05 g; 19.6 mmol) in N,N-dimethylformamide (85 mL) there are added allyl alcohol (2.78 mL; 39.3 mmol), benzyltriethylammonium chloride (4.47 g; 19.6 mmol) and sodium bicarbonate (3.30 g; 39.3 mmol). After purging with nitrogen, palladium(II) acetate (0.13 g; 0.59 mmol) is added and then the whole is heated at 40° C. for 16 hours. The reaction mixture is diluted in a mixture of water (200 mL) and ethyl acetate (100 mL). After extraction with ethyl acetate, the organic phase is washed with saturated aqueous sodium chloride solution and then dried over sodium sulphate, filtered and concentrated to dryness. The residue is purified by chromatography over silica gel using ethyl acetate and heptane as eluants to obtain the title product.

$^1$H NMR (400 MHz, CDCl$_3$, 300 K) δ ppm: 9.81 (t, 1H), 7.64 (t, 1H), 7.59-7.61 (m, 1H), 7.44 (t, 1H), 2.93-3.02 (m, 2H), 2.81-2.88 (m, 2H).

Step E: 3-Bromo-5-(3-hydroxypropyl)benzonitrile

Sodium borohydride (0.62 g; 16.27 mmol) is added in portions to a solution of the compound obtained in Step D (2.98 g; 12.52 mmol) in methanol (30 mL). The whole is stirred at ambient temperature for 30 minutes. The reaction mixture is diluted with 1 M aqueous sodium hydroxide solution (50 mL). After extraction with dichloromethane, the organic phase is washed with saturated aqueous sodium chloride solution and then dried over sodium sulphate, filtered and concentrated to dryness to obtain the title product without purification.

$^1$H NMR (400 MHz, CDCl$_3$, 300 K) δ ppm: 7.61-7.64 (m, 1H), 7.59-7.61 (m, 1H), 7.44 (t, 1H), 3.68 (t, 2H), 2.72-2.79 (m, 2H), 1.83-1.93 (m, 2H).

Step F: 3-Bromo-5-(3-chloropropyl)benzonitrile

Methanesulphonyl chloride (1.65 mL; 21.4 mmol) is added to a solution of the compound obtained in Step E (2.57 g; 10.7 mmol) and triethylamine (3.43 mL; 24.6 mmol) in dichloromethane (30 mL) at 0° C. The whole is stirred at ambient temperature for 2 hours and then tetrabutylammonium chloride (8.92 g; 32.1 mmol) is added. The reaction mixture is stirred for 16 hours and then diluted in a mixture of water and dichloromethane. After extraction with ethyl acetate, the organic phase is washed with saturated aqueous sodium chloride solution and then dried over sodium sulphate, filtered and concentrated to dryness. The residue is purified by chromatography over silica gel using ethyl acetate and heptane as eluants to obtain the title product.

$^1$H NMR (400 MHz, CDCl$_3$, 300 K) δ ppm: 7.65 (t, 1H), 7.60 (s, 1H), 7.44 (s, 1H), 3.53 (t, 2H), 2.78-2.86 (m, 2H), 2.04-2.14 (m, 2H).

Step G: 3-[(4-{[tert-Butyl(dimethyl)silyl]oxy}phenyl)amino]-5-(3-chloropropyl)benzonitrile The title compound is obtained in accordance with the process described in Step C of Preparation 1a" starting from the compound obtained in the preceding step.

$^1$H NMR (400 MHz, CDCl$_3$, 300 K) δ ppm: 6.78-7.07 (m, 7H), 5.60 (br. s, 1H), 3.52 (t, 2H), 2.71 (t, 2H), 2.00-2.10 (m, 2H), 0.99 (s, 9H), 0.27 (s, 6H).

Preparation 10a": N-(4-{[tert-Butyl(dimethyl)silyl]oxy}phenyl)-1-methyl-5-[2-(tetrahydro-2H-pyran-2-yloxy)ethyl]-1H-pyrazol-4-amine Step A: 5-(2-{[tert-Butyl(dimethyl)silyl]oxy}ethyl)-1-methyl-1H-pyrazole The title compound is obtained in accordance with the process described in Step A of Preparation 6a", replacing (3-bromopropoxy)-tert-butyldimethylsilane with (2-bromoethoxy)-tert-butyldimethylsilane.

$^1$H NMR (400/500 MHz, CDCl$_3$, 300 K) δ ppm: 7.35 (d, 1H), 7 (d, 1H), 3.8 (s, 3H), 3.65 (t, 2H), 2.7 (m, 2H), 1.85 (m, 2H), 0.9 (s, 9H), 0.5 (s, 6H)

IR: ν: —Si—O—: 1098 cm$^{-1}$; —Si—C—: 834 and 772 cm$^{-1}$.

Step B: 2-(4-Bromo-1-methyl-M-pyrazol-5-yl)ethanol

The title compound is obtained in accordance with the process described in Step B of Preparation 6a".

$^1$H NMR (400 MHz, dmso-d6, 300 K) δ ppm: 7.45 (s, 1H), 4.59 (t, 1H), 3.79 (s, 3H), 3.4 (quad, 2H), 2.7 (t, 2H), 1.65 (m, 2H).

IR: ν: —OH: 3348 cm$^{-1}$.

Step C: 4-Bromo-1-methyl-5-[2-(tetrahydro-2H-pyran-2-yloxy)ethyl]-1H-pyrazole

To a solution of the compound obtained in the preceding step (5.34 g; 2.4 mmol) in dichloromethane (40 mL) there are added 3,4-dihydro-2H-pyran (7 mL; 6 mmol) and para-toluenesulphonic acid (4.6 g; 2.4 mmol), and then the whole is stirred for 16 hours. The reaction mixture is diluted in saturated aqueous sodium hydrogen carbonate solution. After extraction with dichloromethane, the organic phase is dried over magnesium sulphate, filtered and concentrated to dryness. The residue is purified by chromatography over silica gel using heptane and ethyl acetate as eluants to obtain the title product.

$^1$H NMR (400 MHz, dmso-d6, 300 K) δ ppm: 7.42 (s, 1H), 4.55 (t, 1H), 3.8-3.3 (m, 4H), 3.8 (s, 3H), 2.71 (m, 2H), 1.78 (m, 2H), 1.7-1.4 (m, 6H).

Step D: N-(4-{[tert-Butyl(dimethyl)silyl]oxy}phenyl)-1-methyl-5-[2-(tetrahydro-2H-pyran-2-yloxy)ethyl]-1H-pyrazol-4-amine The title compound is obtained in accordance with the process described in Step D of Preparation 6a" starting from the brominated compound of the preceding step.

$^1$H NMR (500 MHz, dmso-d6, 300 K) δ ppm: 7.2 (s, 1H), 6.6 (s, 1H), 6.55 (d, 2H), 6.45 (d, 2H), 4.4 (t, 1H), 3.7 (s, 3H), 3.65-3.2 (4m, 4H), 2.58 (m, 2H), 1.68 (m, 2H), 1.6-1.3 (m, 6H), 0.92 (s, 9H), 0.1 (s, 6H).

IR: ν: >NH: 3356 cm$^{-1}$; ->C—C—O—: 1240 cm$^{-1}$.

Preparation 11a"

Step A: 4-(Prop-2-en-1-yloxy)aniline

Concentrated sodium hydroxide solution (7 mL; 83.6 mmol) is added to a solution of N-(allyloxyphenyl)acetamide (4 g; 20.9 mmol) in ethanol (30 mL). The whole is stirred at 100° C. for 24 hours. After returning to ambient temperature, the ethanol of the reaction mixture is concentrated and then the residue is taken up in water (100 mL). After extraction with dichloromethane, the organic phases are dried over magnesium sulphate, filtered and concentrated to dryness to obtain the title product without purification.

$^1$H NMR (400 MHz, dmso-d6, 300 K) δ ppm: 6.66 (d, 2H), 6.49 (d, 2H), 6 (m, 1H), 5.34 (dq, 1H), 5.2 (dq, 1H), 4.59 (s, 2H), 4.4 (dt, 2H).

IR: ν: —NH2: 3428, 3354 and 3220 cm$^{-1}$.

Step B: 4-Fluoro-3-{[4-(prop-2-en-1-yloxy)phenyl]amino}benzonitrile

The title compound is obtained in accordance with the process of Step C of Preparation 1a" using the compound obtained in the preceding step and 3-bromo-4-fluorobenzonitrile.

$^1$H NMR (400 MHz, dmso-d6, 300 K) δ ppm: 8.08 (s, 1H), 7.36 (dd, 1H), 7.24 (dd, 1H), 7.19 (m, 1H), 7.12 (d, 2H), 6.96 (d, 2H), 6.05 (m, 1H), 5.4 (ddt, 1H), 5.26 (ddt, 1H), 4.56 (dt, 2H).

IR: ν: —NH: 3327 cm$^{-1}$; >CN: 2235 cm$^{-1}$.

Preparation 1b: 5-[2-(tert-Butoxycarbonyl)-5-chlorophenyl]-1,2-dimethyl-1H-pyrrole-3-carboxylic acid

Step A: Ethyl 1,2-dimethyl-1H-pyrrole-3-carboxylate

The procedure is identical to that described in Step A of Preparation 1a.

$^1$H NMR (400 MHz, CDCl$_3$, 300 K) δ ppm: 6.50 (d, 1H), 6.45 (d, 1H), 4.25 (q, 2H), 3.51 (s, 3H), 2.49 (s, 3H), 1.33 (t, 3H).

Step B: 1,2-Dimethyl-1H pyrrole-3-carboxylic acid

The procedure is identical to that described in Step B of Preparation 1a.

$^1$H NMR (400 MHz, CDCl$_3$, 300 K) δ ppm: 11.52 (s, 1H), 6.62 (d, 1H), 6.29 (d, 1H), 3.50 (s, 3H), 2.41 (s, 3H).

Step C: tert-Butyl 2-bromo-4-chlorobenzoate

To a solution of magnesium sulphate (1431 g; 11.9 mol) in dichloromethane (10.5 L) there are added sulphuric acid (287 g; 2.97 mol) over a period of 30 minutes, then 2-bromo-4-chlorobenzoic acid (700 g; 2.97 mol) and 700 mL of tert-butanol. The reaction mixture is stirred for 4 days at ambient temperature and then filtered. The filtrate is washed with 5% aqueous potassium hydrogen carbonate solution, and then the organic phase is dried over sodium sulphate and concentrated to dryness and then reconcentrated in heptane (1 L) to obtain the title product.

$^1$H NMR (400 MHz, CDCl$_3$, 300 K) δ ppm: 7.65 (d+d, 2H), 7.30 (dd, 1H), 1.65 (s, 9H).

Step D: 5-[2-(tert-Butoxycarbonyl)-5-chlorophenyl]-1,2-dimethyl-1H-pyrrole-3-carboxylic acid To a degassed (by bubbling through nitrogen for 15 minutes) solution of the residue obtained in Step C (187.5 g; 0.643 mol) and the compound obtained in Step B (89.6 g; 0.643 mol) in N,N-dimethylformamide (1.87 L) there is added potassium carbonate (178 g; 1.29 mol, sprayed beforehand by means of an Ultra-Turrax® grinder) in suspension in ethyl acetate. The suspension is then degassed for a further 15 minutes. Palladium(II) acetate (7.2 g, 0.003 mol) is added, and then the suspension is heated to 100° C. and stirred for 18 hours. After returning to ambient temperature, the reaction mixture is diluted with water (950 mL). This same operation is carried out a second time with the same quantity of the compound obtained in Step C.

The two solutions are combined and washed with methyl tert-butyl ether. The aqueous phases at pH=10 are acidified to pH=2 with 12 N aqueous hydrochloric acid solution at a temperature of between 10 and 20° C. The suspension obtained is cooled to 0° C., stirred for 1 hour and then filtered. The solid is washed with water (2 L) and then suction filtered for 1 hour. Carbon (375 g) is added to a solution of the residue taken up in methanol (12 L). The suspension is heated to 40° C. and stirred for 2 hours. The mixture is filtered over Celite® (375 g) and the solid is washed with methanol. The filtrate is concentrated to dryness and the residue obtained is diluted in a mixture of ethanol (1.3 L) and methanol (400 mL). The suspension is distilled; 400 mL of distillate are collected. Ethanol (1 L) is added in order to continue the distillation until 1 L of distillate has been collected. After returning to ambient temperature, the suspension is stirred for 16 hours and then cooled to 0° C. and stirred again for 2 hours. The product is filtered off and washed with cold ethanol before being dried in vacuo at 60° C. for 16 hours. The title product is obtained in the form of a white solid.

$^1$H NMR (400 MHz, dmso-d6, 300 K) δ ppm: 10.87-12.20 (s, 1H), 7.77 (d, 1H), 7.57 (dd, 1H), 7.44 (d, 1H), 6.25 (s, 1H), 3.25 (s, 3H), 2.51 (s, 3H), 1.25 (t, 9H).

Preparation 2b: 5-[2-(tert-Butoxycarbonyl)-5-fluorophenyl]-1,2-dimethyl-1H-pyrrole-3-carboxylic acid The title compound is obtained in accordance with the process of Preparation 1b using 2-bromo-4-fluorobenzoic acid in Step C.

$^1$H NMR (400 MHz, CDCl$_3$, 300 K) δ ppm: 12.18 (s, 1H), 7.93 (dd, 1H), 7.14 (td, 1H), 7.03 (dd, 1H), 6.52 (s, 1H), 3.27 (s, 3H), 2.60 (s, 3H), 1.33 (t, 9H).

Preparation 1b': tort-Butyl 5-(3-hydroxypropyl)-3,4-dihydroisoquinoline-2(1H)-carboxylate

Step A: Methyl (2E)-3-(isoquinolin-5-yl)prop-2-enoate

5-Bromoisoquinoline (5 g; 24.1 mmol) is added to a sealed tube containing a solution of methyl acrylate (5.4 mL; 60.2 mmol), triphenylphosphine (0.63 g; 2.4 mmol), triethylamine (13.4 mL; 96.0 mmol) and palladium(II) acetate (0.27 g; 1.2 mmol) in N,N-dimethylformamide (30 mL). Nitrogen is bubbled through the mixture for 10 minutes, and then the tube is sealed and plunged into an oil bath at 120° C. The reaction mixture is stirred for 1.5 hours and then hydrolysed after returning to ambient temperature. The product is extracted with ethyl acetate and then the organic phases are washed with saturated aqueous sodium chloride solution, dried over magnesium sulphate, filtered and concentrated to dryness. The residue is purified by chromatography over silica gel using heptane and ethyl acetate as eluants to obtain the title product.

$^1$H NMR (400 MHz, CDCl$_3$, 300 K) δ ppm: 9.29 (s, 1H), 8.62 (d, 1H), 8.42 (d, 1H), 8.03 (d, 1H), 7.94-8.01 (m, 2H), 7.64 (t, 1H), 6.57 (d, 1H), 3.88 (s, 3H).

Step B: tert-Butyl 5-[(1E)-3-methoxy-3-oxoprop-1-en-1-yl]-3,4-dihydroisoquinoline-2(1H)-carboxylate A solution of the compound obtained in Step A (7.24 g; 34 mmol) and sodium cyanoborohydride (9.6 g; 152.8 mmol) in methanol (200 mL) is placed at 45° C. Boron trifluoride diethyl-etherate (18.9 mL; 152.8 mmol) is added dropwise, and then the reaction mixture is stirred for 20 minutes at that temperature, and di-tert-butyl carbonate (8.15 g; 37.4 mmol) and then triethylamine (14.2 mL; 101.9 mmol) are added.

The reaction mixture is stirred for 15 minutes at 45° C. After returning to ambient temperature, it is hydrolysed with water and 1 N aqueous sodium hydroxide solution. The product is extracted with ethyl acetate and then the organic phases are washed with aqueous hydrochloric acid solution and water, dried over magnesium sulphate, filtered and concentrated to dryness to obtain the title product.

¹H NMR (400 MHz, CDCl₃, 300 K) δ ppm: 7.94 (d, 1H), 7.44 (d, 1H), 7.21 (t, 1H), 7.11-7.17 (m, 1H), 6.35 (d, 1H), 4.58 (s, 2H), 3.81 (s, 3H), 3.67 (t, 2H), 2.93 (t, 2H), 1.49 (s, 9H).

Step tert-Butyl 5-[(1E)-3-hydroxyprop-1-en-1-yl]-3,4-dihydroisoquinoline-2(1H)-carboxylate A solution of the compound obtained in Step B (10.78 g; 34 mmol) in toluene (200 mL) is added slowly at −78° C. to a 25% by mass diisobutylaluminium hydride solution in toluene (50 mL; 74.7 mmol). The reaction mixture is stirred for 20 minutes at that temperature, and then methanol is added slowly. After returning to ambient temperature, the reaction mixture is hydrolysed with water and 1 N aqueous sodium hydroxide solution. The product is extracted with ethyl acetate and then the organic phases are washed with saturated aqueous sodium chloride solution, dried over magnesium sulphate, filtered and concentrated to dryness to obtain the title product.

¹H NMR (400 MHz, CDCl₃, 300 K) δ ppm: 7.33 (d, 1H), 7.17 (t, 1H), 7.03 (d, 1H), 6.80 (d, 1H), 6.24 (dt, 1H), 4.54-4.60 (m, 2H), 4.35 (d, 2H), 3.65 (t, 2H), 2.84 (t, 2H), 1.49 (s, 9H).

Step D: tert-Butyl 5-(3-hydroxypropyl)-3,4-dihydroisoquinoline-2(1H)-carboxylate Palladium on carbon (1 g; 10% by mass) is added to a solution of the compound obtained in Step C (9.82 g; 34.0 mmol) in methanol (300 mL). The reaction mixture is hydrogenated for 16 hours and then filtered over Celite®. The filtrate is concentrated to dryness to obtain the title product.

¹H NMR (400 MHz, CDCl₃, 300 K) δ ppm: 7.32 (d, 1H), 7.16 (t, 1H), 7.02 (d, 1H), 6.79 (d, 1H), 6.24 (dt, 1H), 4.57 (s, 2H), 4.34 (d, 2H), 3.62-3.67 (m, 2H), 3.49 (s, 2H), 2.84 (t, 2H), 1.49 (s, 9H).

Preparation 2b': tert-Butyl 5-(4-hydroxybutoxy)-3,4-dihydroisoquinoline-2(1H)-carboxylate Step A: tert-Butyl 5-hydroxy-3,4-dihydroisoquinoline-2(1H)-carboxylate Platinum dioxide (2 g; 8.8 mmol) is added to a solution of 5-hydroxy-isoquinoline (20 g; 137 mmol) in acetic acid (120 mL). The whole is placed under a hydrogen atmosphere (2 bar) for 24 hours. The reaction mixture is filtered and the catalyst is washed with toluene. The filtrate so obtained is concentrated to dryness. The title product is obtained in the form of an oil, which is used subsequently without being purified.

To a solution of the residue obtained (1.95 g; 13 mmol) in dichloromethane (110 mL) there are added diisopropylethylamine (9.7 mL; 57 mmol) and di-tert-butyl dicarbonate (3.69 g, 16.9 mmol), and then the whole is stirred for 2 hours at ambient temperature. The reaction mixture is diluted with saturated aqueous ammonium chloride solution. After decantation, the organic phase is washed with saturated aqueous sodium hydrogen carbonate solution and saturated aqueous sodium chloride solution and then dried over magnesium sulphate, filtered and concentrated to dryness. The residue is purified by chromatography over silica gel using petroleum ether and ethyl acetate as eluants to obtain the title product.

¹H NMR (400 MHz, dmso-d6, 300 K) δ ppm: 9.41 (m, 1H), 6.97 (t, 1H), 6.64/6.54 (2d, 2H), 4.42 (m, 2H), 3.53 (t, 2H), 2.59 (t, 2H), 1.42 (s, 9H).

IR: v: —OH: 3294 cm⁻¹; >C=O: 1652 cm⁻¹.

Step B: Bert-Butyl 5-[4-(tetrahydro-2H-pyran-2-yloxy)butoxy]-3,4-dihydroisoquinoline-2(1H)-carboxylate To a solution of the compound obtained in Step A (1 g; 4 mmol) in acetonitrile (15 mL) there are added 2-(4-bromobutoxy)-tetrahydropyran (0.77 mL; 4.2 mmol) and caesium carbonate (1.4 g, 4.2 mmol), and then the whole is stirred for 18 hours at 70° C. The reaction mixture is diluted with ethyl acetate and water. After decantation, the organic phase is washed with saturated aqueous sodium chloride solution and then dried over magnesium sulphate, filtered and concentrated to dryness. The residue is purified by chromatography over silica gel using heptane and ethyl acetate as eluants to obtain the title product.

¹H NMR (400 MHz, dmso-d6, 300 K) δ ppm: 7.12 (dd, 1H), 6.79 (d, 1H), 6.72 (d, 1H), 4.55 (t, 1H), 4.45 (s, 2H), 3.98 (t, 2H), 3.74/3.42 (2*m, 2H), 3.68/3.41 (2*m, 2H), 3.54 (t, 2H), 2.63 (t, 2H), 1.79 (m, 2H), 1.74-1.4 (m, 6H), 1.68 (m, 2H), 1.42 (s, 9H).

IR: v: >C=O: 1693 cm⁻¹; >C—O—C<: 1033 cm⁻¹.

Step C: tert-Butyl 5-(4-hydroxybutoxy)-3,4-dihydroisoquinoline-2(1H)-carboxylate Pyridinium para-toluenesulphonate (0.16 g; 0.64 mmol) is added to a solution of the compound obtained in Step B (1.29 g; 3.18 mmol) in methanol (50 mL), and then the whole is stirred for 8 hours at 60° C. The reaction mixture is diluted with dichloromethane and saturated aqueous ammonium chloride solution. After decantation, the organic phase is washed with water and then dried over magnesium sulphate, filtered and concentrated to dryness. The residue is purified by chromatography over silica gel using heptane and ethyl acetate as eluants to obtain the title product.

¹H NMR (400 MHz, dmso-d6, 300 K) δ ppm: 7.12 (dd, 1H), 6.78 (d, 1H), 6.72 (d, 1H), 4.45 (s, 2H), 4.42 (t, 1H), 3.96 (1, 2H), 3.54 (t, 2H), 3.45 (m, 2H), 2.62 (t, 2H), 1.75 (m, 2H), 1.58 (m, 2H), 1.42 (s, 9H).

IR: v: —OH: 3600–3100 cm⁻¹; >C=O: 1693 cm⁻¹

Preparation 3b': tert-Butyl 5-hydroxy-3,4-dihydroisoquinoline-2(1H)-carboxylate

Platinum dioxide (2 g; 8.8 mmol) is added to a solution of 5-hydroxy-isoquinoline (20 g; 137 mmol) in acetic acid (120 mL). The whole is placed under a hydrogen atmosphere (2 bar) for 24 hours. The reaction mixture is filtered and the catalyst is washed with toluene. The filtrate so obtained is concentrated to dryness. The title product is obtained in the form of an oil, which is used subsequently without being purified.

To a solution of the residue obtained (1.95 g; 13 mmol) in dichloromethane (110 mL) there are added diisopropylethylamine (9.7 mL; 57 mmol) and di-ten-butyl dicarbonate (3.69 g, 16.9 mmol), and then the whole is stirred for 2 hours at ambient temperature. The reaction mixture is diluted with saturated aqueous ammonium chloride solution. After decantation, the organic phase is washed with saturated aqueous sodium hydrogen carbonate solution and saturated aqueous sodium chloride solution and then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 9.41 (m, 1H), 6.97 (t, 1H), 6.64/6.54 (2d, 2H), 4.42 (m, 2H), 3.53 (t, 2H), 2.59 (t, 2H), 1.42 (s, 9H).

IR: ν: —OH: 3294 cm-1; >C=O: 1652 cm-1.

Preparation 4b': tert-Butyl 5-hydroxy-3-(morpholin-4-ylmethyl)-3,4-dihydro-isoquinoline-2(1H)-carboxylate Step A: Methyl 3-methoxy-2-methylbenzoate Thionyl chloride (17.5 mL; 0.24 mol) is added dropwise at 0° C. to a solution of 2-methyl-3-methoxybenzoic acid (20 g; 0.12 mol) in methanol (200 mL). The reaction mixture is heated at reflux for 2 hours. After returning to ambient temperature, the reaction mixture is concentrated and then diluted in a mixture of ethyl acetate and 1 N aqueous sodium hydroxide solution. After decantation, the organic phase is washed with water and saturated aqueous sodium chloride solution and then dried over magnesium sulphate, filtered and concentrated to dryness. The title product is obtained in the form of an oil, which is used in the following step without being purified.

$^1$H NMR (400 MHz, CDCl$_3$, 300 K) 3 ppm: 7.39 (dd, 1H), 7.19 (t, 1H), 6.98 (d, 1H), 3.89 (s, 3H), 3.84 (s, 3H), 2.42 (s, 3H).

IR: ν: >C=O: 1719; >C—O—C 1254 and 1066 cm$^{-1}$.

Step B: Methyl 2-(bromomethyl)-3-methoxybenzoate

To a solution of the compound obtained in Step A (19.8 g; 0.11 mol) in carbon tetrachloride (100 mL) there are added N-bromosuccinimide (19.56 g; 0.18 mol) and azoisobutyronitrile (2 g; 0.012 mol). The reaction mixture is heated at reflux for 3 hours. After returning to ambient temperature, the reaction mixture is diluted in a mixture of dichloromethane and water. After decantation, the organic phase is washed with saturated aqueous sodium chloride solution and then dried over sodium sulphate, filtered and concentrated to dryness. The residue is taken up in dichloromethane to provide the title product in the form of a white solid, which is used in the following step without being purified.

$^1$H NMR (400 MHz, CDCl$_3$, 300 K) δ ppm: 7.51 (d, 1H), 7.31 (t, 1H), 7.08 (d, 1H), 5.05 (s, 2H), 3.91 (2s, 6H).

IR: ν: >C=O: 1713 cm$^{-1}$.

Step C: Diethyl (acetylamino)[2-methoxy-6-(methoxycarbonyl)benzyl]propanedioate

A solution of diethyl acetamidomalonate (16.9 g; 77.8 mmol) in N,N-dimethylformamide (100 mL) is added dropwise, at a temperature below 30° C., to a suspension of sodium hydride (3.42 g; 85.6 mmol) in N,N-dimethylformamide. The reaction mixture is stirred for 15 minutes, and then a solution of the compound obtained in Step B (21.2 g; 81.67 mmol) is added dropwise at ambient temperature. After 18 hours' contact, the reaction mixture is concentrated and then diluted in a mixture of ethyl acetate and saturated aqueous sodium hydrogen carbonate solution. After extraction with ethyl acetate, the organic phases are combined, washed with water and saturated aqueous lithium chloride solution and then dried over sodium sulphate, filtered and concentrated to dryness. The residue is taken up in diisopropyl ether to provide the title product in the form of a broken white solid, which is used in the following step without being purified.

$^1$H NMR (400 MHz, dmso-d6, 300 K) δ ppm: 7.68 (s, 1H), 7.3 (t, 1H), 7.1 (2d, 2H), 4.15/4.05 (2m, 4H), 3.81 (s, 2H), 3.71/3.7 (2s, 6H), 1.79 (s, 3H), 1.15 (t, 6H).

IR: ν: —NH: 3367; >C=O: 1755, 1732 and 1707; >C=O: 1668; >C=C<: 1600 cm$^{-1}$.

Step D: 5-Methoxy-1-oxo-1,2,3,4-tetrahydrisoquinoline-3-carboxylic acid

Acetic acid (40 mL) is added to a solution of the compound obtained in Step C (8.1 g; 20 mmol) in 5 N aqueous hydrochloric acid solution. The reaction mixture is heated at reflux for 18 hours and is then filtered after returning to ambient temperature. The precipitate is rinsed with 5 N aqueous hydrochloric acid solution and toluene. After drying in vacuo, the title product is obtained in the form of a cream solid, which is used in the following step without being purified.

$^1$H NMR (400 MHz, dmso-d6, 300 K) δ ppm: 12.75 (s, 1H), 7.98 (d, 1H), 7.48 (d, 1H), 7.3 (t, 1H), 7.15 (d, 1H), 4.2 (m, 1H), 3.8 (s, 3H), 3.28/3.05 (m, 2H).

IR: ν: —NH/OH: 3215 and 3000 to 2000; >C=O: 1715 and 1627 cm$^{-1}$.

Step E: 5-Methoxy-3-(morpholin-4-ylcarbonyl)-3,4-dihydroisoquinolin-1(2H)-one

To a solution of the compound obtained in Step D (11.1 g; 50 mmol) in dichloromethane (150 mL) there are added in succession morpholine (4.4 mL; 50 mmol), 1-hydroxybenzotriazole (6.7 g; 50 mmol), 1-(3-dimethylaminopropyl)-3-ethylcarbodiimide hydrochloride (9.6 g; 50 mmol) and diisopropylethylamine (20 mL; 115.2 mmol). The whole is then stirred overnight at ambient temperature. The reaction mixture is diluted with a mixture of dichloromethane and water. After decantation, the organic phase is washed with saturated aqueous ammonium chloride solution and saturated aqueous sodium chloride solution and then dried over magnesium sulphate, filtered and concentrated to dryness. The residue is taken up in dichloromethane, filtered and rinsed with hot isopropanol to obtain the title product, which is used in the following step without being purified.

$^1$H NMR (400 MHz, dmso-d6, 300 K) δ ppm: 7.71 (d, 1H), 7.45 (d, 1H), 7.29 (t, 1H), 7.11 (d, 1H), 4.7 (m, 1H), 3.81 (s, 3H), 3.65-3.3 (unresolved peak, 8H), 3.05/2.95 (2*dd, 2H).

IR: ν: —NH: 3284; >C=O: 1676; >C—O—C<: 1268 and 1248 cm$^{-1}$.

Step F: 5-Methoxy-3-(morpholin-4-ylmethyl)-1,2,3,4-tetrahydroisoquinoline

A 2 M solution of borane/dimethyl sulphide complex in tetrahydrofuran (43 mL; 86 mmol) is added dropwise to a solution of the compound obtained in Step E (5 g; 17.2 mmol) in tetrahydrofuran (300 mL). The whole is then stirred at reflux for 5 hours and then at ambient temperature overnight. 5 N aqueous hydrochloric acid solution is added dropwise, and the reaction mixture is heated at reflux for 8 hours. Finally, aqueous sodium hydroxide solution is added at 0° C. until a basic pH is reached, and the reaction mixture is diluted with dichloromethane. After extraction, the organic phases are washed with water and then dried over magnesium sulphate, filtered and concentrated to dryness. The residue is purified by chromatography over silica gel using dichloromethane and ammonia in ethanol as eluants to obtain the title product.

$^1$H NMR (400 MHz, dmso-d6, 300 K) δ ppm: 7.61 (d, 1H), 7.09 (t, 1H), 6.72 (d, 1H), 3.9 (s, 2H), 3.75 (s, 3H), 3.6 (t, 4H), 2.9 (m, 1H), 2.62/2.05 (2dd, 2H), 2.5-2.3 (m, 6H).

IR: ν: —NH: 3203 cm$^{-1}$.

Step G: 3-(Morpholin-4-ylmethyl)-1,2,3,4-tetrahydroisoquinolin-5-ol

A 1 M solution of tribromoborane in dichloromethane (100 mL; 100 mmol) is added dropwise at a temperature of −10° C. to a solution of the compound obtained in Step F (5.6 g; 21 mmol) in dichloromethane (60 mL). The whole is then stirred at that temperature for 3 hours and then heated to 10° C. again in 1 hour. The reaction mixture is diluted at 0° C. with dichloromethane and saturated aqueous sodium hydrogen carbonate solution and then filtered to obtain a white solid. After decantation, the aqueous phase is extracted with ethyl acetate and then the organic phases are concentrated. The residue obtained as well as the white precipitate are combined to obtain the title product, which is used in the following step without being purified.

$^1$H NMR (400 MHz, dmso-d6, 300 K) δ ppm: 9.2 (br. s, 1H), 6.89 (t, 1H), 6.59 (d, 1H), 6.48 (d, 1H), 3.81 (s, 2H), 3.6 (t, 4H), 2.89 (m, 1H), 2.6/2.02 (2dd, 2H), 2.5-2.25 (m, 6H).

IR: ν: —NH/OH: 3412 and 3000 to 2500; >C=C<: 1615 cm$^{-1}$.

Step H: tert-Butyl 5-hydroxy-3-(morpholin-4-ylmethyl)-3,4-dihydroisoquinoline-2(1H)-carboxylate To a solution of the compound obtained in Step G (4.1 g; 16.5 mmol) in dichloromethane (100 mL) there are added diisopropylethylamine (7.4 mL; 72.6 mmol) and di-ten-butyl dicarbonate (7.9 g, 36.3 mmol), and then the whole is stirred for 18 hours at ambient temperature. The reaction mixture is diluted with saturated aqueous ammonium chloride solution. After decantation, the organic phase is washed with saturated aqueous sodium hydrogen carbonate solution and saturated aqueous sodium chloride solution and then dried over magnesium sulphate, filtered and concentrated to dryness. The residue is diluted in a 1 M solution of potassium hydroxide in methanol. After 2 hours' contact at ambient temperature, the reaction mixture is diluted with dichloromethane and saturated aqueous ammonium chloride solution. After extraction with dichloromethane, the organic phases are washed with water, dried over magnesium sulphate, filtered and concentrated. The residue is purified by chromatography over silica gel using dichloromethane and methanol as eluants to obtain the title product.

$^1$H NMR (400 MHz, dmso-d6, 300 K) δ ppm: 9.41 (br. s, 1H), 6.97 (t, 1H), 6.62 (d, 1H), 6.55 (d, 1H), 4.7-4.4 (d+m, 2H), 4.08 (m, 1H), 3.52 (m, 4H), 2.75-2.2 (m, 7H), 2.08 (dd, 1H), 1.42 (br. s, 9H).

IR: ν: —OH: 3295; >C=O: 1689 and 1656 cm$^{-1}$.

Preparation 5b': tert-Butyl 4-(2-hydroxyethyl)-3,4-dihydroisoquinoline-2(1H)-carboxylate Step A: 4-(Prop-2-en-1-yl)isoquinoline A solution of 4-bromoisoquinoline (25 g; 0.12 mol) and potassium carbonate (50 g; 0.36 mol) in a mixture of water (125 mL) and dimethoxyethane (375 mL) is degassed by means of a stream of nitrogen. Tetrakis(triphenylphosphine) palladium(0) (7 g; 0.006 mol) and allylboronic pinacolate (35 mL; 0.18 mol) are then added. Nitrogen is bubbled through the mixture for 30 minutes, and then the mixture is brought to reflux and stirred for 18 hours. After returning to ambient temperature, the reaction mixture is hydrolysed. The product is extracted with ethyl acetate and then the organic phases are washed with saturated aqueous sodium chloride solution, dried over magnesium sulphate, filtered and concentrated to dryness. The residue is purified by chromatography over silica gel using heptane and ethyl acetate as eluants to obtain the title product.

$^1$H NMR (400 MHz, CDCl$_3$, 300 K) δ ppm: 9.15 (s, 1H), 8.39 (s, 1H), 7.98 (d, 2H), 7.71 (ddd, 1H), 7.60 (ddd, 1H), 6.08 (dddd, 1H), 5.05-5.15 (m, 2H), 3.78 (d, 2H).

Step B: 2-(Isoquinolin-4-yl)ethanol

The compound obtained in Step A (14 g; 78 mmol) is dissolved in a mixture of dichloromethane (180 mL) and methanol (180 mL). There are bubbled through the solution so obtained ozone by means of a gas diffuser at −78° C. for 1.5 hours, then air for 10 minutes and finally nitrogen for the same time. The reaction mixture is maintained at 0° C., and sodium borohydride (8.83 g; 233 mmol) is added in portions. After a contact time of 18 hours at ambient temperature, the mixture is diluted in a mixture of water and saturated aqueous ammonium chloride solution. The product is extracted with ethyl acetate and then the organic phases are washed with saturated aqueous sodium chloride solution, dried over magnesium sulphate, filtered and concentrated to dryness. The residue is purified by chromatography over silica gel using ethyl acetate and methanol as eluants to obtain the title product.

$^1$H NMR (400 MHz, CDCl$_3$, 300 K) δ ppm: 9.00 (s, 1H), 8.37 (s, 1H), 8.03 (d, 1H), 7.92 (d, 1H), 7.74 (ddd, 1H), 7.61 (ddd, 1H), 4.01 (t, 2H), 3.29 (t, 2H), 2.35 (s, 1H).

Step C: tert-Butyl 4-(2-hydroxyethyl)-3,4-dihydroisoquinoline-2(1H)-carboxylate

The title compound is obtained in accordance with the process described in Step B of Preparation 1b' using the compound of the preceding step as the starting material.

$^1$H NMR (400 MHz, CDCl$_3$, 300 K) δ ppm: 7.16-7.22 (m, 3H), 7.07-7.13 (m, 1H), 4.87 (d, 1H), 4.32 (d, 1H), 4.19 (s, 1H), 3.73-3.87 (m, 2H), 3.19 (d, 1H), 2.97-3.04 (m, 1H), 1.81 (q, 2H), 1.65 (s, 1H), 1.50 (s, 9H).

Preparation 6b': tert-Butyl 4-hydroxy-1,3-dihydro-2H-isoindole-2-carboxylate

Step A: Furan-2-yl 2,2-dimethylpropanoate

A solution of triethylamine (43.5 mL; 0.31 mol) in acetonitrile (11 mL) is added to a solution of 2-(5H)-furanone (22 g; 0.26 mol) and trimethylacetyl chloride (38 g; 0.31 mol) in acetonitrile (50 mL). The reaction mixture is stirred for 3 days at ambient temperature, and then the resulting suspension is filtered and rinsed with methyl tert-butyl ether. The organic phase is washed with saturated aqueous sodium bicarbonate solution and saturated aqueous sodium chloride solution and then dried over magnesium sulphate, filtered and concentrated in vacuo. The resulting oil is distilled in vacuo (15 Torr, fractions collected at 76-78° C.) to obtain the title product.

$^1$H NMR (400 MHz, CDCl$_3$, 300 K) δ ppm: 7.05 (dd, 1H), 6.36 (dd, 1H), 5.86 (dd, 1H), 1.34 (s, 9H).

Step B: 1,3-Dioxo-3,3a,7,7a-tetrahydro-4,7-epoxy-2-benzofuran-4(1H)-yl 2,2-dimethyl-propanoate The compound obtained in Step A (38.76 g; 0.23 mol) is added to a solution of maleic anhydride (24.9 g; 0.25 mol), freshly ground in a mortar, in diethyl ether (207 mL). The reaction mixture is stirred at ambient temperature for 16 hours. The resulting beige suspension is filtered and the filtrate is concentrated to approximately 50 mL and then filtered again. The solids so obtained are combined and dried in vacuo to give the title product.

$^1$H NMR (400 MHz, dmso-d6, 300 K) δ ppm: 6.77 (dd, 1H), 6.69 (d, 1H), 5.33 (d, 1H), 3.66 (s, 2H), 1.22 (s, 9H).

Step C: 4-Hydroxy-2-benzofuran-1,3-dione

The compound obtained in Step B (36.5 g; 0.16 mol) is added in portions to a solution of concentrated sulphuric acid (80 mL) cooled to −15° C. The mixture is stirred for 15 minutes at −15° C. and then poured into ice-water. The solid formed is then filtered off, rinsed with water and dried to give the title product.

$^1$H NMR (400 MHz, dmso-d6, 300 K) δ ppm: 11.72 (s, 1H), 7.77 (dd, 1H), 7.45 (d, 1H), 7.33 (d, 1H).

Step D: 4-Hydroxy-2-(4-methoxybenzyl)-1H-isoindole-1,3(2H)-dione

4-Methoxybenzylamine (21.7 mL; 0.17 mol) is added to a solution of the compound obtained in Step C (24.76 g; 0.15 mol) in acetic acid (150 mL), and then the mixture is heated at reflux for 5 hours. After returning to ambient temperature, water (200 mL) is added to the mixture, which is stirred for 1 hour. The suspension is filtered and the solid is rinsed with water. The crude product is dissolved in ethyl acetate and the organic phase is washed with saturated aqueous sodium bicarbonate solution, saturated aqueous ammonium chloride solution and finally with saturated aqueous sodium chloride solution, dried over sodium sulphate, filtered and concentrated in vacuo to give the title product.

$^1$H NMR (400 MHz, CDCl$_3$, 300 K) δ ppm: 7.54 (t, 1H), 7.32-7.40 (m, 3H), 7.12 (d, 1H), 6.84 (d, 2H), 4.73 (s, 2H), 3.77 (s, 3H).

Step E: 2-(4-Methoxybenzyl)-2,3-dihydro-1H-isoindol-4-ol

A solution of the compound obtained in Step D (35.5 g; 0.13 mol) in tetrahydrofuran (250 mL) is added dropwise, while maintaining the internal temperature of the mixture below 20° C., to a suspension of lithium aluminium hydride (11.9 g; 0.31 mol) in tetrahydrofuran (150 mL) at 0° C. Once the addition is complete, the mixture is heated to reflux. The mixture is stirred at reflux for 2 hours and then cooled to 0° C. Ethyl acetate is added slowly, while maintaining the internal temperature of the mixture below 20° C. When an exothermic effect is no longer observed during the addition of ethyl acetate, the mixture is diluted with ethyl acetate and 1.5 N aqueous Rochelle salt solution. The mixture is stirred vigorously for 2 hours at ambient temperature. After decantation, the aqueous phase is washed with ethyl acetate. The organic phases are combined and washed with saturated aqueous sodium chloride solution, dried over magnesium sulphate, filtered and concentrated in vacuo to give the title product.

$^1$H NMR (400 MHz, CDCl$_3$, 300 K) δ ppm: 7.27-7.34 (m, 2H), 6.95 (t, 1H), 6.81-6.90 (m, 2H), 6.68 (d, 1H), 6.39 (d, 1 II), 3.89 (d, 4H), 3.83 (s, 2H), 3.80 (s, 3H).

Step F: tert-Butyl 4-hydroxy-1,3-dihydro-2H-isoindole-2-carboxylate

Palladium on carbon (10% by mass) is added to a solution of the compound obtained in Step E (18.2 g; 71.3 mmol) in methanol (325 mL) and acetic acid (8.2 mL). The reactor is sealed and purged with nitrogen and then with hydrogen. The reaction mixture is subjected to a hydrogen pressure of 45 psi and stirred for 4 hours at ambient temperature. The reaction mixture is filtered and rinsed with methanol, and then the filtrate is concentrated in vacuo. To a solution of the crude product in methanol (200 mL) there are added triethylamine (40 mL; 0.29 mol) and di-tert-butyl dicarbonate (15.6 g; 71.3 mmol). The mixture is stirred at ambient temperature for 16 hours. The solvent is evaporated off in vacuo and the residue is diluted in ethyl acetate. The organic phase is washed with 2 N aqueous hydrochloric acid solution, saturated aqueous sodium bicarbonate solution and with saturated aqueous sodium chloride solution. Then, it is dried over magnesium sulphate, filtered and concentrated in vacuo. The residue is purified by chromatography over silica gel using heptane and ethyl acetate as eluants to obtain the title product.

$^1$H NMR (400 MHz, CDCl$_3$, 300 K) δ ppm: 7.11-7.17 (m, 1H), 7.02 (s, 0.5H), 6.68-6.84 (m, 2H), 5.98 (s, 0.5H), 4.63-4.85 (m, 4H), 1.51-1.55 (in, 9H).

Preparation 7b': tert-Butyl 5-hydroxy-3-methyl-3,4-dihydroisoquinoline-2(1H)-carboxylate

Step A: 3-(Benzyloxy)-2-(prop-2-en-1-yl)benzaldehyde

To a solution of 2-allyl-3-hydroxy-benzaldehyde (20 g; 0.12 mol) in acetonitrile (400 mL) there are added benzyl bromide (16 mL; 0.13 mol) and potassium carbonate (18 g; 0.13 mol). The reaction mixture is stirred for 3 days at ambient temperature and then poured into a mixture of ice and saturated aqueous sodium hydrogen carbonate solution. After extraction with ethyl acetate, the organic phases are dried over magnesium sulphate, filtered and concentrated in vacuo. The residue is purified by chromatography over silica gel using dichloromethane as eluant to obtain the title product.

$^1$H NMR (400 MHz, dmso-d6, 300 K) δ ppm: 10.2 (s, 1H), 7.5-7.3 (m, 8H), 6 (ddt, 1H), 5.2 (s, 2H), 5-4.85 (m, 2H), 3.85 (dt, 2H).

IR: ν: >C=O: 1681 cm$^{-1}$.

Step B: N-Benzyl-1-[3-(benzyloxy)-2-(prop-2-en-1-yl)phenyl]methanamine

To a solution of the compound obtained in Step A (20 g; 0.078 mol) in dichloromethane (800 mL) there are added benzylamine (10 mL; 0.078 mol) and, in portions, sodium triacetoxyborohydride (25 g; 0.118 mol). The reaction mixture is stirred for 16 hours at ambient temperature, and then 1 N aqueous sodium hydroxide solution and ice are added. After extraction with dichloromethane, the organic phases are washed with 1 N aqueous sodium hydroxide solution and then with saturated aqueous sodium chloride solution and dried over magnesium sulphate, filtered and concentrated in vacuo. The residue is purified by chromatography over silica gel using dichloromethane and ammonia in ethanol as eluants to obtain the title product.

$^1$H NMR (400 MHz, dmso-d6, 300 K) δ ppm: 7.48-7.22 (m, 10H), 7.14 (t, 1H), 6.99 (d, 1H), 6.95 (d, t H), 5.85 (m, 1H), 5.09 (s, 2H), 4.85 (m, 1H), 4.76 (m, 1H), 3.7 (s, 2H), 3.61 (s, 2H), 3.44 (d, 2H), 2.35 (br. s, 1H).

Step C: 2-Benzyl-5-(benzyloxy)-3-methyl-1,2,3,4-tetrahydroisoquinoline 1.5 N n-Butyllithium solution in hexane (4(1 mL; 0.06 mol) is added dropwise at 60° C. to a solution of the compound obtained in Step B (18.9 g; 0.055 mol) in tetrahydrofuran (1 L). At the end of the addition, the reaction mixture is cooled to ambient temperature and then neutralised with water. After extraction with ether, the organic phases are washed with saturated aqueous sodium chloride solution and dried over magnesium sulphate, filtered and concentrated in vacuo. The residue is purified by chromatography over silica gel using heptane and ammonia in ethanol as eluant to obtain the title product.

$^1$H NMR (400 MHz, dmso-d6, 300 K) ppm: 7.5-7.2 (m, 5H), 7.5-7.2 (m, 5H), 7.03 (1, 1H) 6.83 (d, 1H), 6.58 (d, 1H), 5.1 (s, 2H), 3.76 (d, 1H), 3.53 (d, 1H), 3.58 (d, 1H), 3.49 (d, 1H), 3.05 (m, 1H), 2.8 (dd, 1H), 2.49 (dd, 1H), 1.09 (d, 3H).

Step D: 3-Methyl-1,2,3,4-tetrahydroisoquinolin-5-ol

To a solution of the compound obtained in Step C (13.47 g; 39.22 mmol) in methanol (250 mL) there are added 1 N aqueous hydrochloric acid solution (58.8 mL; 58.8 mmol) and then palladium on carbon (10% by mass). The flask is placed under hydrogen pressure and the reaction mixture is stirred for 48 hours at ambient temperature. The reaction mixture is filtered and rinsed with methanol and then the filtrate is concentrated in vacuo. The residue is taken up in ethanol and then filtered to obtain the title product.

$^1$H NMR (400 MHz, dmso-d6, 300 K) δ ppm: 9.75 (s, 1H), 9.3 (br. s, 1H), 7.05 (t, 1H), 6.75 (d, 1H), 6.65 (d, 1H), 4.21 (m, 2H), 3.48 (m, 1H), 2.95 (dd, 1H), 2.47 (dd, 1H), 1.4 (d, 3H).

IR: v: —OH: 3226 cm$^{-1}$; —NH$_2^+$: 3300–3400 cm$^{-1}$.

Step E: tert-Butyl 5-hydroxy-3-methyl-3,4-dihydroisoquinoline-2(1H)-carboxylate To a solution of the compound obtained in Step D (5 g; 25.2 mmol) in dichloromethane (250 mL) there are added at 0° C. triethylamine (7.38 mL; 52.9 mmol) and di-tert-butyl dicarbonate in portions (5.5 g; 25.2 mmol). The reaction mixture is stirred at that temperature for 3 hours and then at ambient temperature for 20 hours. The solvent is evaporated off in vacuo and the residue is diluted in ethyl acetate. The organic phase is washed with saturated aqueous ammonium chloride solution, with water and with saturated aqueous sodium chloride solution and is then dried over magnesium sulphate, filtered and concentrated in vacuo. The residue is purified by chromatography over silica gel using cyclohexane and ethyl acetate as eluants to obtain the title product.

$^1$H NMR (400 MHz, dmso-d6, 300 K) δ ppm: 9.4 (br. s, 1H), 6.98 (t, 1H), 6.67 (d, 1H), 6.6 (d, 1H), 4.59 (d, 1H), 4.15 (d, 1H), 4.45 (m, 1H), 2.65 (d, 2H), 1.42 (s, 9H), 0.99 (d, 3H).

IR: v: —OH: 3308 cm$^{-1}$; >C=O: 1655 cm$^{-1}$.

Preparation 8b': tert-Butyl 5-(3-iodopropoxy)-3,4-dihydroisoquinoline-2(1H)-carboxylate

Step A: tert-Butyl 5-(3-chloropropoxy)-3,4-dihydroisoquinoline-2(1H)-carboxylate To a solution of the compound obtained in Preparation 3b' (1 g; 4 mmol) in acetonitrile (20 mL) there are added bromo-chloropropane (0.48 mL; 4.8 mmol) and potassium carbonate (1.1 g, 8 mmol), and then the whole is stirred for 18 hours at 70° C. The reaction mixture is diluted with ethyl acetate and water. After decantation, the organic phase is washed with water and then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 7.14 (t, 1H), 6.82 (d, 1H), 6.75 (d, 1H), 4.46 (s, 2H), 4.08 (t, 2H), 3.82 (t, 2H), 3.55 (t, 2H), 2.64 (t, 2H), 2.18 (quint, 2H), 1.42 (s, 9H).

IR: v: >C=O: 1692 cm$^{-1}$; >C—O—C<: 1241/1164/1112 cm$^{-1}$.

Step B: tert-Butyl 5-(3-iodopropoxy)-3,4-dihydroisoquinoline-2(1H)-carboxylate Sodium iodide (2.3 g; 15.3 mmol) is added to a solution of the compound obtained in Step A (1 g; 3.07 mmol) in acetone (30 mL), and then the whole is stirred at reflux for 24 hours. The reaction mixture is concentrated and then diluted with ethyl acetate and water. After extraction with ethyl acetate, the organic phases are washed with saturated aqueous sodium chloride solution and then dried over magnesium sulphate, filtered and concentrated to dryness to obtain the title product.

$^1$H NMR (400 MHz, dmso-d6, 300 K) δ ppm: 7.12 (t, 1H), 6.8 (d, 1H), 6.72 (d, 1H), 4.45 (s, 2H), 4 (t, 2H), 3.55 (t, 2H), 3.41 (t, 2H), 2.63 (t, 2H), 2.2 (m, 2H), 1.41 (s, 9H).

IR: v: >C=O: 1692 cm$^{-1}$.

Preparation 9b': tert-Butyl 5-[2-(2-hydroxyethoxy)ethoxy]-3,4-dihydroisoquinoline-2(1H)-carboxylate To a solution of the compound obtained in Preparation 3b' (5 g; 20 mmol) in N,N-dimethylformamide (20 mL) there are added 2-(2-chloroethoxy)ethanol (6.25 mL; 60 mmol) and potassium carbonate (8.3 g, 60 mmol), and then the whole is stirred for 5 hours at 125° C. The reaction mixture is diluted with ethyl acetate and water. After decantation, the organic phase is washed with saturated aqueous lithium chloride solution and then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 7.13 (t, 1H), 6.81 (d, 1H), 6.75 (d, 1H), 4.58 (m, 1H), 4.46 (s, 2H), 4.09 (m, 2H), 3.75 (m, 2H), 3.54 (t, 2H), 3.51 (unresolved peak, 4H), 2.63 (t, 2H), 1.42 (s, 9H).

IR: v: —OH: 3450 cm$^{-1}$; >C=O: 1690 cm$^{-1}$.

Preparation 10b': tert-Butyl 5-(but-3-yn-1-yl)-3,4-dihydroisoquinoline-2(1H)-carboxylate

Step A: tert-Butyl 5-(3-methoxy-3-oxopropyl)-3,4-dihydroisoquinoline-2(11-1)-carboxylate Palladium on carbon (10% by mass) is added to a solution of the compound obtained in Step B of Preparation 1b' (19.74 g; 62.3 mmol) in methanol (150 mL). Hydrogen is bubbled through the suspension for 10 minutes, and then the mixture is stirred under a hydrogen atmosphere (I bar) for 18 hours. The reaction mixture is filtered over a bed of Celite® and the filtrate is concentrated to dryness to give the title product, which is used subsequently without being purified.

$^1$H NMR (400 MHz, CDCl$_3$, 300 K) δ ppm: 7.10-7.16 (m, 1H), 7.04 (d, 1H), 6.98 (d, 1H), 4.56 (s, 2H), 3.68 (s, 3H), 3.66 (br. s, 2H), 2.90-2.96 (m, 2H), 2.80 (t, 2H), 2.55-2.61 (m, 2H), 1.48 (s, 9H).

Step B: tert-Butyl 5-(but-3-yn-1-yl)-3,4-dihydroisoquinoline-2(1H)-carboxylate A 25% by mass diisobutylaluminium hydride solution in toluene (25.2 mL, 37.6 mmol) is added slowly, over a period of 45 minutes, to a solution of the product obtained in Step A (10 g; 31.3 mmol) in dichloromethane (100 mL) at −78° C. The rate of addition is determined so as to maintain the temperature of the reaction mixture below −75° C. At the end of the addition, the mixture is stirred at −78° C. for 30 minutes, and then methanol (50 mL) is added slowly to the reaction. The mixture is then heated gradually to 0° C. Methanol (50 mL) is again added, as are potassium carbonate (8.65 g; 62.6 mmol) and then dimethyl-(1-diazo-2-oxopropyl)phosphonate (7.22 g; 37.6 mmol). The mixture is stirred at ambient temperature for 48 hours and is diluted with methyl tert-butyl ether (400 mL). 1 N aqueous potassium sodium tartrate tetrahydrate solution (250 mL) is then added. The phases are separated, and the aqueous phase is washed with methyl tert-butyl ether. The organic phases are combined and washed with saturated aqueous sodium chloride solution, dried over sodium sulphate, filtered and evaporated in vacuo. The residue is purified by chromatography over silica gel using heptane and ethyl acetate as eluants to obtain the title product.

$^1$H NMR (400 MHz, CDCl$_3$, 300 K) δ ppm: 7.12-7.18 (m, 1H), 7.09 (d, 1H), 7.00 (d, 1H), 4.57 (s, 2H), 3.61-3.73 (m, 2H), 2.78-2.89 (m, 4H), 2.44 (td, 2H), 1.98 (t, 114), 1.49 (s, 9H).

Preparation 1b'': tert-Butyl 5-(3-{3-[(4-{[tert-butyl(dimethyl)silyl]oxy}phenyl)amino]-5-cyanophenoxy}propyl)-3,4-dihydroisoquinoline-2(1H)-carboxylate

Step A: tert-Butyl 5-[3-(3-bromo-5-cyanophenoxy)propyl]-3,4-dihydroisoquinoline-2(1H)-carboxylate 60% sodium hydride in oil (1.77 g; 44.1 mmol) is added in portions to a solution of the compound obtained in Preparation 1b' (9.89 g; 34.0 mmol) and 3-bromo-5-fluorobenzonitrile (27.2 g; 135.8 mmol) in N,N-dimethylformamide (80 mL). The whole is then stirred for 45 minutes at ambient temperature and then slowly hydrolysed. After extraction with ethyl acetate, the organic phases are washed with saturated aqueous sodium chloride solution and then dried over magnesium sulphate, filtered and concentrated to dryness. The residue is purified by chromatography over silica gel using heptane and ethyl acetate as eluants to obtain the title product.

$^1$H NMR (400 MHz, CDCl$_3$, 300 K) δ ppm: 7.36 (t, 1H), 7.26-7.28 (m, 1H), 7.12-7.17 (m, 1H), 7.06-7.09 (m, 1H), 6.98-7.05 (m, 2H), 4.58 (s, 2H), 3.98 (t, 2H). 3.62-3.68 (m, 2H), 2.76-2.82 (m, 4H), 2.02-2.09 (m, 2H), 1.49 (s, 9H).

Step B: 4-{[tert-Butyl(dimethyl)silyl]oxy}aniline

The title compound is obtained starting from 4-aminophenol in tetrahydrofuran in the presence of imidazole and tert-butyl(dimethyl)silyl chloride in accordance with the protocol described in the literature (S. Knaggs et al., *Organic & Bimolecular Chemistry*, 3(21), 4002-4010; 2005).

$^1$H NMR (400 MHz, dmso-d6, 300 K) δ ppm: 6.45-6.55 (dd, 4H), 4.60 (m, 2H), 0.90 (s, 9H), 0.10 (s, 6H).

IR: v: —NH$_2$$^+$: 3300–3400 cm$^{-1}$

Step C': tert-Butyl 5-(3-{3-[(4-{[tert-butyl(dimethyl)silyl]oxy}phenyl)amino]-5-cyanophenoxy}propyl)-3,4-dihydroisoquinoline-2(1H)-carboxylate A solution of the compounds obtained in Step A (8.11 g; 17.2 mmol) and in Step B (4.23 g; 17.2 mmol) in toluene (110 mL) is degassed with argon for 10 minutes. Sodium tert-butylate (1.82 g; 18.9 mmol), 2-di-tert-butylphosphino-2',4',6'-triisopropyl-1,1'-biphenyl (0.73 g; 1.72 mmol) and tris(dibenzylideneacetone)dipalladium(0) (0.86 g; 0.86 mmol) are added, and then the whole is stirred at 80° C. for 30 minutes. The reaction mixture is filtered over Celite®. After rinsing with ethyl acetate, silica is added to the filtrate and then the mixture is concentrated and purified by chromatography over silica gel using heptane and ethyl acetate as eluants to obtain the title product.

$^1$H NMR (400 MHz, CDCl$_3$, 300 K) δ ppm: 7.13 (t, 1H), 6.95-7.06 (m, 4H), 6.83 (d, 2H), 6.69 (br. s, 1H), 6.51-6.59 (m, 2H), 5.59 (br. s, 1H), 4.57 (s, 2H), 3.92 (t, 2H), 3.58-3.68 (m, 2H), 2.61-2.83 (m, 4H), 2.02 (quint., 2H), 1.49 (s, 9H), 1.00 (s, 9H), 0.21 (s, 6H).

Preparation 2b'': tert-Butyl 5-(4-{4-[(4-{[tert-butyl(dimethyl)silyl]oxy}phenyl)amino]-1H-pyrazol-1-yl}butoxy)-3,4-dihydroisoquinoline-2(1H)-carboxylate

Step A: tert-Butyl 5-[4-(4-bromo-1H-pyrazol-1-yl)butoxy]-3,4-dihydroisoquinoline-2(1H)-carboxylate A solution of 4-bromopyrazole (0.359 mg; 2.44 mmol) and diisopropyl azodicarboxylate (0.58 mL; 2.93 mmol) in tetrahydrofuran (5 mL) is added dropwise to a solution of the compound of Preparation 2b' (0.786 g; 2.44 mmol) and triphenylphosphine (0.768 mg; 2.93 mmol) in tetrahydrofuran (5 mL). The reaction mixture is stirred at ambient temperature for 2 hours and then diluted in a mixture of ethyl acetate and water. After extraction of the aqueous phase with ethyl acetate, the organic phases are combined, washed with saturated aqueous ammonium chloride solution, saturated aqueous sodium chloride solution and then dried over magnesium sulphate, filtered and concentrated to dryness. The residue is purified by chromatography over Oasis® phase using acetonitrile and water as eluants to obtain the title product.

$^1$H NMR (400 MHz, dmso-d6, 300 K) δ ppm: 8.02 (s, 1H), 7.53 (s, 1H), 7.12 (dd, 1H), 6.81-6.68 (2*d, 2H), 4.46

(s, 2H), 4.16 (t, 2H), 3.95 (t, 2H), 3.54 (t, 2H), 2.61 (t, 2H), 1.93 (m, 2H), 1.65 (m, 2H), 1.41 (s, 9H).
IR: ν: >C=O: 1688 cm$^{-1}$.

Step B: tert-Butyl 5-(4-{[(4-{[tert-butyl(dimethyl) silyl]oxy}phenyl)amino]-1H-pyrazol-1-yl}butoxy)-3,4-dihydroisoquinoline-2(1H)-carboxylate The title compound is obtained in accordance with the process described in Step C of Preparation 1b" using the compound obtained in the preceding step, the compound of Step B of Preparation 1b" and chloro(2-di-tert-butylphosphino-2',4',6'-triisopropyl-1,1'-biphenyl)[2-(2-aminoethyl) phenyl]palladium(II) as catalyst and ligand.
$^1$H NMR (400 MHz, dmso-d6, 300 K) δ ppm: 7.63 (d, 1H), 7.26 (d, 1H), 7.2 (s, 1H), 7.11 (t, 1H), 6.75 (dd, 2H), 6.64 (m, 4H), 4.45 (s, 2H), 4.1 (t, 2H), 3.96 (t, 2H), 3.53 (t, 2H), 2.62 (t, 2H), 1.93 (m, 2H), 1.68 (m, 2H), 1.41 (s, 9H), 0.93 (s, 9H), 0.12 (s, 6H).
IR: ν: —NH: 3340 cm$^{-1}$; >C=O: 1690 cm$^{-1}$.

Preparation 3b": tert-Butyl 5-(2-{4-[(4-{[tert-butyl (dimethyl)silyl]oxy}phenyl)amino]-1-methyl-1H-pyrazol-5-yl}ethoxy)-3,4-dihydroisoquinoline-2 (1H)-carboxylate Step A: 5-(2-{[tert-Butyl(dimethyl)silyl]oxy}ethyl)-1-methyl-1H-pyrazole A solution of n-butyllithium in hexane (100 mL; 160 mmol) is added dropwise at −78° C. to a solution of N-methylpyrazole (10.95 g; 133 mmol) in tetrahydrofuran (200 mL), and then the temperature is increased to 0° C. again in 1 hour. The reaction mixture is again cooled to −78° C., and a solution of (3-bromoethoxy)-tert-butyldimethylsilane (34.2 mL; 160 mmol) in tetrahydrofuran (50 mL) is added. The reaction mixture is then stirred at ambient temperature for 18 hours and poured into a mixture of ice-water and ethyl acetate. After extraction with ethyl acetate, the organic phase is washed with saturated aqueous sodium chloride solution and then dried over magnesium sulphate, filtered and concentrated to dryness. The residue is purified by chromatography over silica gel using heptane and ethyl acetate as eluants to obtain the title product.
$^1$H NMR (400 MHz, dmso-d6, 300 K) δ ppm: 7.28 (d, 1H), 6.04 (d, 1H), 3.79 (t, 2H), 3.74 (s, 3H), 2.81 (t, 2H), 0.84 (s, 9H), 0.1 (s, 6H).

Step B: 2-(4-Bromo-1-methyl-1H-pyrazol-5-yl)ethanol

Pyridinium tribromide (14 g; 43 mmol) is added at 0° C. to a solution of the compound obtained in Step A (9.8 g; 41.1 mmol) in methanol (400 mL), and then the whole is stirred for 1 hour at 0° C. and then for 2 hours at ambient temperature. The reaction mixture is then concentrated and the residue is taken up in a mixture of saturated aqueous 10% potassium carbonate solution and dichloromethane. After extraction with dichloromethane, the organic phase is washed with saturated aqueous sodium chloride solution and then dried over magnesium sulphate, filtered and concentrated to dryness. The residue is purified by chromatography over silica gel using dichloromethane and ammonia in methanol as eluants to obtain the title product.
$^1$H NMR (400 MHz, dmso-d6, 300 K) δ ppm: 7.45 (s, 1H), 4.88 (t, 1H), 3.81 (s, 3H), 3.55 (q, 2H), 2.8 (t, 2H).

IR: ν: —OH: 3350 cm$^{-1}$; >C—C—O—: 1049 cm$^{-1}$.

Step tert-Butyl 5-[2-(4-bromo-1-methyl-1H-pyrazol-5-yl)ethoxy]-3,4-dihydroiso-quinoline-2(1H)-carboxylate The title compound is obtained in accordance with the process described in Step A of Preparation 2b" using the alcohol obtained in the preceding step and the compound of Preparation 3b'.
$^1$H NMR (400 MHz, dmso-d6, 300 K) δ ppm: 7.49 (s, 1H), 7.13 (t, 1H), 6.82 (d, 1H), 6.75 (d, 1H), 4.45 (s, 2H), 4.15 (t, 2H), 3.87 (s, 3H), 3.51 (t, 2H), 3.16 (t, 2H), 2.54 (t, 2H), 1.41 (s, 9H).
IR: ν: >C=O: 1689 cm$^{-1}$.

Step D: tert-Butyl 5-(2-{4-[(4-{[tert-butyl(dimethyl) silyl]oxy}phenyl)amino]-1-methyl-1H-pyrazol-5-yl}ethoxy)-3,4-dihydroisoquinoline-2(1H)-carboxylate The title compound is obtained in accordance with the process described in Step C of Preparation 1 b" using the compound obtained in the preceding step, the compound of Step B of Preparation 1b" and chloro(2-di-tert-butylphosphino-2',4',6'-triisopropyl-1,1'-biphenyl)[2-(2-aminoethyl) phenyl]palladium(II) as catalyst and ligand.
$^1$H NMR (400 MHz, dmso-d6, 300 K) δ ppm: 7.28 (s, 1H), 7.06 (t, 1H), 6.71/6.67 (2*dd, 2H), 6.7 (s, 1H), 6.57 (d, 2H), 6.48 (d, 2H), 4.43 (s, 2H), 4.05 (t, 2H), 3.82 (s, 3H), 3.48 (t, 2H), 3.03 (t, 2H), 2.5 (t, 2H), 1.4 (s, 9H), 0.9 (s, 9H), 0.09 (s, 6H).
IR: ν: >NH: 3321 cm'; >C=O: 1677 cm$^{-1}$.

Preparation 4b": N-(4-{[tert-Butyl(dimethyl)silyl] oxy}phenyl)-1-methyl-5-[3-(tetrahydro-2H-pyran-2-yloxy)propyl]-1H-pyrazol-4-amine Step A: 5-(3-{[tert-Butyl(dimethyl)silyl] oxy}propyl)-1-methyl-1H-pyrazole The title compound is obtained in accordance with the process described in Step A of Preparation 3b" using (3-bromopropoxy)-tert-butyldimethylsilane.
$^1$H NMR (400/500 MHz, CDCl$_3$, 300 K) δ ppm: 7.35 (d, 1H), 7 (d, 1H), 3.8 (s, 3H), 3.65 (t, 2H), 2.7 (m, 2H), 1.85 (m, 2H), 0.9 (s, 9H), 0.5 (s, 6H).
IR: ν: —Si—O—: 1098 cm$^{-1}$; —Si—C—: 834 and 772 cm$^{-1}$.

Step B: 3-(4-Bromo-1-methyl-1H-pyrazol-5-yl)propan-1-ol

The title compound is obtained in accordance with the process described in Step B of Preparation 3b" using the compound of the preceding step.
$^1$H NMR (400 MHz, dmso-d6, 300 K) ppm: 7.45 (s, 1H), 4.59 (t, 1H), 3.79 (s, 3H), 3.4 (quad, 2H), 2.7 (t, 2H), 1.65 (m, 2H).
IR: ν: —OH: 3348 cm$^{-1}$.

Step C: 4-Bromo-1-methyl-5-[3-(tetrahydro-2H-pyran-2-yloxy)propyl]-1H-pyrazole

To a solution of the compound obtained in Step B (5.34 g; 2.4 mmol) in dichloromethane (40 mL) there are added 3,4-dihydro-2H-pyran (7 mL; 6 mmol) and para-toluenesulphonic acid (4.6 g; 2.4 mmol), and then the whole is stirred for 16 hours. The reaction mixture is diluted in saturated aqueous sodium hydrogen carbonate solution. After extraction with dichloromethane, the organic phase is dried over magnesium sulphate, filtered and concentrated to dryness. The residue is purified by chromatography over silica gel using heptane and ethyl acetate as eluants to obtain the title product.

$^1$H NMR (400 MHz, dmso-d6, 300 K) δ ppm: 7.42 (s, 1H), 4.55 (t, 1H), 3.8-3.3 (m, 4H), 3.8 (s, 3H), 2.71 (m, 2H), 1.78 (m, 2H), 1.7-1.4 (m, 6H).

Step D: N-(4-{[tert-Butyl(dimethyl)silyl]oxy}phenyl)-1-methyl-5-[3-(tetrahydro-2H-pyran-2-yloxy)propyl]-1H-pyrazol-4-amine The title compound is obtained in accordance with the process described in Step D of Preparation 3b" using the compound of the preceding step.

$^1$H NMR (500 MHz, dmso-d6, 300 K) δ ppm: 7.2 (s, 1H), 6.6 (s, 1H), 6.55 (d, 2H), 6.45 (d, 2H), 4.4 (t, 1H), 3.7 (s, 3H), 3.65-3.2 (4m, 4H), 2.58 (m, 2H), 1.68 (m, 2H), 1.6-1.3 (m, 6H), 0.92 (s, 9H), 0.1 (s, 6H).

IR: v: >NH: 3356 cm$^{-1}$; ->C—C—O—: 1240 cm$^{-1}$.

Preparation 5b": tert-Butyl 5-(3-{3-[(4-{[tert-butyl(dimethyl)silyl]oxy}phenyl)amino]-5-cyano-1-methyl-1H-pyrrol-2-yl}propoxy)-3,4-dihydroisoquinoline-2(1H)-carboxylate Step A: Ethyl (2E)-3-(1-methyl-1H-pyrrol-2-yl)prop-2-enoate Potassium tert-butoxide (9.25 g; 82.5 mmol) is added to a solution of triethyl phosphonoacetate (14.2 mL; 71.5 mmol) in tetrahydrofuran (300 mL), and then the whole is stirred at 0° C. for 45 minutes. A solution of N-methyl-2-pyrrolecarboxaldehyde (6 g; 55.0 mmol) in tetrahydrofuran (20 mL) is added and the whole is stirred at ambient temperature for 16 hours, and then the solvent is concentrated. The residue is diluted in water and ethyl acetate. After extraction with ethyl acetate, the organic phase is washed with saturated aqueous sodium chloride solution, dried over sodium sulphate, filtered and concentrated to dryness. The residue is purified by chromatography over silica gel using heptane and ethyl acetate as eluants to obtain the title product.

$^1$H NMR (400 MHz, CDCl$_3$, 300 K) δ ppm: 7.59 (d, 1H), 6.73-6.76 (m, 1H), 6.65 (dd, H), 6.11-6.18 (m, 2H), 4.23 (q, 2H), 3.71 (s, 3H), 1.32 (t, 3H).

Step B: Ethyl 3-(1-methyl-1H-pyrrol-2-yl)propanoate

Palladium on carbon (10% by mass) is added to a solution of the compound obtained in Step A (8.1 g; 45.1 mmol) in ethanol (70 mL), and then the whole is hydrogenated for 6 hours and 30 minutes. The reaction mixture is filtered over Celite® and the filtrate is concentrated to obtain the title product, which is used subsequently without being purified.

$^1$H NMR (400 MHz, CDCl$_3$, 300 K) δ ppm: 6.52-6.56 (m, 1H), 6.01-6.06 (m, 1H), 5.87 (ddt, 1H), 4.15 (q, 2H), 3.55 (s, 3H), 2.83-2.91 (m, 2H), 2.60-2.68 (m, 2H), 1.26 (t, 3H).

Step C: Ethyl 3-(5-cyano-1-methyl-1H-pyrrol-2-yl)propanoate

To a solution of the compound obtained in Step B (12 g; 66.2 mmol) in acetonitrile (300 mL) at −20° C. there is added dropwise, while maintaining that temperature, chlorosulphonyl isocyanate (6.92 mL; 79.5 mmol), and then the whole is stirred at −20° C. for 30 minutes. N,N-Dimethylformamide (10.3 mL; 132.4 mmol) and then triethylamine (18.5 mL; 132.4 mmol) are added at a temperature maintained at −10° C., and the whole is stirred until it reaches ambient temperature. The reaction mixture is diluted in 1 M aqueous hydrochloric acid solution (500 mL). After extraction with ethyl acetate, the organic phase is washed with 1 M aqueous hydrochloric acid solution and then with saturated aqueous sodium chloride solution, dried over sodium sulphate, filtered and concentrated to dryness. The residue is purified by chromatography over silica gel using heptane and ethyl acetate as eluants to obtain the title product.

$^1$H NMR (400 MHz, CDCl$_3$, 300 K) δ ppm: 6.72 (d, 1H), 5.93 (d, 1H), 4.15 (q, 2H), 3.68 (s, 3H), 2.86-2.93 (m, 2H), 2.63-2.69 (m, 2H), 1.26 (t, 3H).

Step D: 4-Bromo-5-(3-hydroxypropyl)-1-methyl-1H-pyrrole-2-carbonitrile

N-Bromosuccinimide (8.82 g; 49.6 mmol) is added in portions to a solution of the compound obtained in Step C (9.74 g; 47.2 mmol) in N,N-dimethylformamide (125 mL) at 0° C., and then the whole is stirred at ambient temperature for 30 minutes. The reaction mixture is diluted in water and tert-butyl methyl ether. After extraction with tert-butyl methyl ether, the organic phase is washed with water and saturated aqueous sodium chloride solution, dried over sodium sulphate, filtered and concentrated to dryness to obtain the product, which is used directly in the following step.

To a solution of that compound (3.13 g; 10.97 mmol) in tetrahydrofuran (30 mL) at 0° C. there is added 2 M lithium borohydride solution in tetrahydrofuran (11 mL; 21.95 mmol), and then the whole is stirred at ambient temperature for 6 hours. The reaction mixture is diluted slowly with 1 M aqueous sodium hydroxide solution (60 mL). After extraction with tart-butyl methyl ether, the organic phase is washed with saturated aqueous sodium chloride solution, dried over sodium sulphate, filtered and concentrated to dryness. The residue is purified by chromatography over silica gel using heptane and ethyl acetate as eluants to obtain the title product.

$^1$H NMR (400 MHz, CDCl$_3$, 300 K) δ ppm: 6.75 (s, 1H), 3.73 (s, 3H), 3.62-3.69 (m, 2H), 2.78 (t, 2H), 1.75-1.85 (m, 2H), 1.38-1.45 (m, 1H).

Step E: tert-Butyl 5-[3-(3-bromo-5-cyano-1-methyl-1H-pyrrol-2-yl) propoxy]-3,4-dihydro-isoquinoline-2(1H)-carboxylate The title compound is obtained in accordance with the process described in Step A of Preparation 2b" using the alcohol obtained in the preceding step and the compound of Preparation 3b'.

$^1$H NMR (400 MHz, dmso-d6, 300 K) δ ppm: 7.11 (t, 1H), 7.06 (s, 1H), 6.75 (2d, 2H), 4.49 (s, 2H), 3.99 (t, 2H), 3.7 (s, 3H), 3.55 (t, 2H), 2.88 (t, 2H), 2.61 (t, 2H), 1.98 (m, 2H), 1.41 (s, 9H).

IR: v: >CN: 2218 cm$^{-1}$; ->C=O: 1681 cm$^{-1}$.

Step F: tert-Butyl 5-(3-{3-[(4-{[tert-butyl(dimethyl)silyl]oxy}phenyl)amino]-5-cyano-1-methyl-1H-pyrrol-2-yl}propoxy)-3,4-dihydroisoquinoline-2(1H)-carboxylate The title compound is obtained in accordance with the process described in Step D of Preparation 3b" using the compound of the preceding step.

¹H NMR (400 MHz, dmso-d6, 300 K) δ ppm: 7.05 (t, 1H), 6.75 (s, 1H), 6.75 (s, 1H), 6.7/6.6 (2d, 2H), 6.52 (d, 2H), 6.45 (d, 2H), 4.42 (s, 2H), 3.88 (t, 2H), 3.68 (s, 3H), 3.5 (t, 2H), 2.75 (t, 2H), 2.51 (t, 2H), 1.89 (m, 2H), 1.41 (s, 9H), 0.9 (s, 9H), 0.1 (s, 6H).

IR: v: >NH: 3364 cm$^{-1}$; >CN: 2208 cm$^{-1}$; >C=O: 1690 cm$^{-1}$.

Preparation 6b": tert-Butyl 5-(2-{3-[(4-{[tert-butyl (dimethyl)silyl]oxy}phenyl)amino]-5-cyano-1-methyl-1H-pyrrol-2-yl}ethoxy)-3,4-dihydroisoquinoline-2(1H)-carboxylate Step A: (1-Methyl-1H-pyrrol-2-yl)(oxo)acetic acid N-Methylpyrrole (20 g; 0.25 mol) is added to a solution of oxalyl chloride (20.9 g; 0.25 mol) in dichloromethane at −10° C., a temperature below 0° C. being maintained, and then the whole is stirred at 0° C. for 1 hour. The reaction mixture is diluted in 25% aqueous potassium hydroxide solution at 0° C. After decantation, the aqueous phase is washed with dichloromethane and acidified to pH=1 with 20% aqueous sulphuric acid solution. The precipitate is filtered and dried to obtain the title product.

¹H NMR (400 MHz, CDCl₃, 300 K) δ ppm: 8.01 (dd, 1H), 7.10 (t, 1H), 6.27 (dd, 1H), 3.99 (s, 3H).

Step B: (1-Methyl-1H-pyrrol-2-yl)acetic acid

The compound obtained in Step A (29 g; 0.19 mol) is added to 65% aqueous hydrazine monohydrate solution (15.5 mL; 0.21 mol), and then the whole is stirred for a few minutes. 20% aqueous sodium hydroxide solution (326 mL) is added slowly and the whole is stirred at reflux for 4 hours. After returning to ambient temperature, 6 N aqueous hydrochloric acid solution (25 mL) is added. After extraction with dichloromethane, the organic phase is washed with water and saturated aqueous sodium chloride solution, dried over sodium sulphate, filtered and concentrated to a volume of 100 mL. After slowly adding heptane, the precipitate is filtered to obtain the title product.

¹H NMR (400 MHz, CDCl₃, 300 K) δ ppm: 6.60-6.64 (m, 1H), 6.04-6.12 (m, 2H), 3.68 (s, 2H), 3.59 (s, 3H).

Step C: Methyl (1-methyl-1H-pyrrol-2-yl)acetate

Dimethyl sulphate (7 mL; 73.4 mmol) is added to a solution of the compound obtained in Step B (10.2 g; 73.4 mmol) and potassium carbonate (15.2 g; 110.1 mmol) in dichloromethane (100 mL), and then the whole is stirred vigorously at 30° C. for 4 hours. 5% aqueous ammonium hydroxide solution (326 mL) is added. After decantation, the organic phase is washed with 5% aqueous ammonium hydroxide solution and saturated aqueous sodium chloride solution, dried over sodium sulphate, filtered and concentrated to dryness to a volume of 100 mL. After slowly adding heptane, the precipitate is filtered to obtain the title product. The residue is purified by chromatography over silica gel using heptane and ethyl acetate as eluants to obtain the title product.

¹H NMR (400 MHz, CDCl₃, 300 K) δ ppm: 6.58-6.62 (m, 1H), 6.06-6.09 (m, 1H), 6.03-6.06 (m, 1H), 3.71 (s, 3H), 3.64 (s, 2H), 3.58 (s, 3H).

Step D: Methyl (5-cyano-1-methyl-1H-pyrrol-2-yl)acetate

The title compound is obtained in accordance with the process described in Step C of Preparation 5b" using the compound of the preceding step.

¹H NMR (400 MHz, CDCl₃, 300 K) δ ppm: 6.74 (d, 1H), 6.08 (d, 1H), 3.73 (s, 3H), 3.69 (s, 3H), 3.66 (s, 2H).

Step E: 5-(2-Hydroxyethyl)-1-methyl-1H-pyrrole-2-carbonitrile

To a solution of the compound obtained in Step D (11.4 g; 10.97 mmol) in tetrahydrofuran (115 mL) at 0° C. there is added 2 M lithium borohydride solution in tetrahydrofuran (47.7 mL; 95.4 mmol) at a temperature below 5° C., and then the whole is stirred at ambient temperature for 16 hours. The reaction mixture is diluted slowly with saturated aqueous ammonium chloride solution (150 mL). After extraction with tert-butyl methyl ether, the organic phase is washed with saturated aqueous sodium chloride solution, dried over sodium sulphate, filtered and concentrated to dryness. The residue is purified by chromatography over silica gel using heptane and ethyl acetate as eluants to obtain the title product.

¹H NMR (400 MHz, CDCl₃, 300 K) δ ppm: 6.75 (d, 1H), 6.02 (d, 1H), 3.88 (t, 2H), 3.69 (s, 3H), 2.86 (t, 2H).

Step F: 4-Bromo-5-(2-hydroxyethyl)-1-methyl-1H-pyrrole-2-carbonitrile

N-Bromosuccinimide (5.04 g; 28.3 mmol) is added in portions to a solution of the compound obtained in Step E (4.25 g; 28.3 mmol) in N,N-dimethylformamide (43 mL) at 0° C., and then the whole is stirred at ambient temperature for 3 hours. The reaction mixture is diluted in water and tert-butyl methyl ether. After extraction with tert-butyl methyl ether, the organic phase is washed with water and saturated aqueous sodium chloride solution, dried over sodium sulphate, filtered and concentrated to dryness to obtain the title product, which is used subsequently without being purified.

¹H NMR (400 MHz, CDCl₃, 300 K) δ ppm: 6.76 (d, 1H), 3.83 (t, 2H), 3.75 (s, 3H), 2.91 (t, 2H), 1.64 (s, 1H).

Step G: tert-Butyl 5-[2-(3-bromo-5-cyano-1-methyl-M-pyrrol-2-yl)ethoxy]-3,4-dihydro-isoquinoline-2(1H)-carboxylate The title compound is obtained in accordance with the process described in Step A of Preparation 2b" using the alcohol obtained in the preceding step and the compound of Preparation 3b'.

¹H NMR (400 MHz, dmso-d6, 300 K) δ ppm: 7.12 (t, 1H), 7.11 (s, 1H), 6.8 (d, 1H), 6.72 (d, 1H), 4.45 (s, 2H), 4.15 (t, 2H), 3.78 (s, 3H), 3.52 (t, 2H), 3.18 (t, 2H), 2.55 (t, 2H), 1.41 (s, 9H).

IR: v: >CN: 2215 cm$^{-1}$; ->C=O: 1686 cm$^{-1}$.

Step H: tert-Butyl 5-(2-{3-[(4-{[tert-butyl(dimethyl) silyl]oxy}phenyl)amino]-5-cyano-1-methyl-1H-pyrrol-2-yl}ethoxy)-3,4-dihydroisoquinoline-2(1H)-carboxylate The title compound is obtained in accordance with the process described in Step D of Preparation 3b" using the compound of the preceding step.

¹H NMR (400 MHz, dmso-d6, 300 K) δ ppm: 7.05 (t, 1H), 6.82 (s, 1H), 6.78 (s, 1H), 6.7 (2d, 2H), 6.55 (2d, 4H), 4.4 (s, 2H), 4.02 (t, 2H), 3.7 (s, 3H), 3.48 (t, 2H), 3.05 (t, 2H), 2.51 (t, 2H), 1.41 (s, 9H), 0.91 (s, 9H), 0.12 (s, 6H).

IR: v: >NH: 3315 cm-1; >CN: 2212 cm-1; >C—O: 1655 cm-1.

Preparation 7b''': tert-Butyl 5-[2-({4-[(4-{[tert-butyl (dimethyl)silyl]oxy}phenyl)amino]-1-methyl-1H-pyrazol-5-yl}oxy)ethoxy]-3,4-dihydroisoquinoline-2(1H)-carboxylate Step A: tert-Butyl 5-{2-[(4-bromo-1-methyl-1H-pyrazol-5-yl)oxy]ethoxy}-3,4-dihydro-isoquinoline-2(1H)-carboxylate To a solution of the compound obtained in Preparation 3b' (4.06 g; 16.28 mmol) in acetonitrile (75 mL) there are added bromo-chloroethane (2 mL; 24.43 mmol) and potassium carbonate (3.35 g; 24.43 mmol), and then the whole is stirred for 2 days at 70° C. After being concentrated to 2/3, the reaction mixture is diluted with ethyl acetate and water. After extraction with ethyl acetate, the organic phases are washed with saturated aqueous sodium hydrogen carbonate solution, water and then with saturated sodium chloride solution, and dried over magnesium sulphate, filtered and concentrated to dryness. The residue is purified by chromatography over silica gel using dichloromethane as eluant to obtain a colourless oil.

Sodium iodide (21.15 g; 141.1 mmol) is added to a solution of the residue so obtained (4.4 g; 14.1 mmol) in acetone (80 mL), and then the whole is stirred at reflux for 5 days. The reaction mixture is concentrated and then diluted with ethyl acetate and water. After extraction with ethyl acetate, the organic phases are washed with saturated sodium chloride solution and then dried over magnesium sulphate, filtered and concentrated to dryness to obtain a brown oil, which is used in the following step without being purified.

To a solution of the residue so obtained (5.29 g; 13.13 mmol) in acetonitrile (100 mL) there are added 5-hydroxy-N-methylpyrazole (1.29 g; 13.13 mmol), caesium carbonate (4.7 g, 24.43 mmol) and sodium iodide (0.39 g; 2.6 mmol), and then the whole is stirred for 5 hours at 90° C. After concentration of the reaction mixture, the residue is diluted with ethyl acetate and water. After extraction with ethyl acetate, the organic phases are washed with saturated aqueous sodium hydrogen carbonate solution, water, saturated sodium chloride solution, and then dried over magnesium sulphate, filtered and concentrated to dryness. The residue is purified by chromatography over silica gel using heptane and ethyl acetate as eluants to obtain a colourless oil.

Pyridinium tribromide (2.4 g; 7.5 mmol) is added in portions at 0° C. to a solution of the residue so obtained (2.8 g; 7.5 mmol) in methanol (200 mL). The whole is stirred for 1 hour at 0° C. and then for 2 hours at ambient temperature. After concentration of the reaction mixture, the residue is taken up in a mixture of water and dichloromethane. After extraction with dichloromethane, the organic phases are washed with 1 M aqueous hydrochloric acid solution, water, and then dried over sodium sulphate, filtered and concentrated to dryness. The residue is purified by chromatography over RP-18 phase using acetonitrile and water as eluants to obtain the title product.

$^1$H NMR (400 MHz, dmso-d6, 300 K) δ ppm: 7.41 (s, 1H), 7.14 (m, 1H), 6.88 (d, 1H), 6.84 (d, 1H), 4.56/4.28 (2t, 4H), 4.45 (s, 2H), 3.62 (s, 3H), 3.52 (t, 2H), 2.55 (t, 2H), 1.42 (s, 9H).

IR: ν: >C=O: 1689 cm$^{-1}$.

Step B: tert-Butyl 5-[2-({4-[(4-{[tert-butyl(dimethyl)silyl]oxy}phenyl)amino]-1-methyl-1H-pyrazol-5-yl}oxy)ethoxy]-3,4-dihydroisoquinoline-2(1H)-carboxylate A solution of the compound obtained in Step A (2 g; 4.42 mmol) and of the compound obtained in Step B of Preparation 1 b''' (1.48 g; 6.63 mmol) in toluene (15 mL) is degassed with argon for 10 minutes. Sodium tert-butylate (0.51 g; 5.3 mmol), butylphosphino-2',4',6'-triisopropylbiphenyl (0.187 g; 0.44 mmol) and chloro(2-di-tert-butylphosphino-2',4',6'-triisopropyl-1,1'-biphenyl)[2-(2-aminoethyl)phenyl]palladium(II) (0.3 g; 0.44 mmol) are added, and then the whole is stirred 100° C. for 2 hours in a microwave (300 W). The reaction mixture is filtered over Celite®. After rinsing with ethyl acetate, the filtrate is washed with water and saturated aqueous sodium chloride solution and then dried over magnesium sulphate, filtered and concentrated to dryness. The residue is purified by chromatography over silica gel using heptane and ethyl acetate as eluants, then by chromatography over RP-18 phase using acetonitrile and water as eluants to obtain the title product.

$^1$H NMR (400 MHz, dmso-d6, 300 K) δ ppm: 7.18 (s, 1H), 7.1 (m, 1H), 6.75 (d, 2H), 6.7 (s, 1H), 6.6 (d, 2H), 6.48 (d, 2H), 4.45 (s, 2H), 4.42/4.15 (2t, 4H), 3.53 (s, 3H), 3.51 (t, 2H), 2.52 (t, 2H), 1.42 (s, 9H), 0.92 (s, 9H), 0.11 (s, 6H).

IR: ν: >NH: 3485-3182; >C=O: 1689 cm$^{-1}$.

Preparation 8b''': tort-Butyl 4-[2-({4-[(4-{[tert-butyl (dimethyl)silyl]oxy}phenyl)amino]-1-methyl-1H-pyrazol-5-yl}oxy)ethyl]-3,4-dihydroisoquinoline-2(1H)-carboxylate Step A: 5-Chloro-1-methyl-4-nitro-1H-pyrazole To a solution of 1-methyl-4-nitro-1H-pyrazole (5 g; 39.34 mmol) in tetrahydrofuran (50 mL) there are added dropwise at −78° C. 1.3 M lithium bis(trimethylsilyl)amide solution in tetrahydrofuran (82 mL; 106.22 mmol) and hexachloroethane (14 g, 59.01 mmol), and then the whole is stirred for 1 hour at −78° C. The reaction mixture is transferred to saturated aqueous ammonium chloride solution and ice. The product is extracted with dichloromethane and then the organic phases are dried over sodium sulphate, filtered and concentrated to dryness. The residue is purified by chromatography over silica gel using dichloromethane and ethyl acetate as eluants to obtain the title product.

$^1$H NMR (400 MHz, dmso-d6, 300 K) δ ppm: 8.41 (s, 1H), 3.90 (s, 3H).

IR: ν: >CH: 3122; —NO$_2$: 1521+1312 cm$^{-1}$.

Step B: tert-Butyl 4-{2-[(1-methyl-4-nitro-1H-pyrazol-5-yl)oxy]ethyl}-3,4-dihydro-isoquinoline-2(1H)-carboxylate 60% sodium hydride (240 mg; 10.09 mmol) is added to a solution of the compound obtained in Preparation 5b' (2.8 g; 10.09 mmol) in tetrahydrofuran (50 mL), and then the whole is stirred for 1 hour at ambient temperature. A solution of the compound obtained in Step A (1.4 g; 8.66 mmol) in tetrahydrofuran (25 mL) is added and the reaction mixture is stirred for 16 hours and then transferred to saturated aqueous ammonium chloride solution and ice. The product is extracted with ethyl acetate and then the organic phases are dried over sodium sulphate, filtered and concentrated to dryness. The residue is purified by chromatography over silica gel using heptane and ethyl acetate as eluants to obtain the title product.

$^1$H NMR (400 MHz, dmso-d6, 300 K) δ ppm: 8.15 (s, 1H), 7.20 (m, 4H), 4.80 (m, 1H), 4.51 (m, 2H), 4.30 (d, 1H), 4.08 (m, 1H), 3.71 (s, 3H), 3.25 (m, 1H), 3.10 (m, 1H), 2.03 (m, 1H), 1.90 (m, 1H), 1.40 (s, 9H).

IR: ν: >C=O: 1687; —NO$_2$: 1567+1329 cm$^{-1}$.

Step C: tert-Butyl 4-{2-[(4-amino-1-methyl-1H-pyrazol-5-yl)oxy]ethyl}-3,4-dihydro-isoquinoline-2(1H)-carboxylate Palladium on carbon (15% by mass) is added to a solution of the compound obtained in Step B (2.4 g; 5.96 mmol) in methanol (75 mL), and then the whole is hydrogenated for 24 hours at ambient temperature under a pressure of 1 bar. The reaction mixture is filtered and concentrated to dryness. The residue is purified by chromatography over silica gel using dichloromethane and ammonia in ethanol as eluants to obtain the title product.

$^1$H NMR (400 MHz, dmso-d6, 300 K) δ ppm: 7.19 (m, 4H), 6.88 (s, 1H), 4.76 (m, 1H), 4.39-4.21 (m, 3H), 4.01 (dd, 1H), 3.52 (s, 3H), 3.40 (s, 2H), 3.24 (m, 1H), 3.04 (m, 1H), 1.91 (m, 1H), 1.82 (m, 1H), 1.42 (s, 9H).

IR: ν: —NH$_2$ and NH: 3390, 3327 and 3240; >C=O: 1684 cm$^{-1}$.

Step D: tert-Butyl(4-iodophenoxy)dimethylsilane

To a solution of para-iodophenol (20 g; 90 mmol) in dichloromethane (50 mL) there are added triethylamine (15.2 mL; 109 mmol) and tert-butyldimethylchlorosilane chloride (16.4 g; 109 mmol), and then the whole is stirred for 1 hour at ambient temperature. After hydrolysis, the product is extracted with ethyl acetate and then the organic phases are washed with water, saturated aqueous sodium chloride solution, and then dried over magnesium sulphate, filtered and concentrated to dryness. The residue is purified by chromatography over silica gel using petroleum ether and ethyl acetate as eluants to obtain the title product.

$^1$H NMR (400 MHz, CDCl$_3$, 300 K) δ ppm: 7.5 (d, 2H), 6.67 (d, 2H), 0.95 (s, 9H), 0.20 (s, 6H).

IR: ν: >C—O—C<: 1252; —Si—O—C—: 905; —Si—C—: 822 cm$^{-1}$.

Step E: tert-Butyl 4-[2-({4-[(4-{[tert-butyl(dimethyl)silyl]oxy}phenyl)amino]-1-methyl-1H-pyrazol-5-yl}oxy)ethyl]-3,4-dihydroisoquinoline-2(1H)-carboxylate A solution of the compound obtained in Step C (1.05 g; 2.81 mmol) and of the compound obtained in Step D (1.48 g; 3.14 mmol) in toluene (15 mL) is degassed with argon for 10 minutes. Sodium tert-butylate (300 mg; 3.1 mmol) and chloro(2-di-tert-butylphosphino-2',4',6'-triisopropyl-1,1'-biphenyl)[2-(2-aminoethyl)phenyl]palladium(II) (387 mg; 0.56 mmol) are added, and then the whole is stirred at 100° C. for 2.5 hours in a microwave (300 W). The reaction mixture is filtered over Celite®. After rinsing with dichloromethane, the filtrate is concentrated to dryness. The residue is purified by chromatography over silica gel using heptane and ethyl acetate as eluants to obtain the title product.

$^1$H NMR (400 MHz, dmso-d6, 300 K) δ ppm: 7.2-7.20 (m, 5H), 6.60 (d, 2H), 6.5 (d, 2H), 6.4 (s, 1H), 4.65 (d, 1H), 4.25 (d, 1H), 4.20 (m, 2H), 3.60 (s, 3H), 3.30 (dd, 1H), 3.20 (dd, 1H), 2.88 (m, 1H), 1.80 (m, 2H), 1.40 (s, 9H), 0.9 (s, 9H), 0.01 (s, 6H).

IR: ν: >NH: 3328; >C=O: 1693 cm$^{-1}$.

Preparation 9b'': tert-Butyl 5-(2-{4-[(4-{[tert-butyl(dimethyl)silyl]oxy}phenyl)amino]-1-(tetrahydrofuran-3-yl)-1H-pyrazol-5-yl}ethoxy)-3,4-dihydroisoquinoline-2(1H)-carboxylate

Step A: Tetrahydrofuran-3-yl methanesulphonate

Methanesulphonyl chloride (14.6 mL; 0.18 mol) is added to a solution of 3-hydroxytetrahydrofuran (14.8 g; 0.25 mol) and triethylamine (35 mL; 0.25 mol) in dichloromethane (200 mL), and then the whole is stirred at ambient temperature for 16 hours. The reaction mixture is diluted in water. After extraction with dichloromethane, the organic phases are washed with water and then dried over sodium sulphate, filtered and concentrated to dryness to obtain the title product, which is used in the following step without being purified.

$^1$H NMR (400 MHz, CDCl$_3$, 300 K) δ ppm: 5.24-5.32 (m, 1H), 3.81-4.04 (m, 4H), 3.02 (s, 3H), 2.17-2.26 (m, 2H).

Step B: Methyl 1-(tetrahydrofuran-3-yl)-1H-pyrazole-5-carboxylate

Potassium carbonate (33 g; 0.24 mol) is added to a solution of methyl 1H-pyrazole-5-carboxylate (20 g; 0.16 mol) and of the compound obtained in Step A (28.9 g; 0.18 mol) in N,N-dimethylformamide (400 mL), and then the whole is stirred at 80° C. for 48 hours. After returning to ambient temperature, the reaction mixture is filtered and the filtrate is concentrated. The residue is taken up in a 15% mixture of ethyl acetate in heptane and is then filtered over silica gel. The filtrate is concentrated and the residue obtained is purified by chromatography over silica gel using heptane and ethyl acetate as eluants to obtain the title product.

$^1$H NMR (400 MHz, CDCl$_3$, 300 K) δ ppm: 7.50 (d, 1H), 6.83 (d, 1H), 5.85-5.94 (m, 1H), 4.08-4.20 (m, 2H), 4.01 (dd, 1H), 3.95 (td, 1H), 3.86 (s, 3H), 2.32-2.54 (m, 2H).

Step C: [1-(Tetrahydrofuran-3-yl)-1H-pyrazol-5-yl]methanol

A solution of the compound obtained in Step B (8.43 g; 49.0 mmol) in tetrahydrofuran (50 mL) is added to a suspension of lithium aluminium hydride (3.38 g; 86.0 mmol) in tetrahydrofuran (100 mL) cooled to 0° C., and then the whole is stirred at ambient temperature for 16 hours. The reaction mixture is cooled to 0° C. and diluted slowly with water (3.4 mL), 15% aqueous sodium hydroxide solution (6.8 mL) and finally with water (6.8 mL). Magnesium sulphate is added to the mixture. After filtration and concentration of the filtrate, the title product is obtained, which is used subsequently without being purified.

$^1$H NMR (400 MHz, CDCl$_3$, 300 K) δ ppm: 7.43 (s, 1H), 6.17 (s, 1H), 5.05-5.18 (m, 1H), 4.69 (s, 2H), 4.19 (q, 1H), 4.06-4.13 (m, 1H), 3.91-4.02 (m, 2H), 2.32-2.50 (m, 2H), 2.10-2.32 (m, 1H).

Step D: [4-Bromo-1-(tetrahydrofuran-3-yl)-1H-pyrazol-5-yl]methanol

N-Bromosuccinimide (8.78 g; 49.3 mmol) is added in portions to a solution of the compound obtained in Step C (7.9 g; 47 mmol) in dichloromethane (100 mL) at 0° C., and then the whole is stirred at ambient temperature for 1.25 hours. The reaction mixture is diluted in 1 M aqueous sodium hydroxide solution (100 mL). After extraction with dichloromethane, the organic phases are combined, washed with water and dried over sodium sulphate, filtered and concentrated to dryness. The residue obtained is purified by chromatography over silica gel using heptane and ethyl acetate as eluants to obtain the title product.

$^1$H NMR (400 MHz, CDCl$_3$, 300 K) δ ppm: 7.44 (s, 1H), 5.08-5.19 (m, 1H), 4.69 (d, 2H), 4.19 (q, 1H), 4.09 (dd, 1H), 3.89-4.01 (m, 2H), 2.32-2.48 (m, 3H).

Step E: 4-Bromo-5-(chloromethyl)-1-(tetrahydrofuran-3-yl)-1H-pyrazole

Methanesulphonyl chloride (2.85 mL; 36.1 mmol) is added to a solution of the compound obtained in Step D (8.93 g; 36.1 mmol) and triethylamine (7.5 mL; 54.2 mmol) in dichloromethane (100 mL), and then the whole is stirred at ambient temperature for 16 hours. The reaction mixture is diluted in water. After extraction with dichloromethane, the organic phases are combined, washed with water and dried over sodium sulphate, filtered and concentrated to dryness to obtain the title product, which is used subsequently without being purified.

$^1$H NMR (400 MHz, CDCl$_3$, 300 K) δ ppm: 7.49 (s, 1H), 4.97-5.05 (m, 1H), 4.64 (s, 2H), 4.09-4.22 (m, 2H), 3.93-4.05 (m, 2H), 2.42 (q, 2H).

Step F: [4-Bromo-1-(tetrahydrofuran-3-yl)-1H-pyrazol-5-yl]acetonitrile

Potassium cyanide (3.88 g; 59.7 mmol) is added to a solution of the compound obtained in Step E (7.92 g; 29.8 mmol) in a mixture of acetonitrile (80 mL) and water (80 mL), and then the whole is stirred at 60° C. for 16 hours. The acetonitrile is evaporated off and the aqueous phase is extracted with ethyl acetate. The organic phases are combined, washed with water, saturated aqueous sodium chloride solution, and then dried over sodium sulphate, filtered and concentrated to dryness. The residue obtained is purified by chromatography over silica gel using heptane and ethyl acetate as eluants to obtain the title product.

$^1$H NMR (400 MHz, CDCl$_3$, 300 K) δ ppm: 7.53 (s, 1H), 4.92-5.00 (m, 1H), 4.14-4.25 (m, 2H), 4.03-4.10 (m, 1H), 3.97 (td, 1H), 3.85 (d, 2H), 2.36-2.54 (m, 2H).

Step G: 2-[4-Bromo-1-(tetrahydrofuran-3-yl)-1H-pyrazol-5-yl]ethanol

1 M Diisobutylaluminium hydride solution in dichloromethane (53.3 mL; 53.3 mmol) is added at −78° C. to a solution of the compound obtained in Step F (6.83 g; 26.7 mmol) in dichloromethane (133 mL), and then the whole is stirred at −78° C. for 3 hours. After the slow addition of methanol (10 mL) and sodium borohydride (3.04 g; 80.1 mmol), the reaction mixture is stirred at ambient temperature for 16 hours and then diluted with 1 N aqueous hydrochloric acid solution (50 mL). After 10 minutes' contact, the solvents are evaporated off and the product is extracted with ethyl acetate. The organic phases are combined, washed with saturated aqueous sodium chloride solution, dried over magnesium sulphate, filtered and concentrated to dryness. The residue obtained is purified by chromatography over silica gel using dichloromethane and methanol as eluants to obtain the title product.

$^1$H NMR (400 MHz, CDCl$_3$, 300 K) δ ppm: 7.48 (s, 1H), 5.04 (tt, 1H), 4.13-4.21 (m, 2H), 4.06-4.12 (m, 1H), 3.91-4.00 (m, 2H), 3.80-3.89 (m, 2H), 2.96 (t, 2H), 2.29-2.44 (m, 2H).

Step H: tert-Butyl 5-{2-[4-bromo-1-(tetrahydrofuran-3-yl)-1H-pyrazol-5-yl]ethoxy}-3,4-dihydroisoquinoline-2(1H)-carboxylate A solution of triphenylphosphine (2.64 g; 10.1 mmol) and diisopropyl azodicarboxylate (1.97 mL; 10.1 mmol) in tetrahydrofuran at 0° C. is prepared. After discolouration and the appearance of a whitish precipitate (after 5 minutes), a solution of the compound obtained in Step G (2.02 g; 7.74 mmol) in tetrahydrofuran (10 mL) is added, and then the whole is stirred at ambient temperature for 1 hour. After addition of the compound of Preparation 3b' (2.5 g; 10.1 mmol) in solution in tetrahydrofuran (10 mL), the reaction mixture is stirred at ambient temperature for 4 hours and then diluted with dimethyl sulphoxide (10 mL). After concentration of the reaction mixture, the residue is purified by chromatography over RP-18 phase using methanol and water as eluants and then by chromatography over silica gel using dichloromethane and methanol as eluants to obtain the title product.

$^1$H NMR (400 MHz, CDCl$_3$, 300 K) δ ppm: 7.49 (s, 1H), 7.12 (t, 1H), 6.74 (d, 1H), 6.66 (d, 1H), 4.99-5.09 (m, 1H), 4.54 (s, 2H), 4.12-4.23 (m, 3H), 4.09 (dd, 1H), 3.93-4.02 (m, 2H), 3.54-3.69 (m, 2H), 3.21 (td, 2H), 2.63-2.71 (m, 2H), 2.28-2.47 (m, 2H), 1.48 (s, 9H).

Step I: tert-Butyl 5-(2-{4-[(4-{[tert-butyl(dimethyl)silyl]oxy}phenyl)amino]-1-(tetrahydrofuran-3-yl)-1H-pyrazol-5-yl}ethoxy)-3,4-dihydroisoquinoline-2(1H)-carboxylate The title compound is obtained in accordance with the process described in Step B of Preparation 7b" using the compound of the preceding step.

$^1$H NMR (400 MHz, CDCl$_3$, 300 K) δ ppm 7.48 (s, 1H), 7.08 (t, 1H), 6.73 (d, 1H), 6.62-6.67 (m, 2H), 6.56 (d, 1H), 6.48-6.52 (m, 2H), 4.96-5.04 (m, 1H), 4.75 (s, 1H), 4.54 (s, 2H), 4.17-4.24 (m, 1H), 4.02-4.15 (m, 4H), 3.94-4.02 (m, 1H), 6.61 (br. s, 1H), 3.11 (t, 2H), 2.67 (br. s, 2H), 2.45-2.54 (m, 1H), 2.31-2.42 (m, 1H), 1.49 (s, 9H), 0.96 (s, 9H), 0.15 (s, 6H).

Preparation 10b": tert-Butyl 4-(2-{4-[(4-{[tert-butyl(dimethyl)silyl]oxy}phenyl)amino]-1-methyl-1H-pyrazol-5-yl}ethoxy)-1,3-dihydro-2H-isoindole-2-carboxylate

Step A: tert-Butyl 4-[2-(4-bromo-1-methyl-1H-pyrazol-5-yl)ethoxy]-1,3-dihydro-2H-isoindole-2-carboxylate A solution of the compound obtained in Step B of Preparation 3b" (1 g; 4.92 mmol) and of the compound of Preparation 6b' (1.54 g; 6.54 mmol) in a mixture of tetrahydrofuran (10 mL) and toluene (10 mL) is degassed with argon for 10 minutes. Cyanomethylene tri-n-butylphosphorane (2.58 mL; 9.84 mmol) is added, and then the whole is sealed and stirred at 110° C. for 48 hours. The reaction mixture is concentrated and then diluted in a mixture of ethyl acetate and water. After decantation, the organic phase is washed with water and saturated aqueous sodium chloride solution and then dried over magnesium sulphate, filtered and concentrated to dryness. The residue is triturated in cyclohexane to obtain the title product.

$^1$H NMR (400 MHz, dmso-d6, 300K) δ ppm: 7.49 (s, 1H), 7.24 (t, 1H), 6.89 (m, 2H), 4.55 (d, 2H), 4.41 (m, 2H), 4.19 (t, 2H), 3.87 (d, 3H), 3.16 (t, 2H), 1.45 (d, 9H).

IR: ν: >C=C<: 1686 cm$^{-1}$.

Step B: tert-Butyl 4-(2-{4-[(4-{[tert-butyl(dimethyl)silyl]oxy}phenyl)amino]-1-methyl-1H-pyrazol-5-yl}ethoxy)-1,3-dihydro-2H-isoindole-2-carboxylate A solution of the compound obtained in Step A (0.95 g; 2.25 mmol) and of the compound obtained in Step B of Preparation 1b'' (0.74 g; 3.37 mmol) in tetrahydrofuran (50 mL) is degassed with argon for 10 minutes. Sodium tert-butylate (281 mg; 2.9 mmol) and chloro(2-di-tert-butylphosphino-2',4',6'-triisopropyl-1,1'-biphenyl)[2-(2-aminoethyl)phenyl]-palladium(II) (154 mg; 0.22 mmol) are added, and then the whole is stirred at 50° C. for 3 hours. The reaction mixture is filtered over Celite®. After rinsing with ethyl acetate, the product is extracted with ethyl acetate and then the organic phases are washed with saturated aqueous ammonium chloride solution, water and saturated aqueous sodium chloride solution and then dried over magnesium sulphate, filtered and concentrated to dryness. The residue is purified by chromatography over silica gel using dichloromethane and ethyl acetate as eluants to obtain the title product.

$^1$H NMR (400 MHz, dmso-d6, 300 K) δ ppm: 7.28 (s, 1H), 7.18 (t, 1H), 6.88 (2d, 1H), 6.75 (d, 1H), 6.69 (2s, 1H), 6.58 (d, 2H), 6.49 (d, 2H), 4.55 (d, 2H), 4.41 (s, 2H), 4.1 (t, 2H), 3.81 (s, 3H), 3.01 (t, 2H), 1.48 (s, 9H), 0.91 (s, 9H), 0.11 (s, 6H).

IR: ν: >NH: 3308 cm$^{-1}$; >C=O: 1681 cm$^{-1}$; >C=C<: 1617 cm$^{-1}$.

Preparation 11b'': tert-Butyl (3R or 3S)-5-(3-{3-[(4-{[tert-butyl(dimethyl)-silyl]oxy}phenyl)amino]-5-cyano-1-methyl-1H-pyrrol-2-yl}propoxyl-3-methyl-3,4-dihydroisoquinoline-2(1H)-carboxylate

Step A: tert-Butyl 5-[3-(3-bromo-5-cyano-1-methyl-1H-pyrrol-2-yl)propoxy]-3-methyl-3,4-dihydroisoquinoline-2(1H)-carboxylate A solution of the compound obtained in Step D of Preparation 5b'' (3.19 g; 13.12 mmol) and of the compound obtained in Preparation 7b' (3.14 g; 11.93 mmol) in a mixture of tetrahydrofuran (30 mL) and toluene (30 mL) is degassed with argon. Cyanomethylene tri-n-butylphosphorane (6.26 mL; 23.86 mmol) is added. The flask is sealed and the reaction mixture is stirred at 110° C. for 20 hours and then concentrated. The residue so obtained is diluted in a mixture of ethyl acetate and water. After extraction of the aqueous phase with ethyl acetate, the organic phases are combined, washed with water, saturated aqueous sodium chloride solution, and then dried over magnesium sulphate, filtered and concentrated to dryness. The residue is purified by chromatography over silica gel using heptane and ethyl acetate as eluants to obtain the title product.

$^1$H NMR (400 MHz, dmso-d6, 300 K) δ ppm: 7.11 (t, 1H), 7.09 (s, 1H), 6.78 (t, 2H), 4.55 (d, 2H), 4.5 (m, 1H), 3.95 (m, 2H), 3.7 (m, 3H), 2.85 (t, 2H), 2.69 (d, 2H), 1.95 (t, 2H), 1.4 (s, 9H), 1 (d, 3H).

IR: ν: —CN: 2215 cm$^{-1}$; >C=O: 1686 cm$^{-1}$.

Step B: tert-Butyl 5-(3-{3-[(4-{[tert-butyl(dimethyl)silyl]oxy}phenyl)amino]-5-cyano-1-methyl-1H-pyrrol-2-yl}propoxy)-3-methyl-3,4-dihydroisoquinoline-2(1H)-carboxylate The title compound is obtained in accordance with the process described in Step D of Preparation 3b'' using the compound of the preceding step.

$^1$H NMR (400 MHz, dmso-d6, 300 K) δ ppm: 7.05 (t, 1H), 6.8 (m, 2H), 6.75 (d, 1H), 6.65 (d, 1H), 6.55 (d, 2H), 6.5 (d, 2H), 4.65 (d, 1H), 4.15 (d, 1H), 4.45 (m, 1H), 3.88 (t, 2H), 3.65 (s, 3H), 2.75 (t, 2H), 2.55 (d, 2H), 1.9 (m, 2H), 1.45 (s, 9H), 0.98 (d, 3H), 0.95 (s, 6H), 0.1 (s, 9H).

IR: ν: >NH: 3400 cm$^{-1}$; —CN: 2208 cm$^{-1}$: >C=O: 1688 cm$^{-1}$.

Step C: tert-Butyl (3R or 3S)-5-(3-{3-[(4-{[tert-butyl(dimethyl)silyl]oxy}phenyl)amino]-5-cyano-1-methyl-1H-pyrrol-2-yl}propoxy)-3-methyl-3,4-dihydroisoquinoline-2(1H)-carboxylate The title compound is obtained by chromatography in chiral phase (S,S) Whelk-01 using heptane and isopropanol as eluants to obtain the title product.

$^1$H NMR (400 MHz, dmso-d6, 300 K) δ ppm: 7.07 (t, 1H), 6.77 (s, 1H), 6.77 (m, 1H), 6.73 (d, 1H), 6.66 (d, 1H), 6.56 (d, 2H), 6.49 (d, 2H), 4.62 (d, 1H), 4.14 (d, 1H), 4.46 (m, 1H), 3.87 (t, 2H), 3.66 (s, 3H), 2.74 (t, 2H), 2.57 (m, 2H), 1.89 (m, 2H), 1.43 (s, 9H), 0.95 (d, 3H), 0.92 (s, 9H), 0.11 (s, 6H).

Preparation 12b'': tert-Butyl (3S or 3R)-5-(3-{3-[(4-{[tert-butyl(dimethyl)silyl]-oxy}phenyl)amino]-5-cyano-1-methyl-1H-pyrrol-2-yl}propoxy)-3-methyl-3,4-dihydro-isoquinoline-2(1H)-carboxylate The title compound is obtained in accordance with the process of Preparation 11b''.

$^1$H NMR (400 MHz, dmso-d6, 300 K) δ ppm: 7.07 (t, 1H), 6.77 (s, 1H), 6.77 (m, 1H), 6.73 (d, 1H), 6.66 (d, 1H), 6.56 (d, 2H), 6.49 (d, 2H), 4.62 (d, 1H), 4.14 (d, 1H), 4.46 (m, 1H), 3.87 (t, 2H), 3.66 (s, 3H), 2.74 (t, 2H), 2.57 (m, 2H), 1.89 (m, 2H), 1.43 (s, 9H), 0.95 (d, 3H), 0.92 (s, 9H), 0.11 (s, 6H).

Preparation 13b'': tert-Butyl 4-(2-{5-(benzyloxy)-2-[(5-cyano-1,2-dimethyl-1H-pyrrol-3-yl)amino]phenoxy}ethyl)piperidine-1-carboxylate

Step A: 4-(Benzyloxy)-2-fluoro-1-nitrobenzene

To a solution of 3-fluoro-4-nitrophenol (12.76 g; 81.2 mmol) in acetone (165 mL) there are added potassium carbonate (13.47 g; 97.5 mmol) and benzyl bromide (9.75 mL; 82.0 mmol). The reaction mixture is stirred at reflux for 14 hours and then, after returning to ambient temperature, it is diluted in water. After extraction of the aqueous phase with ethyl acetate, the organic phases are combined, washed with saturated aqueous sodium chloride solution and then dried over magnesium sulphate, filtered and concentrated to dryness. The residue is taken up in a minimum amount of ethyl acetate and pentane, and the precipitate obtained is filtered to obtain the title product.

$^1$H NMR (400 MHz, dmso-d6, 300 K) δ ppm: 8.15 (t, 1H), 7.25 (dd, 1H), 7.05 (dd, 1H), 5.25 (s, 2H), 7.3-7.5 (m, 5H).

IR: ν: —NO2: 1510 and 1500 cm$^{-1}$; —NO2: 1329 cm$^{-1}$.

Step B: tert-Butyl 4-{2-[5-(benzyloxy)-2-nitrophenoxy]ethyl}piperidine-1-carboxylate A solution of tert-butyl 4-(2-hydroxyethyl)piperidine-1-carboxylate (8 g; 35 mmol) in tetrahydrofuran (30 mL) is added dropwise to a mixture of sodium hydride (1.52 g; 38.1 mmol) in tetrahydrofuran (30 mL) at 0° C. The reaction mixture is stirred for 15 minutes at 0° C. and then for 30 minutes at ambient temperature. The reaction mixture is again cooled to 0° C., and a solution of the compound obtained in Step A (7.86 g; 31.79 mmol) in tetrahydrofuran (30 mL) is then added dropwise. The reaction mixture is stirred at ambient temperature for 17 hours and then hydrolysed. After extraction of the aqueous phase with ethyl acetate, the organic phases are combined and then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 7.95 (d, 1H), 7.4 (m, 5H), 6.9 (d, 1H), 6.7 (dd, 1H), 5.25 (s, 2H), 4.2 (t, 2H), 3.9/2.7 (m, 4H), 1.7 (m, 3H), 1.7/1.05 (m, 4H), 1.4 (s, 9H).

IR: ν: >C=O: 1683 cm$^{-1}$; —NO2: 1513 and 1255 cm$^{-1}$.

Step tert-Butyl 4-{2-[2-amino-5-(benzyloxy)phenoxy]ethyl}piperidine-1-carboxylate Iron (12.9 g; 23.1 mmol) is added to a solution of the compound obtained in Step B (9.4 g; 22 mmol) in a mixture of tetrahydrofuran (70 mL) and glacial acetic acid (70 mL), and then the whole is heated at 65° C. for 18 hours. The reaction mixture is filtered over Celite® and then, after addition of 5 N aqueous sodium hydroxide solution to reach pH=7, it is concentrated by half. After extraction of the aqueous phase with dichloromethane, the organic phases are combined and then dried over magnesium sulphate, filtered and concentrated to dryness. The residue is purified by chromatography over silica gel using dichloromethane and ethyl acetate as eluants to obtain the title product.

$^1$H NMR (400 MHz, dmso-d6, 300 K) δ ppm: 7.4-7.3 (m, 5H), 6.55 (m, 2H), 6.35 (dd, 1H), 4.95 (s, 2H), 4.22 (m, 2H), 3.95 (m, 4H), 2.7 (m, 2H), 1.65 (m, 3H), 1.65/1.05 (m, 4H), 1.4 (s, 9H).

IR: ν: —NH2: 3450–3365 cm$^{-1}$; >C=O: 1669 cm$^{-1}$.

Step D:
4-Bromo-1,5-dimethyl-1H-pyrrole-2-carbonitrile

A solution of bromine (24 mL; 457.74 mmol) in glacial acetic acid (60 mL) is added dropwise to a solution of 1,5-dimethyl-1H-pyrrole-2-carbonitrile (15 g; 124.8 mmol) in glacial acetic acid (300 mL). The reaction mixture is stirred for 16 hours at ambient temperature. After concentration of the reaction mixture by half, the same quantity of water is added (180 mL) and the precipitate that forms is filtered off and then dissolved in dichloromethane. The organic phase is washed with saturated aqueous sodium chloride solution and then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 7.05 (s, 1H), 3.65 (s, 3H), 2.23 (s, 3H).

IR: ν: >CH: 3131 cm$^{-1}$; >CN: 2220 cm$^{-1}$.

Step E: tert-Butyl 4-(2-{5-(benzyloxy)-2-[(5-cyano-1,2-dimethyl-1H-pyrrol-3-yl)amino]-phenoxy}ethyl)piperidine-1-carboxylate The title compound is obtained in accordance with the process described in Step B of Preparation 2b" using the compound of the preceding step.

$^1$H NMR (400 MHz, dmso-d6, 300 K) δ ppm: 7.4 (d, 2H), 7.35 (t, 2H), 7.3 (f, 1H), 6.7 (s, 1H), 6.6 (d, 1H), 6.35 (dd, 1H), 6.3 (d, 1H), 5.85 (s, 1H), 4.95 (s, 2H), 4.05 (t, 2H), 3.9/2.7 (m+m, 2+2 H), 3.6 (s, 3H), 2.05 (s, 3H), 1.7 (m, 5H), 1.4 (s, 9H), 1.05 (m, 2H).

IR: ν: >NH: 3404 cm$^{-1}$; >CN: 2207 cm$^{-1}$; >C=O: 1684 cm$^{-1}$.

Preparation 14b": tert-Butyl 3-(2-{5-(benzyloxy)-2-[(5-cyano-1,2-dimethyl-1H-pyrrol-3-yl)amino]phenoxy}ethyl)piperidine-1-carboxylate The title compound is obtained in accordance with the process of Preparation 13b" using tort-butyl 3-(2-hydroxyethyl)-piperidine-1-carboxylate in Step B.

$^1$H NMR (400 MHz, dmso-d6, 300 K) δ ppm: 7.4 (d, 2H), 7.35 (t, 1H), 7.3 (t, 2H), 6.75 (s, 1H), 6.62 (d, 1H), 6.35 (dd, 1H), 6.25 (d, 1H), 5.85 (s, 1H), 4.95 (s, 2H), 4.05-2.5 (m, 4H), 4.05 (t, 2H), 3.63 (s, 3H), 2.1 (s, 3H), 1.8-1.3 (m, 7H), 1.35 (br. s, 9H).

IR: ν: >NH: 3400 cm$^{-1}$; >CN: 2207 cm$^{-1}$; >C=O: 1684 cm$^{-1}$.

Preparation 15b": 1-(3-{[2-(tert-Butoxycarbonyl)-1,2,3,4-tetrahydroisoquinolin-5-yl]-oxy}propyl)-3-{[4-(prop-2-en-1-yloxy)phenyl]amino}pyridinium iodide Step A: 1-Nitro-4-(prop-2-en-1-yloxy)benzene To a solution of 4-nitrophenol (20 g; 0.144 mol) in acetonitrile (500 mL) there are added allyl bromide (15 mL; 0.173 mol) and caesium carbonate (52 g, 0.158 mol), and then the whole is stirred for 16 hours at ambient temperature and for 2 hours at 70° C. After filtration of the insoluble material and concentration of the filtrate, the residue is diluted with dichloromethane and water. After decantation, the organic phase is washed with water and then dried over magnesium sulphate, filtered and concentrated to dryness. The residue is purified by chromatography over silica gel using ethyl acetate and petroleum ether as eluants to obtain the title product.

$^1$H NMR (400 MHz, CDCl$_3$, 300 K) δ ppm: 8.2 (d, 2H), 7 (d, 2H), 6 (m, 1H), 5.45 (tdd, 1H), 5.4 (tdd, 1H), 4.6 (m, 2H).

IR: ν: >NO2: 1590 and 1331 cm-$^1$.

Step B: 4-(Prop-2-en-1-yloxy)aniline

The title compound is obtained in accordance with the process described in Step C of Preparation 13b" using the compound of the preceding step.

$^1$H NMR (400 MHz, dmso-d6, 300 K) δ ppm: 6.65 (d, 2H), 6.49 (d, 2H), 6 (m, 1H), 5.34/5.2 (dd, 2H), 4.59 (s, 2H), 4.4 (d, 2H).

IR: ν: >NH2: 3429 and 3350 cm-$^1$.

Step C: N-[4-(Prop-2-en-1-yloxy)phenyl]pyridin-3-amine

The title compound is obtained in accordance with the process described in Step D of Preparation 3b" using 3-bromopyridine and the compound of the preceding step.

$^1$H NMR (400 MHz, dmso-d6, 300 K) δ ppm: 8.22 (d, 1H), 8.05 (s, 1H), 7.92 (dd, 1H), 7.31-7.11 (2*dd, 2H), 7.05 (d, 2H), 6.91 (d, 2H), 6.04 (m, 1H), 5.46-5.19 (2*dd, 2H), 4.52 (d, 2H).

IR: ν: >NH: 3250 and 3184 cm$^{-1}$.

Step D: 1-(3-{[2-(tert-Butoxycarbonyl)-1,2,3,4-tetrahydroisoquinolin-5-yl]oxy}propyl)-3-{[4-(prop-2-en-1-yloxy)phenyl]amino}pyridinium iodide The compound of Preparation 8b' (1.05 g; 2.5 mmol) is added to a solution of the compound obtained in Step C (740 mg; 3.27 mmol) in dioxane (13 mL), and then the whole is stirred for 18 hours at 70° C. After concentration, the residue is purified by chromatography over silica gel using dichloromethane and methanol as eluant to obtain the title product.

$^1$H NMR (400 MHz, dmso-d6, 300 K) δ ppm: 9.1 (s, 1H), 8.34 (m, 2H), 7.81 (m, 2H), 7.14 (t, 1H), 7.12 (d, 2H), 6.91 (d, 2H), 6.78 (t, 2H), 6.04 (m, 1H), 5.4/5.27 (2*dd, 2H), 4.67 (t, 2H), 4.54 (d, 2H), 4.46 (s, 2H), 4.04 (t, 2H), 3.5 (t, 2H), 2.5 (d, 2H), 2.37 (t, 2H), 1.42 (s, 9H).

IR: ν: >NH: 3500–2700 cm$^{-1}$; >C=O: 1686 cm$^{-1}$.

Preparation 16b'': 2-Methyl-N-[4-(prop-2-en-1-yloxy)phenyl]-4-[2-(tetrahydro-2H-pyran-2-yloxy)ethoxy]pyrimidin-5-amine

Step A: 4-Chloro-2-methyl-6-[2-(tetrahydro-2H-pyran-2-yloxy)ethoxy]pyrimidin-5-amine A solution of 2-tetrahydropyran-2-yloxyethanol (4.6 mL; 33.6 mmol) in tetrahydrofuran (60 mL) is added dropwise to a mixture of sodium hydride (1.5 g; 36.4 mmol) in tetrahydrofuran (10 mL) at 0° C. The reaction mixture is stirred for 15 minutes at 0° C. and then for 30 minutes at ambient temperature. The reaction mixture is again cooled to 0° C. and then a solution of 5-amino-4,6-dichloro-2-methylpyrimidine (5 g; 28 mmol) in tetrahydrofuran (70 mL) is added dropwise. The reaction mixture is stirred at ambient temperature for 17 hours and then hydrolysed. After extraction of the aqueous phase with ethyl acetate, the organic phases are combined and then dried over magnesium sulphate, filtered and concentrated to dryness. The residue is purified by chromatography over silica gel using petroleum ether and ethyl acetate as eluants to obtain the title product.

$^1$H NMR (400 MHz, dmso-d6, 300 K) δ ppm: 5.01 (s, 2H), 4.66 (m, 1H), 4.49 (m, 2H), 3.94 (2*m, 2H), 3.77/3.44 (2*m, 2H), 2.34 (s, 3H), 1.76-1.35 (m, 4H), 1.61/1.45 (2*m, 2H).

IR: ν: —NH2: 3464 and 3340 cm$^{-1}$.

Step 13: 2-Methyl-4-[2-(tetrahydro-2H-pyran-2-yloxy)ethoxy]pyrimidin-5-amine Palladium on carbon (10% by mass) is added to a solution of the compound obtained in Step A (6.9 g; 24.0 mmol) in ethanol (120 mL), and then the whole is hydrogenated for 6 hours at ambient temperature under 1 bar. The reaction mixture is filtered and concentrated to dryness. The residue is diluted in a mixture of saturated aqueous sodium bicarbonate solution and dichloromethane. After decantation and extraction with dichloromethane, the organic phases are combined and then dried over magnesium sulphate to provide the title product.

$^1$H NMR (400 MHz, dmso-d6, 300 K) δ ppm: 7.76 (s, 1H), 4.76 (s, 2H), 4.65 (m, 1H), 4.46 (m, 2H), 3.93/3.75 (2m, 2H), 3.75/3.44 (2m, 2H), 2.34 (s, 3H), 1.75-1.35 (m, 6H).

IR: ν: —NH$_2$: 3600–3100 cm$^{-1}$.

Step C: 1-Bromo-4-(prop-2-en-1-yloxy)benzene

To a solution of 4-bromophenol (10 g; 57.8 mmol) in acetone (290 mL) there are added allyl bromide (5.5 mL; 63.6 mmol) and potassium carbonate (16 g, 116 mmol), and then the whole is stirred for 6 hours at 85° C. and then for 16 hours at ambient temperature. After filtration of the insoluble material and concentration of the filtrate, the residue is diluted with ethyl acetate and water. After decantation, the organic phase is washed with water and saturated aqueous sodium chloride solution and then dried over magnesium sulphate, filtered and concentrated to dryness. The residue is purified by chromatography over silica gel using ethyl acetate and petroleum ether as eluants to obtain the title product.

$^1$H NMR (400 MHz, CDCl$_3$, 300 K) δ ppm: 7.36 (d, 2H), 6.79 (d, 2H), 6.01 (m, 1H), 5.4 (d, 1H), 5.3 (d, 1H), 4.5 (d, 2H).

IR: ν: >CH—Ar: 821 cm$^{-1}$; >C=C<: 1590, 1578 and 1488 cm$^{-1}$.

Step D: 2-Methyl-N-[4-(prop-2-en-1-yloxy)phenyl]-4-[2-(tetrahydro-2H-pyran-2-yloxy)-ethoxy]pyrimidin-5-amine The title compound is obtained in accordance with the process described in Step B of Preparation 2b'' using the compounds obtained in the preceding Steps B and C.

$^1$H NMR (400 MHz, dmso-d6, 300 K) δ ppm: 8.07 (s, 1H), 7.17 (s, 1H), 6.98 (d, 2H), 6.86 (d, 2H), 6.03 (m, 1H), 5.38/5.24 (2*dd, 2H), 4.62 (m, 1H), 4.52 (m, 2H), 4.5 (m, 2H), 3.94/3.76 (2*m, 2H), 3.74/3.4 (2*m, 2H), 2.43 (s, 3H), 1.61 (m, 2H), 1.42 (m, 4H).

IR: ν: >NH: 3415 cm$^{-1}$; >C=C<: 1649 cm$^{-1}$.

Preparation 17b'': tert-Butyl [2-(3-cyano-5-{[4-prop-2-en-1-yloxy)phenyl]amino}-phenoxy)ethylmethylcarbamate

Step A: (3-Bromo-5-methoxyphenyl)methanol

Borane-dimethyl sulphide complex (32.5 mL; 64.9 mmol) is added dropwise to a solution of 3-bromo-5-methoxybenzoic acid (10 g; 43.3 mmol) in tetrahydrofuran (280 mL), and then the whole is stirred for 2 hours. The reaction mixture is acidified dropwise with 2 N aqueous hydrochloric acid solution to pH=1. After extraction with ether, the organic phase is washed with 1 N aqueous sodium hydroxide solution and saturated aqueous sodium chloride solution and then dried over magnesium sulphate, filtered and concentrated to dryness. The title product is obtained in the form of an oil, which is used in the following step without being purified.

$^1$H NMR (400 MHz, dmso-d6, 300 K) δ ppm: 7.08 (m, 1H), 6.99 (m, 1H), 6.89 (m, 1H), 5.3 (br. s, 1H), 4.47 (s, 2H), 3.75 (s, 3H).

IR: ν: —OH: 1588 cm$^{-1}$; >C—O: 1268 and 1038 cm$^{-1}$; γ: >CH—Ar: 811 cm$^{-1}$.

Step B: 3-Bromo-5-methoxybenzaldehyde

Dess-Martin reagent (20.3 mL; 47.8 mmol) is added to a solution of the compound obtained in Step A (8.6 g; 39.8 mmol) in dichloromethane (400 mL), and then the whole is stirred for 2 hours. After addition of ether, the reaction mixture is filtered over a bed of silica. The filtrate is concentrated, taken up in a mixture of heptane and ethyl acetate and then filtered again over a bed of silica. After concentration of the filtrate, the title product is obtained in the form of a pale yellow solid, which is used in the following step without being purified.

¹H NMR (400 MHz, dmso-d6, 300 K) δ ppm: 9.5 (s, 1H), 7.69 (t, 1H), 7.5 (t, 1H), 7.42 (t, 1H), 3.85 (s, 3H).

IR: ν: >C=O: 1691 cm⁻¹.

Step C: (Z)-1-(3-Bromo-5-methoxyphenyl)-N-hydroxymethanimine

To a solution of the compound obtained in Step B (7.8 g; 36.4 mmol) in ethanol (10 mL) there are added in succession hydroxylamine hydrochloride (12.6 g; 182 mmol) and pyridine (6.27 mL; 87.4 mmol), and then the whole is stirred at 65° C. for 1 hour. After returning to ambient temperature, the reaction mixture is diluted with a mixture of ethyl acetate and water. After decantation, the organic phase is washed with water and saturated aqueous sodium chloride solution and then dried over magnesium sulphate, filtered and concentrated to dryness. The title product is obtained in the form of a white solid, which is used in the following step without being purified.

¹H NMR (400 MHz, dmso-d6, 300 K) δ ppm: 11.45 (s, 1H), 8.1 (s, 1H), 7.35 (1, 1H), 7.16 (d, 2H), 3.8 (s, 3H).

IR: ν: —OH: 3300–3000 cm⁻¹; Ar: 1600 and 1564 cm⁻¹; >C—O: 1220 and 1059 cm⁻¹; —N—O: 960 cm⁻¹; γ: >CH—Ar: 831 cm⁻¹.

Step D: 3-Bromo-5-methoxybenzonitrile

To a solution of the compound obtained in Step C (8.1 g; 35.2 mmol) in dioxane (70 mL) there are added at 0° C. pyridine (22 mL; 211 mmol) and, dropwise, trifluoroacetic anhydride (1.4 mL; 70.4 mmol), and then the whole is stirred at ambient temperature for 24 hours. After returning to 0° C., a second portion of trifluoroacetic anhydride (1.4 mL; 70.4 mmol) is added dropwise, and then the whole is stirred at ambient temperature for 24 hours. After returning to 0° C., a third portion of trifluoroacetic anhydride (1.4 mL; 70.4 mmol) is added dropwise, and then the whole is stirred at 60° C. for 1 hour. After returning to ambient temperature, the reaction mixture is diluted with a mixture of dichloromethane and water. After decantation, the organic phase is washed with 1 N aqueous hydrochloric acid solution and saturated aqueous sodium chloride solution and then dried over magnesium sulphate, filtered and concentrated to dryness. The title product is obtained in the form of a pale yellow solid, which is used in the following step without being purified.

¹H NMR (400 MHz, dmso-d6, 300 K) δ ppm: 7.69 (t, 1H), 7.53 (dd, 1H), 7.5 (dd, 1H), 3.82 (s, 3H).

IR: ν: —CN: 2232 cm⁻¹; Ar: 1597 and 1562 cm⁻¹; >C—O—C<: 1278 and 1051 cm⁻¹; γ: >CH—Ar: 848, 814 and 671 cm⁻¹.

Step E: 3-Bromo-5-hydroxybenzonitrile

Lithium iodide (11.2 g; 83.7 mmol) is added to a solution of the compound obtained in Step D (5.9 g; 27.9 mmol) in collidine (55 mL), and then the whole is stirred at 150° C. for 16 hours. After returning to ambient temperature, the reaction mixture is poured into ice-water. After extraction with dichloromethane, the organic phases are combined, washed with water and then dried over magnesium sulphate, filtered and concentrated to dryness. The title product is obtained in the form of an orange-brown solid, which is used in the following step without being purified.

¹H NMR (400 MHz, dmso-d6, 300 K) δ ppm: 10.7 (br. s, 1H), 7.51 (t, 1H), 7.3 (t, 1H), 7.18 (dd, 1H).

IR: ν: —OH: 3283 cm⁻¹; —CN: 2245 cm⁻¹.

Step F: tert-Butyl (2-hydroxyethyl)methylcarbamate

Di-tert-butyl Bicarbonate (87.3 g; 0.399 mol) is added in portions at ambient temperature to a solution of 2-(methylamino)ethanol (30 g; 0.399 mol) in dichloromethane (800 mL). The mixture is stirred at that temperature for 16 hours. The solvent is evaporated off in vacuo and the residue is purified by chromatography over silica gel using petroleum ether and ethyl acetate as eluants to obtain the title product.

¹H NMR (400 MHz, CDCl₃, 300 K) δ ppm: 3.75 (t, 2H), 3.39 (t, 2H), 2.91 (s, 3H), 2.85 (m, 1H), 1.45 (s, 9H).

IR: ν: —OH: 3431 cm⁻¹; >C=O: 1692 and 1668 cm⁻¹.

Step G: tert-Butyl [2-(3-bromo-5-cyanophenoxy)ethyl]methylcarbamate

The title compound is obtained in accordance with the process described in Step H of Preparation 9b" using the compounds obtained in the preceding Steps E and F.

¹H NMR (400 MHz, dmso-d6, 300 K) δ ppm: 7.7 (br. s, 1H), 7.52 (br. s, 1H), 7.5 (br. s, 1H), 4.2 (m, 2H), 3.5 (t, 2H), 2.88 (br. s, 3H), 1.35 (2br. s, 9H).

IR: ν: —CN: 2235 cm⁻¹; >C=O: 1687 cm⁻¹.

Step H: tert-Butyl [2-(3-cyano-5-{[4-(prop-2-en-1-yloxy)phenyl]amino}phenoxy)ethyl]-methylcarbamate The title compound is obtained in accordance with the process described in Step B of Preparation 2b" using the compound of the preceding step and the compound obtained in Step B of Preparation 15b".

¹H NMR (400 MHz, dmso-d6, 300 K) δ ppm: 7.07 (d, 2H), 6.94 (d, 2H), 6.73 (dd, 2H), 6.63 (t, 1H), 6.05 (m, 1H), 5.4 (dd, 1H), 5.26 (dd, 1H), 4.54 (td, 2H), 4.06 (t, 2H), 3.5 (t, 2H), 2.83 (s, 3H), 1.34 (s, 9H).

IR: ν: —NH: 3344 cm⁻¹; —CN: 2231 cm⁻¹; >C=O: 1741 cm⁻¹; >C=O: 1673 cm⁻¹: 1591 cm⁻¹.

Preparation 18b": tert-Butyl [4-(3-cyano-5-{[4-(prop-2-en-1-yloxy)phenyl]amino}-phenoxy)butyl]methylcarbamate The title compound is obtained in accordance with the process of Preparation 17b" using 4-(methylamino)butanol in Step F.

¹H NMR (400 MHz, dmso-d6, 300 K) δ ppm: 8.23 (s, 1H), 7.07 (d, 2H), 6.94 (d, 2H), 6.73 (t, 1H), 6.68 (t, 1H), 6.63 (t, 1H), 6.05 (m, 1H), 5.39/5.26 (2dquad, 2H), 4.54 (dt, 2H), 3.96 (t, 2H), 3.19 (t, 2H), 2.76 (br. s, 3H), 1.59 (m, 4H), 1.37 (br. s, 9H).

IR: ν: —NH: 3340 cm⁻¹; —CN: 2229 cm⁻¹; >C=O: 1687 cm⁻¹; >C=O: 1670 cm⁻¹.

Preparation 19b": tert-Butyl 5-(2-{2-[(4-{[tert-butyl(dimethyl)silyl]oxy}phenyl)amino]-ethoxy}ethoxy)-3,4-dihydroisoquinoline-2(1H)-carboxylate Step A: tert-Butyl 5-[2-(2-oxoethoxy)ethoxy]-3,4-dihydroisoquinoline-2(1H)-carboxylate Dimethyl sulphoxide (0.2 mL) is added at −78° C. to a solution of oxalyl chloride (0.2 mL; 2.22 mmol) in tetrahydrofuran (7 mL). After 30 minutes' contact at that temperature, there is added dropwise at −78° C. a solution of the compound obtained in Preparation 9b' (0.5 g; 1.48 mmol) in tetrahydrofuran (8 mL) and, under the same conditions, triethylamine (0.77 mL; 5.93 mmol). The whole is stirred for 1 hour at −78° C. and then for 2 hours at 0° C. The reaction mixture is diluted with a mixture of ethyl acetate and water. After decantation, the organic phase is washed with saturated aqueous sodium chloride solution and then dried over magnesium sulphate, filtered and concentrated to dryness. The title product is obtained in the form of a chestnut-brown oil, which is used in the following step without being purified.

$^1$H NMR (400 MHz, dmso-d6, 300 K) δ ppm: 9.6 (s, 1H), 7.13 (t, 1H), 6.82 (d, 1H), 6.75 (d, 1H), 4.46 (br. s, 2H), 4.29 (s, 2H), 4.12 (m, 2H), 3.85 (m, 2H), 3.54 (m, 2H), 2.64 (t, 2H), 1.41 (s, 9H).

IR: ν: >C=O: 1689 cm$^{-1}$.

Step B: tert-Butyl 5-(2-{2-[(4-{[tert-butyl(dimethyl)silyl]oxy}phenyl)amino]-ethoxy}-ethoxy)-3,4-dihydroisoquinoline-2(1H)-carboxylate To a solution of the compound obtained in Step A (0.5 g; 1.49 mmol) in dichloromethane (10 mL) there are added the compound obtained in Step B of Preparation 1 b" (0.4 g; 1.79 mmol) and sodium triacetoxy-borohydride (0.63 g; 2.98 mmol). The whole is stirred for 16 hours at ambient temperature. The reaction mixture is diluted in saturated aqueous sodium hydrogen carbonate solution. After extraction with dichloromethane, the organic phases are washed with saturated aqueous sodium chloride solution and then dried over magnesium sulphate, filtered and concentrated to dryness. The residue is purified by chromatography over silica gel using ethyl acetate and petroleum ether as eluants to obtain the title product.

$^1$H NMR (400 MHz, dmso-d6, 300 K) δ ppm: 7.13 (t, 1H), 6.81 (d, 1H), 6.75 (d, 1H), 6.59 (d, 2H), 6.47 (d, 2H), 5.05 (t, 1H), 4.46 (s, 2H), 4.1 (t, 2H), 3.77 (t, 2H), 3.62 (t, 2H), 3.52 (t, 2H), 3.13 (quad, 2H), 2.63 (t, 2H), 1.42 (s, 9H), 0.92 (s, 9H), 0.11 (s, 6H).

IR: ν: >NH: 3387 cm$^{-1}$; >C=O: 1693 cm$^{-1}$.

Preparation 20b": tert-Butyl 5-[2-(1-{3-[(4-{[tert-butyl(dimethyl)silyl]oxy}phenyl)-amino]-5-cyanophenyl}-1H-1,2,3-triazol-4-yl)ethyl]-3,4-dihydroisoquinoline-2(1H)-carboxylate Step A: 3-Bromo-5-nitrobenzonitrile A solution of 2-amino-3-bromo-5-nitrobenzonitrile (10 g; 41.3 mmol) in N,N-dimethylformamide (85 mL) is added dropwise to a solution of tert-butyl nitrite (8.19 mL; 62 mmol) in N,N-dimethylformamide (35 mL) at 50° C. The mixture is stirred at 50° C. until the evolution of gas has ceased. The crude mixture is then poured into 0.5 N aqueous hydrochloric acid solution (1 L), and then the whole is extracted with methyl tert-butyl ether. The organic phases are combined and washed with saturated aqueous sodium bicarbonate solution and then with saturated aqueous sodium chloride solution, dried over sodium sulphate, filtered and concentrated in vacuo. The residue is purified by chromatography over silica gel using ethyl acetate and heptane as eluants to obtain the title product.

$^1$H NMR (400 MHz, CDCl$_3$, 300 K) δ ppm 8.61 (t, 1H), 8.47 (t, 1H), 8.12 (t, 1H).

Step B: 3-Amino-5-bromobenzonitrile

Tin chloride dihydrate (33.85 g; 150 mmol) is added in portions to a solution of the compound obtained in Step A (6.85 g; 30 mmol) in ethyl acetate (20 mL) and ethanol (82 mL). The reaction mixture is then heated at 70° C. for 30 minutes and concentrated to a volume of approximately 40 mL before being poured onto ice. The mixture so obtained is rendered alkaline with 2 N aqueous sodium hydroxide solution and the whole is stirred for 20 minutes. The product is extracted with ethyl acetate. The organic phases are combined and washed with saturated aqueous sodium chloride solution, dried over sodium sulphate, filtered and concentrated in vacuo. The residue is purified by chromatography over silica gel using ethyl acetate and heptane as eluants to obtain the title product.

$^1$H NMR (400 MHz, CDCl$_3$, 300 K) δ ppm: 7.12 (t, 1H), 7.01 (t, 1H), 6.80-6.83 (m, 1H), 3.97 (br. s, 2H).

Step C: 3-Azido-5-bromobenzonitrile

To a solution of the compound obtained in Step B (3.96 g; 20 mmol) in ethyl acetate (60 mL) at 0° C. there are added dropwise concentrated hydrochloric acid (12 mL), while maintaining the temperature below 5° C., and then, dropwise, a solution of sodium nitrite (1.66 g; 24 mmol) in water (25 mL), likewise while maintaining the temperature below 5° C. After 1 hour's stirring at 0° C., a solution of sodium azide (1.56 g; 24 mmol) in water (25 mL) is added dropwise while maintaining the temperature below 5° C. The reaction mixture is stirred for 3 hours until it returns to ambient temperature and then it is diluted with water. The product is extracted with ethyl acetate. The organic phases are combined and washed with saturated aqueous sodium chloride solution, dried over sodium sulphate, filtered and concentrated in vacuo to provide the title compound without purification.

$^1$H NMR (400 MHz, CDCl$_3$, 300 K) δ ppm: 7.55 (t, 1H), 7.41 (t, 1H), 7.20-7.24 (m, 1H).

Step D: tert-Butyl 5-{2-[1-(3-bromo-5-cyanophenyl)-1H-1,2,3-triazol-4-yl]ethyl}-3,4-dihydroisoquinoline-2(1H)-carboxylate To a solution of the compound obtained in Step C (1.56 g; 7 mmol) and of the compound obtained in Preparation 10b' (2 g; 7 mmol) in tetrahydrofuran (30 mL) there are added copper iodide (133 mg; 0.7 mmol) and triethylamine (1.16 mL; 8.4 mmol). The reaction mixture is stirred at ambient temperature for 16 hours. The reaction mixture is then concentrated to a volume of approximately 15 mL, and the whole is diluted with ethyl acetate. The organic phase is washed with 2 N aqueous hydrochloric acid solution and then with saturated aqueous sodium chloride solution. The organic phase is dried over sodium sulphate, filtered and concentrated in vacuo. The residue is purified by chromatography over silica gel using ethyl acetate and heptane as eluants to obtain the title product.

$^1$H NMR (400 MHz, CDCl$_3$, 300 K) δ ppm: 8.17 (s, 1H), 7.91-7.99 (m, 1H), 7.79-7.86 (m, 1H), 7.64 (br. s, 1H), 7.09-7.20 (m, 1H), 7.03 (dd, 2H), 4.58 (s, 2H), 3.65 (br. s, 2H), 3.06 (br. s, 4H), 2.82 (br. s, 2H), 1.49 (s, 9H).

Step E: tert-Butyl 5-[2-(1-{3-[(4-{[tert-butyl(dimethyl)silyl]oxy}phenyl)amino]-5-cyanophenyl}-1H-1,2,3-triazol-4-yl)ethyl]-3,4-dihydroisoquinoline-2(1H)-carboxylate The title compound is obtained in accordance with the process described in Step B of Preparation 2b" using the compound of the preceding step and the compound of Step 13 of Preparation 1b".

¹H NMR (400 MHz, CDCl₃, 300 K) δ ppm: 7.40-7.76 (m, 2H), 7.19 (s, 1H), 7.05-7.16 (m, 4H), 6.95-7.05 (m, 2H), 6.82-6.90 (m, 2H), 6.67 (br. s, 1H), 4.57 (s, 2H), 3.58-3.67 (m, 2H), 2.96-3.07 (m, 4H), 2.70-2.81 (m, 2H), 1.47 (s, 9H), 1.00 (s, 9H), 0.22 (s, 6H).

Preparation 21b": tert-Butyl 4-(2-{2-[(5-{[4-(prop-2-en-1-yloxy)phenyl]amino}-pyrimidin-2-yl)oxy] ethoxy}ethoxy)-1,3-dihydro-2H-isoindole-2-carboxylate Step A: 5-Bromo-2-[2-(2-chloroethoxy)ethoxy]pyrimidine Caesium carbonate (11.73 g, 36 mmol) is added to a solution of 5-bromo-2-chloropyrimidine (3.48 g; 18 mmol) and 2-(2-chloroethoxy)-ethanol (3.59 g; 28.8 mmol) in acetonitrile (50 mL), and then the whole is stirred for 14 hours at 60° C. After cooling, the reaction mixture is filtered and then the filtrate is concentrated. The residue is purified by chromatography over silica gel using heptane and ethyl acetate as eluants to obtain the title product.
¹H NMR (500 MHz, dmso-d6, 300 K) δ ppm: 8.75 (s, 2H), 4.41 (m, 2H), 3.8 (m, 2H), 3.72 (s, 4H).

Step B: tert-Butyl 4-{2-[2-({5-[(4-hydroxyphenyl)amino]pyrimidin-2-yl}oxy)ethoxy]-ethoxy}-1,3-dihydro-2H-isoindole-2-carboxylate To a solution of the compound obtained in Step A (2.81 g; 10 mmol) and of the compound of Preparation 6b' (2.5 g; 10 mmol) in acetonitrile (100 mL) there are added caesium carbonate (3.9 g, 12 mmol) and potassium iodide (0.35 g; 2.1 mmol), and then the whole is stirred for 14 hours at 60° C. After returning to ambient temperature, the reaction mixture is concentrated. The residue is purified by chromatography over silica gel using heptane and ethyl acetate as eluants.
A solution of the residue so obtained (3.3 g; 6.87 mmol) and of the compound of Step B of Preparation 15b" (1.44 g; 9.6 mmol) in tetrahydrofuran (60 mL) is degassed with argon for 10 minutes. Caesium carbonate (2.91 g; 8.9 mmol) and chloro(2-di-tert-butylphosphino-2',4',6'-triisopropyl-1,1'-biphenyl)[2-(2-aminoethyl)phenyl]palladium(II) (180 mg; 0.26 mmol) are added, and then the whole is stirred at reflux for 5 hours and then at 50° C. for 15 hours. After cooling, the reaction mixture is concentrated. The residue is purified by chromatography over silica gel using heptane and ethyl acetate as eluants to obtain the title product.
¹H NMR (500 MHz, dmso-d6, 300 K) δ ppm: 9.00 (1H, s), 8.22 (1H, s), 8.21 (1H, s), 7.65 (1H, s), 6.90 (1H, d), 6.89 (1H, d), 7.24 (1H, t), 6.86 (2H, m), 6.68 (2H, m), 4.45-4.57 (4H, m), 4.33 (2H, m), 4.16 (2H, m), 3.81 (4H, m), 1.44 (9H, s).

Step C: tert-Butyl 4-(2-{2-[(5-{[4-(prop-2-en-1-yloxy)phenyl]amino}pyrimidin-2-yl)oxy] ethoxy}ethoxy)-1,3-dihydro-2H-isoindole-2-carboxylate The title compound is obtained in accordance with the process described in Step C of Preparation 16b" using the phenol of Step B.
¹H NMR (500 MHz, dmso-d6, 300 K) δ ppm: 8.29/8.28 (s, 2H), 7.81 (brs, 1H), 7.24 (t, 1H), 6.93 (m, 2H), 6.9 (m, 1H), 6.88 (m, 1H), 6.86 (m, 2H), 6.03 (m, 1H), 5.37/5.24 (m+m, 2H), 4.57/4.55 (brs, 2H), 4.48/4.45 (brs, 2H), 4.38-3.78 (m, 8H), 1.44 (s, 9H).

Preparation 22b": tert-Butyl 5-(2-{2-[(5-{[4-(prop-2-en-1-yloxy)phenyl]amino}-pyrimidin-2-yl)oxy] ethoxy}ethoxy)-3,4-dihydroisoquinoline-2(1H)-carboxylate The title compound is obtained in accordance with the process of Preparation 21b" replacing in Step B the compound of Preparation 6b' with the compound of Preparation 3b'.
¹H NMR (500 MHz, dmso-d6, 300 K) δ ppm: 8.29 (s, 2H), 7.82 (s, 1H), 7.12 (t, 1H), 6.94 (m, 2H), 6.86 (m, 2H), 6.8 (d, 1H), 6.73 (d, 1H), 6.02 (m, 1H), 5.37/5.23 (m+m, 2H), 4.49 (m, 2H), 4.45 (br., 2H), 4.36 (m, 2H), 4.1 (m, 2H), 3.81 (m, 2H), 3.81 (m, 2H), 3.51 (t, 2H), 2.61 (t, 2H), 1.4 (s, 9H).

Preparation 23b": tert-Butyl 5-({6-[(5-{[4-(prop-2-en-1-yloxy)phenyl]amino}pyrimidin-2-yl)oxy] hexyl}oxy)-3,4-dihydroisoquinoline-2(1H)-carboxylate The title compound is obtained in accordance with the process of Preparation 22b", replacing in Step A 2-(2-chloroethoxy)-ethanol with 6-chlorohexanol.
High-resolution mass spectroscopy (ESI+):
Empirical formula: $C_{33}H_{42}N_4O_5$
[M+H]+ calculated 575.32,
[M+H]+ measured 575.4.

Preparation 24b": tert-Butyl 5-({5-[(5-{[4-(prop-2-en-1-yloxy)phenyl]amino}pyrimidin-2-yl)oxy] pentyl}oxy)-3,4-dihydroisoquinoline-2(1H)-carboxylate The title compound is obtained in accordance with the process of Preparation 22b", replacing in Step A 2-(2-chloroethoxy)-ethanol with 6-chloropentanol.
¹H NMR (500 MHz, dmso-d6) δ ppm: 8.29 (s, 2H), 7.79 (s, 1H), 7.12 (t, 1H), 6.93 (m, 2H), 6.86 (m, 2H), 6.79 (d, 1H), 6.72 (d, 1H), 6.03 (m, 1H), 5.38/5.24 (m, 2H), 4.49 (dt, 2H), 4.45 (br., 2H), 4.24 (t, 2H), 3.98 (t, 2H), 3.53 (1, 2H), 2.61 (t, 2H), 1.78 (m, 2H), 1.78 (m, 2H), 1.56 (m, 2H), 1.41 (s, 3H).

Preparation 25b": tert-Butyl 5-{4-[(5-{[4-(prop-2-en-1-yloxy)phenyl]amino}pyrimidin-2-yl)oxy]butoxy}-3,4-dihydroisoquinoline-2(1H)-carboxylate The title compound is obtained in accordance with the process of Preparation 22b", replacing in Step A 2-(2-chloroethoxy)-ethanol with 6-chlorobutanol.
¹H NMR (500 MHz, dmso-d6) δ ppm 8.29 (s, 2H), 7.8 (s, 1H), 7.12 (t, 1H), 6.93 (d, 2H), 6.86 (d, 2H), 6.8 (d, 1H), 6.72 (d, 1H), 6.07-5.98 (m, 1H), 5.4-5.21 (m, 2H), 4.48 (dt, 2H), 4.45 (br, 2H), 4.28 (t, 2H), 4.02 (t, 2H), 3.53 (t, 2H), 2.62 (t, 2H), 1.87 (br, 4H), 1.4 (s, 9H).

Preparation 26b": tert-Butyl 3-[(2-{2-[(5-{[4-(prop-2-en-1-yloxy)phenyl]amino}-pyrimidin-2-yl)oxy] ethoxy}ethoxy)methyl]piperidine-1-carboxylate Step A: tert-Butyl 3-({2-[2-(benzyloxy)ethoxy] ethoxy}methyl)piperidine-1-carboxylate 60% sodium hydride in oil (1.6 g; 40.2 mmol) is added to a solution of tert-butyl 3-(hydroxymethyl)piperidine-1-carboxylate (7.54 g; 35 mmol) in N,N-dimethylformamide at 0°

C. The whole is then stirred for 60 minutes. After returning to ambient temperature, a solution of 2-(2-benzyloxyethoxy)ethyl-4-methylbenzenesulphonate (12.26 g, 35 mmol) in N,N-dimethylformamide (20 mL) is added. The whole is then stirred for 60 minutes and then slowly hydrolysed. After extraction with dichloromethane, the organic phases are evaporated off and the residue is purified by chromatography over silica gel using dichloromethane and methanol as eluant to obtain the title product.

$^1$H NMR (500 MHz, dmso-d6) δ ppm 7.36-7.29 (m, 4H), 7.27 (m, 1H), 4.48 (s, 2H), 4-3.77/2.7-2.36 (br, 2H), 3.75/2.74 (br+td, 2H), 3.59-3.44 (m, 8H), 3.27/3.21 (dd, 2H), 1.66/1.11 (br, 2H), 1.62 (br, 1H), 1.55/1.29 (m, 2H), 1.37 (s, 9H).

Step B: tert-Butyl 3-{[2-(2-hydroxyethoxy)ethoxy]methyl}piperidine-1-carboxylate Palladium on carbon (10% by mass) is added to a solution of the compound obtained in Step A (11.0 g; 27.95 mmol) in ethanol (85 mL). The whole is hydrogenated for 10 hours at ambient temperature under 4 bar. The reaction mixture is filtered and then concentrated to dryness to obtain the title product.

$^1$H NMR (500 MHz, dmso-d6) δ ppm 4.45 (t, 1H), 3.87/2.57 (brm+brs, 2H), 3.74/2.78 (m+m, 2H), 3.56-3.46 (m, 4H), 3.49 (m, 2H), 3.43 (t, 2H), 3.28/3.23 (dd+dd, 2H), 1.68/1.15 (m+m, 2H), 1.64 (m, 1H), 1.58/1.32 (m+m, 2H), 1.39 (s, 9H).

Step C: tert-Butyl 3-[(2-{2-[(5-bromopyrimidin-2-yl)oxy]ethoxy}ethoxy)methyl]-piperidine-1-carboxylate Caesium carbonate (17.9 g, 55 mmol) is added to a solution of the compound obtained in Step B (8.34 g, 27.5 mmol) and 5-bromo-2-chloropyrimidine (5.31 g; 27 mmol) in acetonitrile (160 mL), and then the whole is stirred for 7 hours at 85° C. After cooling, the reaction mixture is filtered and then the filtrate is concentrated. The residue is purified by chromatography over silica gel using heptane and ethyl acetate as eluants to obtain the title product.

$^1$H NMR (500 MHz, dmso-d6) δ ppm 8.75 (s, 2H), 4.4 (m, 2H), 4.04-2.27 (brm, 4H), 3.75 (m, 2H), 3.57 (t, 2H), 3.49/3.47 (m+m, 2H), 3.25/3.2 (dd+dd, 2H), 1.64/1.1 (m+m, 2H), 1.6 (m, 1H), 1.55/1.29 (m+m, 2H), 1.37 (s, 9H).

Step D: tert-Butyl 3-[(2-{2-[(5-{[4-(prop-2-en-1-yloxy)phenyl]amino}pyrimidin-2-yl)oxy]-ethoxy}ethoxy)methyl]piperidine-1-carboxylate The title compound is obtained in accordance with the process described in Step B of Preparation 2b" using the compound of the preceding step and the compound obtained in Step B of Preparation 15b".

$^1$H NMR (500 MHz, dmso-d6) δ ppm 8.29 (s, 2H), 7.81 (s, 1H), 6.94 (m, 2H), 6.86 (m, 2H), 4.33 (m, 2H), 4-3.73/2.71-2.34 (br+br., 2H), 3.73/2.74 (br+m, 2H), 3.73 (m, 2H), 3.58 (t, 2H), 3.49 (m, 2H), 3.27/3.21 (dd+dd, 2H), 1.66/1.1 (brd+br, 2H), 1.62 (br., 1H), 1.55/1.29 (m+m, 2H), 1.37 (s, 9H).

Preparation 27b": tert-Butyl 4-[(2-{2-[(5-{[4-(prop-2-en-1-yloxy)phenyl]amino}-pyrimidin-2-yl)oxy]ethoxy}ethoxy)methyl]piperidine-1-carboxylate The title compound is obtained in accordance with the process of Preparation 26b", replacing in Step A tert-butyl 3-(hydroxymethyl)piperidine-1-carboxylate with tert-butyl 4-(hydroxymethyl)piperidine-1-carboxylate.

$^1$H NMR (500 MHz, dmso-d6) δ ppm 8.29 (s, 2H), 7.82 (s, 1H), 6.94 (m, 2H), 6.86 (m, 2H), 6.03 (m, 1H), 5.38/5.24 (m+m, 2H), 4.49 (m, 2H), 4.32 (m, 2H), 3.91/2.67 (br+br., 4H), 3.73 (m, 2H), 3.57 (m, 2H), 3.49 (m, 2H), 3.23 (d, 2H), 1.67 (m, 1H), 1.61/0.98 (brd+qd, 4H), 1.37 (s, 9H).

Preparation 28b": tert-Butyl 5-[2-(methyl{2-[(5-{[4-(prop-2-en-1-yloxy)phenyl]amino}-pyrimidin-2-yl)oxy]ethyl}amino)ethoxy]-3,4-dihydroisoquinoline-2(1H)-carboxylate

Step A: 2-{[2-(Benzyloxy)ethyl](methyl)amino}ethanol

Potassium iodide (1.0 g, 6 mmol) is added to a solution of 2-chloroethoxymethylbenzene (4.6 mL; 30 mmol) and 2-(methylamino)ethanol (3.1 mL; 39 mmol) in N,N-dimethylacetamide (40 mL), and then triethylamine (5.4 mL; 39 mmol) is added. The whole is stirred at 120° C. overnight. After filtration of the precipitate, the filtrate is concentrated to dryness and then purified by chromatography over silica gel using dichloromethane and methanol as eluants to obtain the title product.

$^1$H NMR (500 MHz, dmso-d6) δ ppm 7.38-7.24 (m, 5H), 4.46 (s, 2H), 4.34 (brt, 1H), 3.51 (t, 2H), 3.45 (brt, 2H), 2.58 (t, 2H), 2.45 (t, 2H), 2.21 (s, 3H).

Step B: tert-Butyl 5-(2-{[2-(benzyloxy)ethyl](methyl)amino}ethoxy)-3,4-dihydro-isoquinoline-2(1H)-carboxylate To a solution of the compound obtained in Step A (6.28 g, 30 mmol) and of the compound obtained in Preparation 3b' (4.99 g, 20 mmol) in tetrahydrofuran (150 mL) there are added under a nitrogen atmosphere triphenylphosphine (7.87 g, 30 mmol) at 0° C. and then, dropwise, 40% diethyl azodicarboxylate solution in toluene (14 mL, 30 mmol). After returning to ambient temperature, the mixture is stirred for 1 hour. After evaporation of the solvents, the residue is taken up twice in diisopropyl ether and is then purified by chromatography over RP-18 using acetonitrile, water and ammonium carbonate as eluants to obtain the title product.

$^1$H NMR (500 MHz, dmso-d6) δ ppm 7.35-7.24 (m, 5H), 7.11 (t, 1H), 6.79 (dd, 1H), 6.72 (dd, 1H), 4.46 (s, 2H), 4.45 (s, 2H), 4.02 (t, 2H), 3.53 (t, 2H), 3.51 (t, 2H), 2.7 (t, 2H), 2.65 (t, 2H), 2.6 (t, 2H), 2.3 (s, 3H), 1.41 (s, 9H).

Step C: tert-Butyl 5-{2-[(2-hydroxyethyl)(methyl)amino]ethoxy}-3,4-dihydroisoquinoline-2(1H)-carboxylate To a solution of the compound obtained in Step B (3.88 g; 8.8 mmol) in tetrahydrofuran (50 mL) and ethanol (80 mL) there are added 4 M hydrochloric acid in dioxane (2.4 mL) and then palladium on carbon (570 mg). The mixture is hydrogenated at ambient temperature under 4 bar for 15 hours. After filtration and evaporation, the residue is dissolved in water, and then 2 M aqueous sodium hydroxide solution is added until pH=12 is reached. After extraction with ethyl acetate and evaporation of the solvents, the title product is obtained.

$^1$H NMR (400 MHz, dmso-d6) δ ppm 7.12 (t, 1H), 6.8 (dd, 1H), 6.73 (dd, 1H), 4.45 (s, 2H), 4.34 (t, 1H), 4.03 (t, 2H), 3.53 (t, 2H), 3.47 (t, 2H), 2.77 (t, 2H), 2.62 (t, 2H), 2.51 (t, 2H), 2.28 (s, 3H), 1.41 (s, 3H)

Step D: tert-Butyl 5-{2-[{2-[(5-bromopyrimidin-2-yl)oxy]ethyl}(methyl)amino]ethoxy}-3,4-dihydroisoquinoline-2(1H)-carbaoxylate The title compound is obtained in accordance with the process described in Step B of Preparation 28b" using the compound of the preceding step and 5-bromopyrimidin-2-ol.

¹H NMR (50(1 MHz, dmso-d6) δ ppm 8.72 (s, 1H), 7.11 (t, 1H), 6.78 (d. 1H), 6.72 (d, 1H), 4.45 (s, 2H), 4.38 (t, 2H), 4.03 (t, 2H), 3.49 (t, 2H), 2.84 (t, 2H), 2.83 (t, 2H), 2.57 (t, 2H), 2.35 (s, 3H), 1.41 (s, 9H)

Step E: tert-Butyl 5-[2-(methyl{2-[(5-{[4-(prop-2-en-1-yloxy)phenyl]amino}pyrimidin-2-yl)oxy]ethyl}amino)ethoxy]-3,4-dihydroisoquinoline-2(1H)-carboxylate The title compound is obtained in accordance with the process described in Step D of Preparation 26b" using the compound of the preceding step.

¹H NMR (500 MHz, dmso-d6) δ ppm 8.28 (s, 2H), 7.8 (s, 1H), 7.11 (t, 1H), 6.93 (m, 2H), 6.85 (m, 2H), 6.8 (dd, 1H), 6.72 (dd, 1H), 6.03 (m, 1H), 5.38/5.24 (dg, 2H), 4.49 (dt, 2H) 4.44 (brs, 2H), 4.32 (t, 2H), 4.04 (t, 2H), 3.5 (t, 2H), 2.84 (t, 2H). 2.83 (t, 2H), 2.59 (t, 2H), 2.35 (s, 3H), 1.4 (s, 9H).

Example 1: 6-Chloro-14-(4-hydroxyphenyl)-10,11-dimethyl-20,23-dioxa-1,10,14-triazahexacyclo[26.3.1.1~9,12~.1~15,19~.0~3,8~.0~24.29~]tetratriaconta-3,5,7,9(34),11,15(3.3),16,18,24,26,28-undecaene-2,13-dione

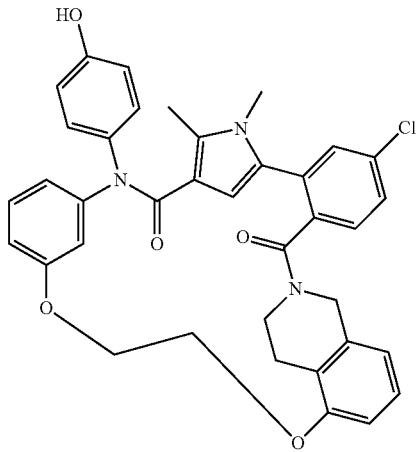 [SMILES: Cc1c2cc(n1C)-c1cc(Cl)ccc1C(=O)N1CCc3c(cccc3OCCOc3cccc(c3)N(c3ccc(O)cc3)C2=O)C1]

Step A: Ethyl 5-(5-chloro-2-{[5-(prop-2-en-1-yloxy)-3,4-dihydroisoquinolin-2(1H)-yl]-carbonyl}phenyl)-1,2-dimethyl-1H-pyrrole-3-carboxylate To a solution of the compound obtained in Preparation 1a (9.5 g; 29.5 mmol) in dichloromethane (110 mL) there are added in succession the compound obtained in Preparation 1a' (7.32 g; 32.4 mmol), 1-hydroxybenzotriazole (4.78 g; 35.4 mmol), 1,(3-dimethylaminopropyl)-3-ethylcarbodiimide hydrochloride (6.1 g; 35.4 mmol) and triethylamine (20.6 mL; 147.5 mmol). The whole is then stirred overnight at ambient temperature. The reaction mixture is diluted with a mixture of dichloromethane and water. After decantation, the organic phase is washed with saturated aqueous ammonium chloride solution and saturated aqueous sodium chloride solution and then dried over magnesium sulphate, filtered and concentrated to dryness. The residue is purified by chromatography over silica gel using petroleum ether and ethyl acetate as eluants to obtain the title product.

¹H NMR (400 MHz, dmso-d6, 300 K) δ ppm: 7.54/7.45 (2m, 3H), 7.12/7 (2t, 1H), 6.75/6.45 (2d, 1H), 6.75/6.65 (2d, 1H), 6.35/6.25 (2s, 1H), 6.05 (m, 1H), 5.4 (m, 1H), 5.25 (m, 1H), 4.55-3.95/2.95 (m, 8H), 3.45/3.21 (2s, 3H), 2.6-2.2 (m, 2H), 2.49/2.05 (2s, 3H), 1.22 (t, 3H).

IR: v: ≥C=O: 1695 cm⁻¹.

Step B: 5-(5-Chloro-2-{[5-(prop-2-en-1-yloxy)-3,4-dihydroisoquinolin-2(1H)-yl]-carbonyl}phenyl)-1,2-dimethyl-M-pyrrole-3-carboxylic acid Lithium hydroxide (1.8 g; 43.8 mmol) in solution in 50 mL of water is added to a solution of the compound obtained in Step A (10.8 g, 21.9 mmol) in methanol (100 mL). The whole is then stirred at 90° C. for 48 hours. The reaction mixture is concentrated to remove the methanol and then acidified to pH=4 by addition of 1 N aqueous hydrochloric acid solution and finally extracted with dichloromethane. The organic phase is dried over magnesium sulphate, filtered and concentrated to dryness. The title product is obtained in the form of a powder and is used in the following step without being purified.

¹H NMR (400 MHz, dmso-d6, 300 K) δ ppm: 11.55 (br. s, 1H), 7.52/7.45 (m, 3H), 7.12/7.6/7.48 (3d, 2H), 6.32/6.25 (2s, 1H), 6.05 (m, 1H), 5.4 (m, 1H), 5.25 (m, 1H), 4.8-3 (m, 6H), 3.45/3.2 (2s, 3H), 2.5 (m, 2H), 2.5/2.05 (2s, 3H).

Step C: N-(4-{[tert-Butyl(dimethyl)silyl]oxy}phenyl)-N-[3-(2-chloroethoxy)phenyl]-5-(5-chloro-2-{[5-(prop-2-en-1-yloxy)-3,4-dihydroisoquinolin-2(1H)-yl]carbonyl}phenyl)-1,2-dimethyl-1H-pyrrole-3-carboxamide 1-Chloro-N,N,2-trimethyl-prop-1-en-1-amine (0.31 mL; 2.4 mmol) is added to a solution of the compound obtained in Step B (1 g; 2.15 mmol) in dichloroethane (20 mL). The reaction mixture is stirred at ambient temperature for 2 hours, and then the compound of Preparation 1a" (1.6 g; 4.3 mmol) is added. The whole is stirred at 80° C. for 24 hours. The reaction mixture is diluted in a mixture of dichloromethane and saturated aqueous sodium hydrogen carbonate solution. After extraction of the aqueous phase with dichloromethane, the organic phases are combined, dried over magnesium sulphate, filtered and concentrated to dryness. The residue is purified by chromatography over silica gel using dichloromethane and methanol as eluants to obtain the title product.

¹H NMR (500 MHz, dmso-d6, 300 K) δ ppm: 7.5-7.25 (m, 3H), 7.2 (m, 2H), 6.95/6.65 (m, 4H), 6.85-6.6 (m, 5H), 6.05 (m, 1H), 5.4/5.25 (m, 2H), 5.35-5.2 (m, 1H), 4.8-3.9 (m, 2H), 4.5 (m, 2H), 4.15 (m, 2H), 3.85 (m, 2H), 3.3-2.9 (m, 2H), 3.3-3.2 (m, 3H), 2.8-2.5 (m, 2H), 2.35-2.2 (m, 3H), 0.85 (m, 9H), 0.1 (m, 6H).

Step D: N-(4-{[tert-Butyl(dimethyl)silyl]oxy}phenyl)-N-[3-(2-chloroethoxy)phenyl]-5-{5-chloro-2-[(5-hydroxy-3,4-dihydroisoquinolin-2(1H)-yl)carbonyl]phenyl}-1,2-dimethyl-1H-pyrrole-3-carboxamide 1,3-Dimethylbarbituric acid (0.49 g; 3.15 mmol) is added to a solution of the compound obtained in Step C (1.3 g; 1.57 mmol) in a mixture of dichloromethane (6 mL) and methanol (3 mL). The reaction mixture is degassed by bubbling through argon for 10 minutes, and tetrakis-(triphenylphosphine)palladium(0) (0.09 g; 0.07 mmol) is added. The whole is heated at 40° C. for 19 hours. After concentration of the methanol, the reaction mixture is diluted in a mixture of ethyl acetate and water. After decantation, the organic phase is washed with saturated aqueous sodium hydrogen carbonate solution and saturated aqueous sodium chloride solution and then dried over magnesium sulphate, filtered and concentrated to dryness. The residue is purified by chromatography over silica gel using dichloromethane and methanol as eluants to obtain the title product.

$^1$H NMR (500 MHz, dmso-d6, 300 K) δ ppm: 9.45 (m, 1H), 7.5-7.25 (m, 3H), 7.2 (m, 1H), 7-6.95 (m, 1H), 6.8-6.6 (m, 2H), 6.8-6.6 (m, 3H), 6.75-6.6 (m, 4H), 5.4-5.2 (m, 1H), 4.8-4.1 (m, 2H), 4.15 (m, 2H), 3.9 (m, 2H), 3.85 (m, 2H), 3.3-3.2 (m, 3H), 2.9-2.5 (m, 2H), 2.35-2.2 (m, 3H), 0.85 (m, 9H), 0.1 (m, 6H).

IR: ν: —OH: 3260 cm$^{-1}$; >C=O: 1624 cm$^{-1}$.

Step E: N-(4-{[tert-Butyl(dimethyl)silyl]oxy}phenyl)-5-{5-chloro-2-[(5-hydroxy-3,4-dihydroisoquinolin-2(1H)-yl) carbonyl]phenyl}-N-[3-(2-iodoethoxy)phenyl]-1,2-dim ethyl-1H-pyrrole-3-carboxamide Sodium iodide (0.35 g; 2.34 mmol) is added to a solution of the compound obtained in Step D (0.88 g; 1.17 mmol) in acetone (15 mL). The reaction mixture is stirred at 80° C. for 24 hours. After filtration of the reaction mixture, the filtrate is concentrated. The residue obtained is taken up in a mixture of ethyl acetate and water. After extraction of the aqueous phase with ethyl acetate, the organic phases are combined, dried over magnesium sulphate, filtered and concentrated to dryness. The residue obtained is used directly in the following step without being purified.

Step F: 14-(4-{[tert-Butyl(dimethyl)silyl]oxy}phenyl)-6-chloro-10,11-dimethyl-20,23-dioxa-1,10,14-triazahexacyclo[26.3.1.1~9,12~.1~15,19~.0~3,8~.0~24,29~]tetratriaconta-3,5,7,9(34),11,15(33),16,18,24,26,28-undecaene-2,13-dione Caesium carbonate (0.36 g; 1.12 mmol) is added in three portions, at one hour intervals and at ambient temperature, to a solution of the compound obtained in Step E (0.98 g; 1.12 mmol) in acetonitrile (112 mL). The reaction mixture is then heated at 50° C. for 4 hours before being concentrated. The residue obtained is taken up in a mixture of dichloromethane and water. After decantation, the organic phase is washed with water and saturated aqueous sodium chloride solution and then dried over magnesium sulphate, filtered and concentrated. The residue obtained is used directly in the following step without being purified.

Step G: 6-Chloro-14-(4-hydroxyphenyl)-10,11-dimethyl-20,23-dioxa-1,10,14-triazahexacyclo[26.3.1.1~9,12~.1~15,19~.0~3,8~.0~24,29~]tetratriaconta-3,5,7,9(34),11,15(33),16,18,24,26,28-undecuene-2,13-dione 1 N Tetrabutylammonium fluoride solution in tetrahydrofuran (1 mL; 1.01 mmol) is added to a solution of the compound obtained in Step F (0.5 g; 0.67 mmol) in tetrahydrofuran (10 mL). The whole is stirred at ambient temperature for 1 hour. The reaction mixture is then diluted in a mixture of dichloromethane and water. After decantation, the organic phase is washed with water and saturated aqueous sodium chloride solution and then dried over magnesium sulphate, filtered and concentrated. The residue so obtained is purified by chromatography over silica gel using dichloromethane and ammonia in methanol as eluants, followed by chromatography over a chiral IC column using acetonitrile, isopropanol and diethylamine. The solid so obtained is dissolved in a water/acetonitrile mixture, filtered and then lyophilised.

High-resolution mass spectroscopy (ESI+):

Empirical formula: $C_{37}H_{32}ClN_3O_5$

[M+H]+ calculated 634.2103,

[M+H]+ measured 634.2102.

Example 2: 6-Chloro-14-(4-hydroxyphenyl)-10,11-dimethyl-20,24-dioxa-1,10,14-triazahexacyclo[27.3.1.1~9,12~.1~15,19~.0~3,8~.0~25,30~]pentatriaconta-3,5,7,9(35),11,15(34),16,18,25,27,29-undecaene-2,13-dione

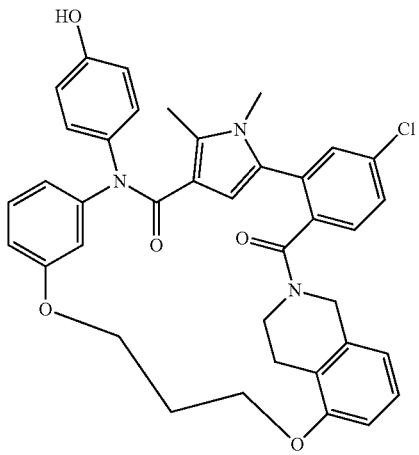 [SMILES: Cc1c2cc(n1C)-c1cc(Cl)ccc1C(=O)N1CCc3c(cccc3OCCCOc3cccc(c3)N(c3ccc(O)cc3)C2=O)C1]

The title compound is obtained in accordance with the process of Example 1 using the acid of Preparation 1a and the compound of Preparation 1a' in Step A, as well as the compound of Preparation 2a" in Step C.

Elemental microanalysis: (% theoretical: measured)

% C=70.42: 69.92; % H=5.29: 5.00; % N=6.48: 6.48,

High-resolution mass spectroscopy (ESI+):

Empirical Formula: $C_{38}H_{34}ClN_3O_5$

[M+H]+ calculated 648.2159,

[M+H]+ measured 648.2260.

Example 3: 6-Chloro-14-(4-hydroxyphenyl)-10,11-dimethyl-20,25-dioxa-1,10,14-triazahexacyclo[28.3.1.1~9,12~.1~15,19~.0~3,8~.0~26,31~]hexatriaconta-3,5,7,9(36),11,15(35),16,18,26,28,30-undecaene-L 3-dione

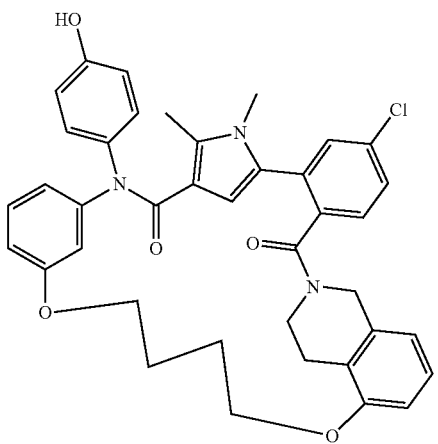 [SMILES: Cc1c2cc(n1C)-c1cc(Cl)ccc1C(=O)N1CCc3c(cccc3OCCCCOc3cccc(c3)N(c3ccc(O)cc3)C2=O)C1]

The title compound is obtained in accordance with the process of Example 1 using the acid of Preparation 1a and the compound of Preparation 1a' in Step A, as well as the compound of Preparation 3a" in Step C.

Elemental microanalysis: (% theoretical: measured)
% C=70.74: 70.22% H=5.48: 5.37; % N=6.35: 6.27.
High-resolution mass spectroscopy (ESI+):
Empirical formula: $C_{39}H_{36}ClN_3O_5$
[M+H]+ calculated 662.2416,
[M+H]+ measured 662.2422.

Example 4: 6-Chloro-14-(4-hydroxyphenyl)-10,11-dimethyl-2,13-dioxo-20,23-dioxa-1,10,14-triazahexacyclo[26.3.1.1~9,12~.1~5,19~.0~3,8~.0~24,29~]tetratriaconta-3,5,7,9(34),11,15(33),16,18,24,26,28-undecaene-17-carbonitrile

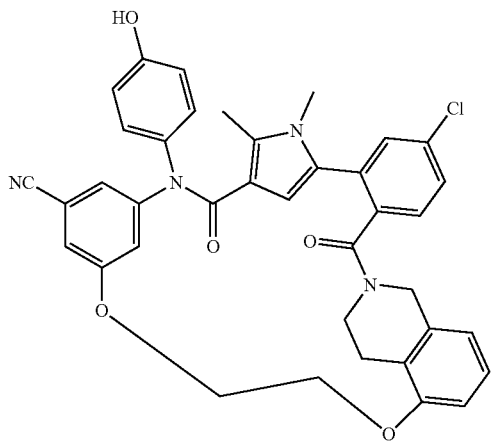 [SMILES: Cc1c2cc(n1C)-c1cc(Cl)ccc1C(=O)N1CCc3c(cccc3OCCOc3cc(C#N)cc(c3)N(c3ccc(O)cc3)C2=O)C1]

The title compound is obtained in accordance with the process of Example 1 using the acid of Preparation 1a and the compound of Preparation 1a' in Step A, as well as the compound of Preparation 4a" in Step C.

Elemental microanalysis: (% theoretical: measured)
% C=69.24: 68.29; % H=4.74: 4.68; % N=8.50: 8.70; % Cl=5.38: 5.33.
High-resolution mass spectroscopy (ESI+):
Empirical formula: $C_{38}H_{31}ClN_4O_5$
[M+H]+ calculated 659.2057.
[M+H]+ measured 659.2056.

Example 5: 6-Chloro-14-(4-hydroxyphenyl)-10,11-dimethyl-2,13-dioxo-20,24-dioxa-1,10,14-triazahexacyclo[27.3.1.1~9,12~.1~15,19~.0~3,8~.0~25,30~]pentatriaconta-3,5,7,9(35),11,15(34),16,18,25,27,29-undecaene-17-carbonitrile

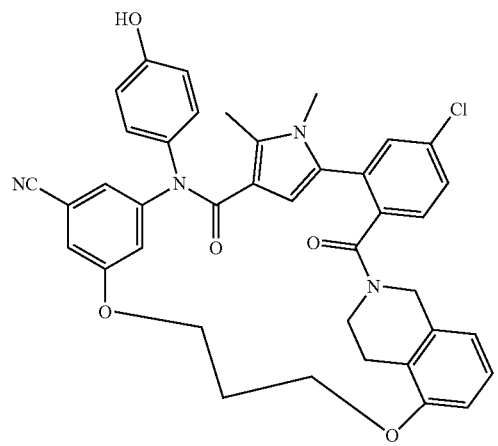 [SMILES: Cc1c2cc(n1C)-c1cc(Cl)ccc1C(=O)N1CCc3c(cccc3OCCCOc3cc(C#N)cc(c3)N(c3ccc(O)cc3)C2=O)C1]

The title compound is obtained in accordance with the process of Example 1 using the acid of Preparation 1a and the compound of Preparation 1a' in Step A, as well as the compound of Preparation 5a" in Step C.

High-resolution mass spectroscopy (ESI+):
Empirical formula: $C_{39}H_{33}ClN_4O_5$
[M+H]+ calculated 673.2212,
[M+H]+ measured 673.2211.

Example 6: 11-Chloro-4-(4-hydroxyphenyl)-1,7,8-trimethyl-4,16,17,23,24,25-hexahydro-1H,14H-15,18-methano-6,9-(metheno)dibenzo[b,h]pyrazolo[4,3-p]-[1,6,11,15]oxatriazacycloicosine-5,14(8H)-dione

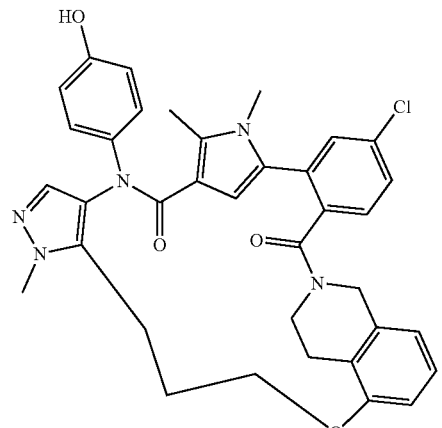

Step A: N-(4-{[tert-Butyl(dimethyl)silyl]
oxy}phenyl)-5-(5-chloro-2-{[5-(prop-2-en-1-yloxy)-
3,4-dihydroisoquinolin-2(1H)-yl]carbonyl}phenyl)-
N-[5-(3-chloropropyl)-1-methyl-1H-pyrazol-4-yl]-1,
2-dimethyl-1H-pyrrole-3-carboxamide Oxalyl chloride (0.28 mL; 3.2 mmol) is added to a solution of the compound obtained in Step B of Example 1 (0.75 g; 1.6 mmol) in dichloroethane (40 mL). The reaction mixture is stirred at ambient temperature for 1 hour and then concentrated. The residue is taken up in dichloroethane and then concentrated, this operation being carried out twice. The final residue is taken up in dichloroethane (20 mL) and is then added to a solution of the compound of Preparation 6a'' (0.61 g; 1.6 mmol) and pyridine (0.4 mL; 4.8 mmol) in dichloroethane (10 mL). The whole is stirred at 110° C. for 16 hours. The reaction mixture is concentrated and then the residue is taken up in a mixture of dichloromethane and saturated aqueous sodium hydrogen carbonate solution. After extraction of the aqueous phase with dichloromethane, the organic phases are combined, dried over magnesium sulphate, filtered and concentrated to dryness. The residue is purified by chromatography over silica gel using dichloromethane and ethyl acetate as eluants to obtain the title product.

$^1$H NMR (400 MHz, dmso-d6, 300 K) δ ppm: 7.5-7.25 (m, 3H), 7.2-7.1 (m, 1H), 7.15 (m, 1H), 7.15-6.93 (m, 2H), 6.82-6.7 (m, 2H), 6.8 (m, 1H), 6.62-6.5 (m, 1H), 6.08 (m, 1H), 5.5-5.2 (m, 2H), 5.38-5.2 (m, 1H), 4.75-2.9 (m, 2H), 4.55 (m, 2H), 4.25-3.9 (m, 2H), 3.73 (m, 3H), 3.55 (m, 2H), 3.3-3.15 (m, 3H), 2.7-2.3 (m, 2H), 2.6 (m, 2H), 2.3-2.15 (m, 3H), 1.6 (m, 2H), 0.8 (m, 9H), 0.1 (m, 6H).

Step B: 11-Chloro-4-(4-hydroxyphenyl)-1,7,8-trimethyl-4,16,17,23,24,25-hexahydro-1H,14H-15,18-methano-6,9-(metheno)dibenzo[b,h]pyrazolo[4,3-p][1,6,11,15]oxatriaza-cycloicosine-5,14(8H)-dione The title compound is obtained in accordance with the processes described in Steps D, E, F and G of Example 1, using the compound of the preceding step as starting material.
Elemental microanalysis: (% theoretical: measured)
% C=67.97: 68.05; % H=5.39: 5.25; % N=11.01: 10.77.
High-resolution mass spectroscopy (ESI+):
Empirical formula: $C_{36}H_{34}ClN_5O_4$
[M+H]+ calculated 636.2372,
[M+H]+ measured 636.2369, Example 7: 6-Chloro-14-(4-hydroxyphenyl)-10,11,
33-trimethyl-2,13-dioxo-23-oxa-1,10,14,18-tetraaza-
hexacyclo[26.3.1.1~9,12~.1~15,18~.0~3,8~.0~24,
29~]tetratriaconta-3,5,7,9(34),11,15(33),16,24,26,
28-decaene-17-carbonitrile

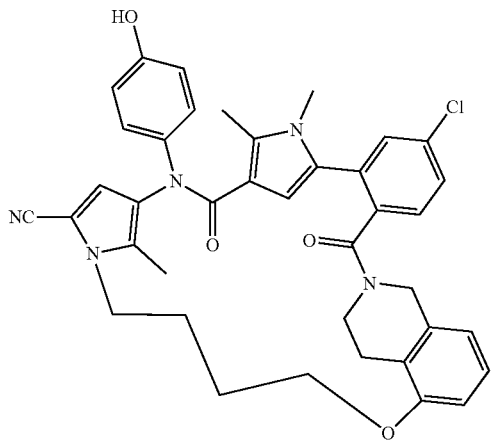 [SMILES: Cc1c2cc(n1C)-c1cc(Cl)ccc1C(=O)N1CCc3c(cccc3OCCCCn3c(C#N)cc(c3C)N(c3ccc(O)cc3)C2=O)C1]

The title compound is obtained in accordance with the process of Example 6 using the acid obtained in Step B of Example 1 and the amine of Preparation 7a''.
Elemental microanalysis: (% theoretical: measured)
% C=69.48: 69.01; % H=5.38: 5.34; % N=10.39: 10.19.
High-resolution mass spectroscopy (ESI+):
Empirical formula: $C_{39}H_{36}ClN_5O_4$
[M+H]+ calculated 674.2529,
[M+H]+ measured 674.2515.

Example 8: 6-Chloro-14-(4-hydroxyphenyl)-10,11,
32-trimethyl-2,13-dioxo-22-oxa-1,10,14,18-tetraaza-
hexacyclo[25.3.1.1~9,12~.1~15,18~.0~3,8~.0~23,
28~]tritriaconta-3,5,7,9(33),11,15(32),16,23,25,27-
decaene-17-carbonitrile

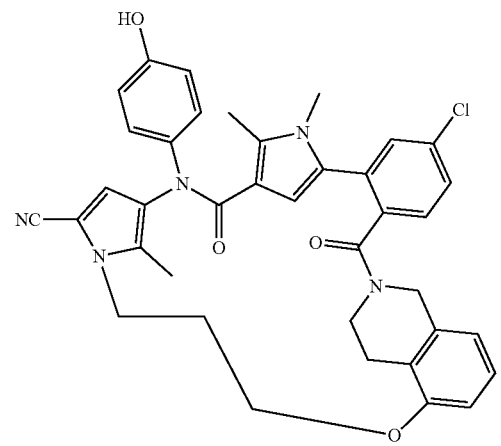 [SMILES: Cc1c2cc(n1C)-c1cc(Cl)ccc1C(=O)N1CCc3c(cccc3OCCCn3c(C#N)cc(c3C)N(c3ccc(O)cc3)C2=O)C1]

The title compound is obtained in accordance with the process of Example 6 using the acid obtained in Step B of Example 1 and the amine of Preparation 8a''.
High-resolution mass spectroscopy (ESI+):
Empirical formula: $C_{38}H_{34}ClN_5O_4$
[M+H]+ calculated 660.2372,
[M+H]+ measured 660.2377.

Example 9: 6-Chloro-14-(4-hydroxyphenyl)-10,11-
dimethyl-2,13-dioxo-23-oxa-1,10,14-triazahexacyclo
[26.3.1.1~9,12~.1~15,19~.0~3,8~.0~24,29~]tetra-
triaconta-3,5,7,9(34),11.15 (33),16,18,24,26,28-
undecaene-17-carbonitrile

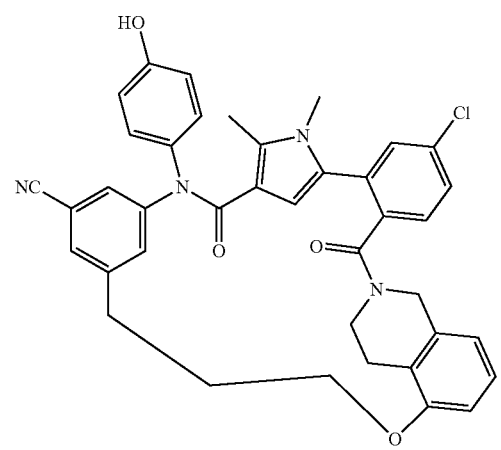 [SMILES: Cc1c2cc(n1C)-c1cc(Cl)ccc1C(=O)N1CCc3c(cccc3OCCCc3cc(C#N)cc(c3)N(c3ccc(O)cc3)C2=O)C1]

The title compound is obtained in accordance with the process of Example 6 using the acid obtained in Step B of Example 1 and the amine of Preparation 9a".

High-resolution mass spectroscopy (ESI+):
Empirical formula: $C_{39}H_{33}ClN_4O_4$
[M+H]+ calculated 657.2263,
[M+H]+ measured 657.2267.

Example 10: 11-Chloro-4-(4-hydroxyphenyl)-1,7,8-trimethyl-1,4,16,17,23,24-hexahydro-14H-15,18-methano-6,9-(metheno)dibenzo[l,r]pyrazolo[3,4-d]-[1,6,10,15]oxatriazacyclononadecin-5(8H)-one hydrochloride

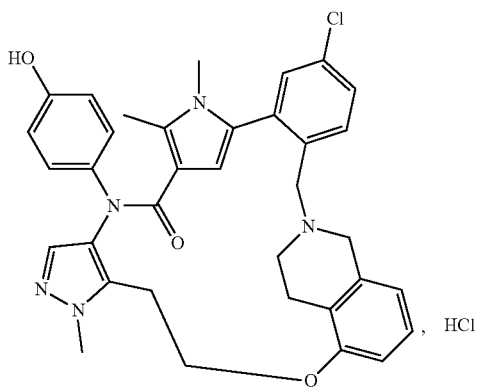 [SMILES: Cc1c2cc(n1C)-c1cc(Cl)ccc1CN1CCc3c(cccc3OCCc3c(cnn3C)N(c3ccc(O)cc3)C2=O)C1 ; Cl]

Step A: Ethyl 5-(5-chloro-2-{[5-(prop-2-en-1-yloxy)-3,4-dihydroisoquinolin-2(1H)-yl]methyl}phenyl)-1,2-dimethyl-1H-pyrrole-3-carboxylate To a solution of the compound obtained in Step B of Preparation 1a (2 g; 6.54 mmol) in dichloromethane (25 mL) there are added in succession the compound obtained in Preparation 1a' (1.5 g: 6.54 mmol) and sodium triacetoxyborohydride (2.2 g; It) mmol). The whole is then stirred overnight at ambient temperature. The reaction mixture is poured onto a mixture of water and ammonium chloride. After decantation, the organic phase is dried over sodium sulphate, filtered and concentrated to dryness. The residue is purified by chromatography over silica gel using heptane and ammonia in ethanol as eluants to obtain the title product.

$^1$H NMR (400 MHz, dmso-d6, 300 K) δ ppm: 7.6 (d, 1H), 7.47 (dd, 1H), 7.3 (d, 1H), 7.03 (t, 1H), 6.74 (d, 1H), 6.57 (d, 1H), 6.43 (s, 1H), 6.03 (m, 1H), 5.3 g (m, 1H). 5.23 (m, 1 H), 4.54 (m, 2H), 4.16 (quad, 2H), 3.42 (s, 2H), 3.4 (s, 2H), 3.22 (s, 3H), 2.64 (m, 2H), 2.56 (m, 2H), 2.49 (s, 3H), 1.25 (t, 3H).

IR: ν: >C=O: 1692 cm$^{-1}$; >C—O—C<: 1063 cm$^{-1}$

Step B: 5-(5-Chloro-2-{[5-(prop-2-en-1-yloxy)-3,4-dihydroisoquinolin-2(1H)-yl]methyl}phenyl)-1,2-dimethyl-1H-pyrrole-3-carboxylic acid 1 N aqueous lithium hydroxide solution (13 mL; 13.1 mmol) is added to a solution of the compound obtained in Step A (2.1 g; 4.4 mmol) in dioxane (12 mL). The whole is stirred under microwave (300 W) at 120° C. for 4.5 hours. The reaction mixture is poured onto a mixture of 1 N aqueous hydrochloric acid solution and ice. The product is extracted with dichloromethane. The organic phases are combined, dried over sodium sulphate, filtered and concentrated to provide the title product without further purification.

$^1$H NMR (400 MHz, dmso-d6, 300 K) δ ppm: 7.61 (d, 1H), 7.45 (dd, 1H), 7.27 (br, s, 1H), 7.03 (t, 1H), 6.73 (d, 1H); 6.57 (d, 1H), 6.33 (s, 1H), 6.04 (m, 1H), 5.39 (d, 1H), 5.23 (d, 1H), 4.53 (m, 2H), 3.45 (s, 2H), 3.39 (s, 2H), 3.2 (s, 3H), 2.63 (m, 2H), 2.55 (m, 2H), 2.5 (s, 3H).

IR: ν: —OH: 3300–2200 cm$^{-1}$; >C=O: 1661 cm$^{-1}$; >C—O—C<: 1258 cm$^{-1}$.

Step C: N-(4-{[tert-Butyl(dimethyl)silyl]oxy}phenyl)-5-(5-chloro-2-{[5-(prop-2-en-1-yloxy)-3,4-dihydroisoquinolin-2(1H)-yl]methyl}phenyl)-1,2-dimethyl-N-{1-methyl-5-[2-(tetrahydro-2H-pyran-2-yloxy)ethyl]-1H-pyrazol-4-yl}-1H-pyrrole-3-carboxamide 1-Chloro-N,N,2-trimethyl-prop-1-en-1-amine (0.59 mL; 4.87 mmol) is added to a solution of the compound obtained in Step B (2 g; 4.43 mmol) in dichloroethane (50 mL). The reaction mixture is stirred at ambient temperature for 2 hours and then the compound of Preparation 10a" (3.2 g; 7.4 mmol) and pyridine (1.8 mL; 22.1 mmol) are added. The whole is stirred at 80° C. for 24 hours. The reaction mixture is poured onto a mixture of saturated aqueous sodium hydrogen carbonate solution and ice. After extraction of the aqueous phase with dichloromethane, the organic phases are combined, dried over sodium sulphate, filtered and concentrated to dryness. The residue is purified by chromatography over silica gel using dichloromethane and isopropanol as eluants to obtain the title product.

$^1$H NMR (500 MHz, dmso-d6, 300 K) δ ppm: 7.45 (d, 1H), 7.3 (dd, 1H), 7.15 (s, 1H), 7.05 (d, 1H), 7.02 (d, 1H), 6.97 (t, 1H), 6.9/6.6 (ab, 4H), 6.5 (d, 1H), 5.95 (m, 1H), 5.3 (s, 1H), 5.3/5.15 (m, 2H), 4.48 (m, 2H), 4.3 (m, 1H), 3.65 (s, 3H), 3.5-3.25 (m, 6H), 3.2-3.1 (m, 4H), 3.08 (s, 3H), 2.8-2.5 (m, 2H), 2.5 (m, 2H), 2.3 (s, 3H), 1.6-1.2 (m, 6H), 0.87-0.8 (s, 9H), 0.1-0 (s, 6H).

Step D: N-(4-{[tert-Butyl(dimethyl)silyl]oxy}phenyl)-5-{5-chloro-2-[(5-hydroxy-3,4-dihydroisoquinolin-2(1H)-yl)methyl]phenyl}-N-[5-(2-hydroxyethyl)-1-methyl-1H-pyrazol-4-yl]-1,2-dimethyl-1H-pyrrole-3-carboxamide The title compound is obtained in two steps. The compound of Step C is first subjected to a deprotection reaction in accordance with the process described in Step D of Example 1 and is used in the following step.

To a solution of the product so obtained (430 mg; 0.52 mmol) in methanol (15 mL) there is added pyridine para-toluenesulphonate (140 mg; 0.52 mmol). The reaction mixture is stirred at 80° C. overnight and then concentrated to dryness. The residue is purified by chromatography over silica gel using dichloromethane and methanol as eluants to obtain the title product.

$^1$H NMR (500 MHz, dmso-d6, 300 K) δ ppm: 9.2 (s, 1H), 4.62 (s, 1H), 7.44 (d, 1H), 7.3 (d, 1H), 7.15 (s, 1H), 7.02 (s, 1H), 6.94-6.6 (m, 4H), 6.8 (t, 1H), 6.5 (d, 1H), 6.35 (d, 1H), 5.7-5.3 (s, 1H), 3.65 (s, 3H), 3.3 (m, 2H), 3.2 (m, 2H), 3.1 (m, 2H), 3.05 (s, 3H), 2.6 (m, 2H), 2.5 (m, 2H), 2.48 (m, 2H), 2.3 (s, 3H), 0.8 (s, 9H), 0.15 (s, 6H).

Step E: 11-Chloro-4-(4-hydroxyphenyl)-1,7,8-trimethyl-1,4,16,17,23,24-hexahydro-14H-15,18-methano-6,9-(metheno)dibenzo[l,r]pyrazolo[3,4-d][1,6,10,15]oxatriazacyclonona-decin-5(8H)-one hydrochloride A solution of the compound obtained in Step D (250 mg; 0.34 mmol) in a mixture of tetrahydrofuran (80 mL) and toluene (80 mL) is degassed with argon for 10 minutes. Cyanomethylene tri-n-butylphosphorane (0.18 mL; 0.75 mmol) is added thereto, and then the whole is sealed and stirred at 110° C. for 48 hours. The reaction mixture is concentrated and then diluted in a mixture of ethyl acetate and water. After decantation, the organic phase is washed with water and saturated aqueous sodium hydrogen carbonate solution, dried over magnesium sulphate, filtered and concentrated to dryness. The residue is purified by chromatography over silica gel using ammonia in dichloromethane as eluant and is then used in the following step.

To a solution of the product obtained in methanol (5 mL) there is added 1 M potassium hydroxide solution in methanol (0.34 mL; 0.34 mmol). The reaction mixture is stirred at ambient temperature for 2 hours and is then poured onto a mixture of saturated aqueous sodium hydrogen carbonate solution and ice. After extraction of the aqueous phase with dichloromethane, the organic phases are combined, dried over sodium sulphate, filtered and concentrated to dryness. The residue is purified by chromatography over silica gel using dichloromethane and ammonia in ethanol as eluants. The solid so obtained is dissolved in a mixture of 1 N aqueous hydrochloric acid solution and acetonitrile, filtered and then lyophilised to obtain the title product.

High-resolution mass spectroscopy (ESI+):

Empirical formula: $C_{35}H_{34}ClN_5O_3 \cdot HCl$

[M+H]+ calculated 608.2423,

[M+H]+ measured 608.2425.

Example 11: 11-Chloro-4-(4-hydroxyphenyl)-1,7,8-trimethyl-4,16,17,23,24,25-hexahydro-1H,14H-15,18-methano-6,9-(metheno)dibenzo[b,h]pyrazolo[4,3-p]-[1,6,11,15]oxatriazacycloicosin-5(8H)-one

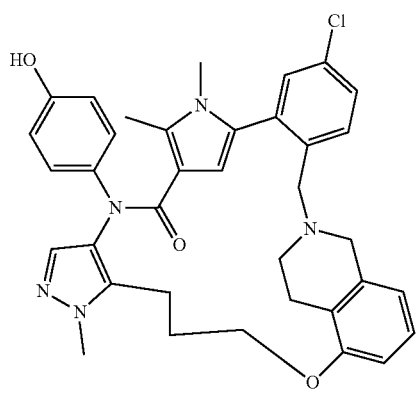 [SMILES: Cc1c2cc(n1C)-c1cc(Cl)ccc1CN1CCc3c(cccc3OCCCc3c(cnn3C)N(c3ccc(O)cc3)C2=O)C1]

Step A: N-(4-{[tert-Butyl(dimethyl)silyl]oxy}phenyl)-5-(5-chloro-2-{[5-(prop-2-en-1-yloxy)-3,4-dihydroisoquinolin-2(1H)-yl]methyl}phenyl)-N-[5-(3-chloropropyl)-1-methyl-1H-pyrazol-4-yl]-1,2-dimethyl-1H-pyrrole-3-carboxamide The title compound is obtained in accordance with the process described in Step A of Example 6, using the acid of Step B of Example 10 and the amine of Preparation 6a''.

$^1$H NMR (500 MHz, dmso-d6, 300 K) δ ppm: 7.53 (d, 1H), 7.41 (dd, 1H), 7.28 (s, 1H), 7.1 (d, 1H), 7.05 (t, 1H), 6.99 (d, 2H), 6.75 (d, 1H), 6.69 (d, 2H), 6.59 (d, 1H), 6.04 (m, 1H), 5.4/5.24 (m+m, 1+1H), 5.4 (s, 1H), 4.55 (d, 2H), 3.7 (s, 3H), 3.59 (t, 2H), 3.34 (s, 2H), 3.22 (br. s, 2H), 3.15 (s. 3H), 2.63 (m, 2H), 2.62 (m, 2H), 2.5 (m, 2H), 2.38 (s, 3H), 1.73 (m, 2H), 0.87 (s, 9H), 0.08 (s, 6H).

Step B: N-(4-{[tert-Butyl(dimethyl)silyl]oxy}phenyl)-5-{5-chloro-2-[(5-hydroxy-3,4-dihydroisoquinolin-2(1H)-yl)methyl]phenyl}-N-[5-(3-chloropropyl)-1-methyl-1H-pyrazol-4-yl]-1,2-dimethyl-1H-pyrrole-3-carboxamide The title compound is obtained in accordance with the process described in Step D of Example 1 starting from the compound obtained in the preceding step.

$^1$H NMR (500 MHz, dmso-d6, 300 K) δ ppm 7.55 (d, 1H), 7.4 (dd, 1H), 7.3 (s, 1H), 7.1 (d, 1H), 7 (d, 2H), 6.9 (t, 1H), 6.7 (d, 2H), 6.6 (d, 1H), 6.4 (d, 1H), 5.4 (s, 1H), 3.7 (s, 3H), 3.6 (t, 2H), 3.3 (s, 2H), 3.2 (br. s, 2H), 3.15 (s, 3H), 2.6 (m, 2H), 2.55 (m, 2H), 2.5 (m, 2H), 2.35 (s, 3H), 1.7 (quint, 2H), 0.85 (s, 9H), 0.1 (s, 6H).

IR: ν: —OH: 3500–2500 cm$^{-1}$; >C=O: 1635 and 1622 cm$^{-1}$.

Step C: N-(4-{[tert-Butyl(dimethyl)silyl]oxy}phenyl)-5-{5-chloro-2-[(5-hydroxy-3,4-dihydroisoquinolin-2(1H)-yl)methyl]phenyl}-N-[5-(3-iodopropyl)-1-methyl-1H-pyrazol-4-yl]-1,2-dimethyl-1H-pyrrole-3-carboxamide The title compound is obtained in accordance with the process described in Step E of Example 1 starting from the compound obtained in the preceding step. The residue obtained is used directly in the following step without being purified.

Step D: 11-Chloro-4-(4-hydroxyphenyl)-1,7,8-trimethyl-4,16,17,23,24,25-hexahydro-1H,14H-15,18-methano-6,9-(metheno)dibenzo[b,h]pyrazolo[4,3-p][1,6,11,15]-oxatriazacycloicosin-5(8H)-one The title compound is obtained in accordance with the processes described in Steps F and G of Example 1 starting from the compound obtained in the preceding step.

High-resolution mass spectroscopy (ESI+):

Empirical formula: $C_{36}H_{36}ClN_5O_3$

[M+H]+ calculated 622.2579,

[M+H]+ measured 622.2573.

Example 12: Disodium 4-[6-Chloro-17-cyano-10,11-dimethyl-2,13-dioxo-20,23-dioxa-1,10,14-triaza-hexacyclo[26.3.1.1~9,12~.1~15,19~.0~3,8~.0~24,29~]tetratriaconta-3,5,7,9(34),11,15(33),16,18,24,26,28-undecaen-14-yl]phenyl phosphate

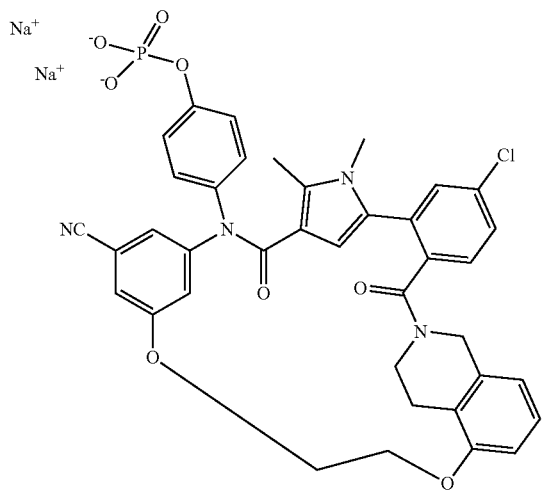

To a solution of the compound of Example 4 (75 mg: 0.113 mmol) in dichloromethane (1.5 mL) there are added 1,8-diazabicyclo[5.4.0]undec-7-ene (34 μL; 0.227 mmol) and then bis(dimethylamino)phosphoryl chloride (16.5 μL; 0.113 mmol). The reaction mixture is stirred at ambient temperature for 16 hours and is then diluted in a mixture of ethyl acetate and saturated aqueous sodium hydrogen carbonate solution. After extraction with dichloromethane, the organic phases are combined and dried over magnesium sulphate, filtered and concentrated to dryness.

To a solution of the product obtained in acetonitrile (2 mL) there is added a solution of trifluoroacetic acid (1 mL) in water (0.5 mL). The reaction mixture is stirred at ambient temperature for 24 hours and then concentrated to dryness. The residue obtained is taken up in acetonitrile, and then saturated aqueous sodium bicarbonate solution is added dropwise to pH=7. The mixture is concentrated to dryness and then taken up in ethanol and filtered. The filtrate is concentrated and then the residue obtained is purified by chromatography over Oasis® phase using acetonitrile and water as eluants before being lyophilised to obtain the title product.

High-resolution mass spectroscopy (ESI+):
Empirical formula: $C_{38}H_{30}ClN_4O_8P.2Na$
[M+H]+ calculated 783.1358,
[M+H]+ measured 783.1361.

Example 13: 12-Chloro-5-(4-hydroxyphenyl)-8,9-dimethyl-6,15-dioxo-6,9,22,23-tetrahydro-5H,15H,17H-16,22-methano-7,10-(metheno)tribenzo[b,j,o][1,4,8,13]oxa-triazacyclooctadecine-3-carbonitrile

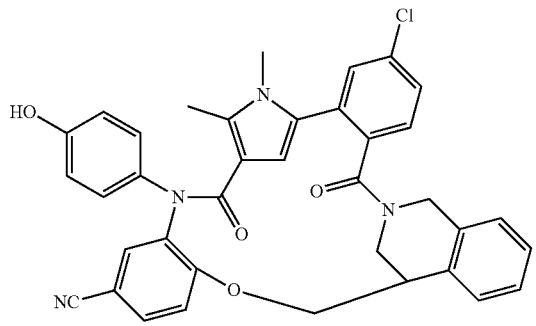 [SMILES: Cc1c2cc(n1C)-c1cc(Cl)ccc1C(=O)N1Cc3ccccc3C(COc3ccc(C#N)cc3N(c3ccc(O)cc3)C2=O)C1]

Step A: Ethyl 5-(2-{[4-({[tert-butyl(dimethyl)silyl]oxy}methyl)-3,4-dihydroisoquinolin-2(1H)-yl]carbonyl}-5-chlorophenyl)-1,2-dimethyl-1H-pyrrole-3-carboxylate To a solution of Preparation 2a' (2.95 g; 18.1 mmol) in dichloromethane (30 mL) there are added imidazole (3.08 g; 45.25 mmol), 4-(dimethyl)-amino-pyridine (0.11 g; 0.9 mmol) and chloro-tert-butyl-dimethylsilane (3.28 g; 21.72 mmol). The whole is stirred at ambient temperature for 2 hours. After hydrolysis, the organic phase is washed with water and dried over magnesium sulphate, filtered and concentrated to dryness. The residue is purified by chromatography over silica gel using dichloromethane and methanol as eluants and is then used in the following step without being purified.

The title compound is obtained in accordance with the process described in Step A of Example 1, using the above intermediate residue and the acid of Preparation 1a.

$^1$H NMR (500 MHz, dmso-d6, 300 K) δ ppm: 7.6-7.35 (m, 3H), 7.2-6.85 (m, 4H), 6.45-5.9 (4s, 1H), 5.05-2.7 (m, 4H), 4.1/3.95 (2m, 2H), 3.85-3.2 (m, 2H), 3.45/3.3 (2s, 3H), 2.9/2.6 (2m, 1H), 2.45/2.35/2.2 (3s, 3H), 1.2/1.05 (2m, 3H), 0.85/0.7 (2br. s, 9H), 0.05-0 (3br. s, 6H)

IR: v: >C=O: 1697 and 1634 cm$^{-1}$.

Step B: 5-(5-Chloro-2-{[4-(hydroxymethyl)-3,4-dihydroisoquinolin-2(1H)-yl]carbonyl}-phenyl)-1,2-dimethyl-1H-pyrrole-3-carboxylic acid The title compound is obtained in accordance with the process described in Step B of Example 1 using the ester obtained in the preceding step.

$^1$H NMR (500 MHz, dmso-d6, 300 K) δ ppm: 7.6-7.4 (m, 3H), 7.2-7 (m, 4H), 6.5-6.2 (4br. s, 1H), 5.05/4.3-3.95 (5m, 2H), 4.3-2.8 (6m, 2H), 3.75-2.8 (m, 2H), 3.47/3.3 (2s, 3H), 2.85/2.6 (3m, 1H), 2.5/2.35/2.25 (3s, 3H).

IR: v: >C=O: 1662 and 1613 cm$^{-1}$.

Step C: 5-(2-{[4-({[tert-Butyl(dimethyl)silyl]oxy}methyl)-3,4-dihydroisoquinolin-2(1H)-yl]carbonyl}-5-chlorophenyl)-1,2-dimethyl-1H-pyrrole-3-carboxylic acid To a solution of the compound obtained in Step B (3.65 g; 8.32 mmol) in acetonitrile (10 mL) there are added chloro-tert-butyl-dimethylsilane (3 g; 20 mmol) and 4-(dimethyl)-amino-pyridine (0.11 g; 0.9 mmol), and then the whole is stirred at ambient temperature for 15 minutes. 2,3,4,6,7,8,9,10-Octahydropyrimido[1,2-a]azepine (1.65 mL; 10.8 mmol) is then added dropwise at 0° C. The reaction mixture is stirred at 70° C. for 24 hours. After addition of 0.1 N aqueous hydrochloric acid solution (10 mL), the reaction mixture is stirred for 3 hours. The reaction mixture is diluted in a mixture of water and ethyl acetate. After extraction with ethyl acetate, the organic phases are combined, dried over magnesium sulphate, filtered and concentrated to dryness. The residue is purified by chromatography over silica gel using dichloromethane, methanol and acetic acid as eluants to obtain the title product.

$^1$H NMR (400 MHz, dmso-d6, 300 K) δ ppm: 7.5-7.1 (m, 7H), 6.3 (m, 1H), 3.6-3.4 (m, 2H), 3.5 (m, 4H), 3.4 (m, 3H), 3 (s, 1H), 2.5-2.3 (m, 3H), 0.9 (s, 9H), 0.1 (s, 6H).

Step D: 5-(2-{[4-({[tert-Butyl(dimethyl)silyl]oxy}methyl)-3,4-dihydroisoquinolin-2(1H)-yl]carbonyl}-5-chlorophenyl)-N-(5-cyano-2-fluorophenyl)-1,2-dimethyl-N-[4-(prop-2-en-1-yloxy)phenyl]-1H-pyrrole-3-carboxamide The compound is obtained in accordance with the process described in Step A of Example 6 using the acid obtained in the preceding step and the amine of Preparation 11a". The residue obtained is used directly in the following step without being purified.

Step E: 5-(5-Chloro-2-{[4-(hydroxymethyl)-3,4-dihydroisoquinolin-2(1H)-yl]carbonyl}-phenyl)-N-(5-cyano-2-fluorophenyl)-1,2-dimethyl-N-[4-(prop-2-en-1-yloxy)phenyl]-1H-pyrrole-3-carboxamide The title compound is obtained in accordance with the process described in Step G of Example 1, using the compound obtained in the preceding step. The residue obtained is used directly in the following step without being purified.

Step F: 12-Chloro-5-(4-hydroxyphenyl)-8,9-dimethyl-6,15-dioxo-6,9,22,23-tetrahydro-5H,15H,17H-16,22-methano-7,10-(metheno)tribenzo[b,j,o][1,4,8,13]oxatriazacyclo-octadecine-3-carbonitrile Sodium hydride (4.64 mg; 0.012 mmol) is added at 0° C. to a solution of the compound obtained in Step E (40 mg; 0.058 mmol) in tetrahydrofuran (20 mL), and then the mixture is stirred at 40° C. for 16 hours. An identical quantity of sodium hydride is added a further two times, and then the reaction mixture is stirred at 40° C. for 16 hours before being diluted in saturated aqueous ammonium chloride solution. After extraction with ethyl acetate, the organic phases are combined, washed with saturated aqueous sodium chloride solution, dried over magnesium sulphate, filtered and concentrated to dryness. The title compound is obtained in accordance with the process described in Step D of Example 1 using the above residue.

High-resolution mass spectroscopy (ESI+):

Empirical formula: $C_{17}H_{29}ClN_4O_4$

[M+H]+ calculated 629.195,

[M+H]+ measured 629.194.

Example 14: 6-Chloro-14-(4-hydroxyphenyl)-10,11-dimethyl-2,13-dioxo-20-oxa-1,10,14-triazahexacyclo[26.3.1.1~9,12~.1~15,19~.0~3,8~.0~24,29~]tetratriaconta-3,5,7,9(34),11,15(33),16,18,24,26,28-undecaene-17-carbonitrile

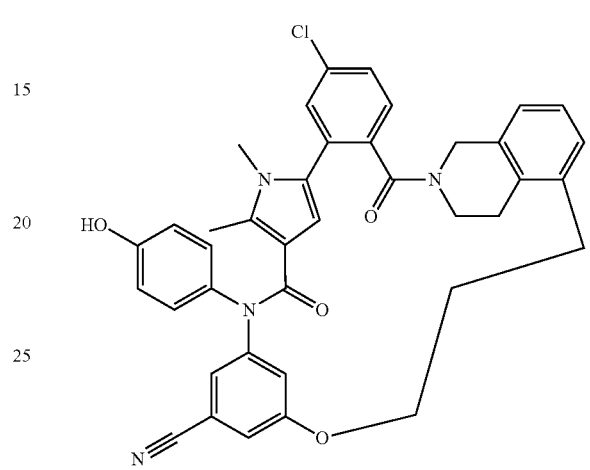

Step A: tert-Butyl 5-[3-(3-cyano-5-{[4-(prop-2-en-1-yloxy)phenyl]amino}phenoxy)-propyl]-3,4-dihydroisoquinoline-2(1H)-carboxylate 1 N tetrabutylammonium fluoride solution in tetrahydrofuran (2.45 mL; 2.45 mmol) is added to a solution of the compound of Preparation 1b" (1 g; 1.63 mmol) in tetrahydrofuran 10 mL) at 0° C. The whole is stirred at ambient temperature for 30 minutes. The reaction mixture is concentrated and then diluted in a mixture of ethyl acetate and water. After decantation, the organic phase is washed with water and with saturated aqueous sodium chloride solution and then dried over magnesium sulphate, filtered and concentrated.

To a solution of the residue obtained in acetonitrile there are added allyl bromide (142 μL; 1.63 mmol) and then caesium carbonate (0.53 g; 1.63 mmol). The whole is stirred at ambient temperature for 16 hours, and then for 2 hours at 60° C. after the addition of 0.2 equivalent of allyl bromide. The reaction mixture is concentrated and then diluted in a mixture of ethyl acetate and water. After decantation, the organic phase is washed with water and with saturated aqueous sodium chloride solution and then dried over magnesium sulphate, filtered and concentrated. The residue so obtained is purified by chromatography over silica gel using petroleum ether and ethyl acetate as eluants to obtain the title product.

$^1$H NMR (500 MHz, dmso-d6, 300 K) δ ppm: 8.24 (s, 1H), 7.1 (dd, 1H), 7.06 (dd, 2H), 7 (d, 2H), 6.94 (d, 2H), 6.77-6.6 (3dd, 3H), 6.04 (m, 1H), 5.4/5.26 (2*d, 2H), 4.54 (d, 2H), 4.47 (s, 2H), 3.96 (t, 2H), 3.52 (t, 2H), 2.76-2.64 (m, 4H), 1.92 (m, 2H), 1.42 (s, 9H).

IR: ν: >NH: 3340 cm$^{-1}$; —CN: 2225 cm$^{-1}$; >C=O: 1624 cm$^{-1}$.

Step B: tert-Butyl 5-[3-(3-{({5-[2-(tert-butoxycarbonyl)-5-chlorophenyl]-1,2-dimethyl-1H-pyrrol-3-yl}carbonyl)[4-(prop-2-en-1-yloxy)phenyl]amino}-5-cyanophenoxy)propyl]-3,4-dihydroisoquinoline-2(1H)-carboxylate 1-Chloro-NA-2-trimethyl-prop-1-en-1-amine (0.53 mL; 4 mmol) is added to a solution of the compound obtained in Preparation 1 b (0.7 g; 2 mmol) in dichloromethane (20 mL) and N,N-dimethylformamide (5 drops). The reaction mixture is stirred at ambient temperature for 1 hour and then concentrated. The residue is taken up in dichloroethane and then concentrated, this operation is carried out twice. The final residue is taken up in dichloroethane (10 mL) and is then added to a solution of the compound obtained in Step A (1.08 g; 2 mmol) and pyridine (0.48 mL; 6 mmol) in dichloroethane (10 mL). The whole is heated at 80° C. for 16 hours. The reaction mixture is diluted in a mixture of dichloromethane and saturated aqueous sodium chloride solution. After extraction of the aqueous phase with dichloromethane, the organic phases are combined, dried over magnesium sulphate, filtered and concentrated to dryness. The residue is purified by chromatography over silica gel using petroleum ether and ethyl acetate as eluants to obtain the title product.

$^1$H NMR (500 MHz, dmso-d6, 300 K) δ ppm: 7.8 (d, 1H), 7.55 (d, 1H), 7.25 (s, 1H), 7.15 (d, 2H), 7.15/7.05/7 (3s, 3H), 7.1-6.95 (m, 3H), 6.9 (d, 2H), 6 (m, 1H), 5.35/5.2 (d+d, 1+1 H), 5.25 (s, 1H), 4.55 (d, 2H), 4.45 (br. s, 2H), 4 (t, 2H), 3.5 (t, 2H), 3.15 (s, 3H), 2.7 (m, 4H), 2.45 (s, 3H), 1.9 (quint, 2H), 1.4 (s, 9H), 1.3 (s, 9H).

IR: ν: —CN: 2230 cm$^{-1}$; >C—O: 1695 cm$^{-1}$; >C=O: 1645 cm$^{-1}$.

Step C: 6-Chloro-14-(4-hydroxyphenyl)-10,11-dimethyl-2,13-dioxo-20-oxa-1,10,14-triazahexacyclo[26.3.1.1~9,12~.1~15,19~.0~3,8~.0~24,29~]tetratriaconta-3,5,7,9(34),11,15(33),16,18,24,26,28-undecaene-17-carbonitrile To a solution of the compound obtained in Step B (0.58 g; 0.67 mmol) in dioxane (15 mL) there are added triethylamine (1.38 mL; 10 mmol) and trimethylsilyl trifluoromethanesulphonate (1.8 mL; 10 mmol). The reaction mixture is stirred at reflux for 2 hours and then poured into ice-water. After extraction with ethyl acetate, the organic phases are combined, dried over magnesium sulphate, filtered and concentrated.

To a solution of the residue so obtained in dichloromethane (200 mL) there are added in succession 1-hydroxybenzotriazole (0.108 g; 0.67 mmol), 1-(3-dimethylaminopropyl)-3-ethylcarbodiimide hydrochloride (0.153 g; 0.8 mmol) and diisopropylethylamine (0.57 mL; 3.33 mmol). The whole is then stirred for 24 hours at ambient temperature. The reaction mixture is diluted with a mixture of dichloromethane and water. After decantation, the organic phase is dried over magnesium sulphate, filtered and concentrated to dryness. The residue is purified by chromatography over silica gel using dichloromethane and ethyl acetate as eluants.

To a solution of the residue so obtained in a mixture of dichloromethane (10 mL) and methanol (5 mL) there is added 1,3-dimethylbarbituric acid (0.036 g; 0.23 mmol). The reaction mixture is degassed with argon for 10 minutes, and tetrakis-(triphenylphosphine)palladium(0) (0.013 g; 0.01 mmol) is added. The reaction mixture is heated at 40° C. for 45 minutes. After concentration of the methanol, the reaction mixture is diluted in a mixture of ethyl acetate and water. After decantation, the organic phase is dried over magnesium sulphate, filtered and concentrated to dryness. The residue is purified by chromatography over Oasis® phase using acetonitrile and water as eluants. The solid so obtained is dissolved in a mixture of water and acetonitrile, filtered and then lyophilised to obtain the title product.

Elemental microanalysis: (% theoretical: measured)
% C=71.28: 70.81; % H=5.06: 4.94; % N=8.53: 8.51.
High-resolution mass spectroscopy (ESI+):
Empirical formula: $C_{39}H_{33}ClN_4O_5$
[M+H]+ calculated 673.2212,
[M+H]+ measured 673.2211.

Example 15: Chloro-14-(4-hydroxyphenyl)-10,11-dimethyl-23-oxa-1,10,14,17,18-pentaazahexacyclo[26.3.1.1~9,12~.1~15,18~.0~3,8~.0~24,29~]tetratriaconta-3,5, 7, 9(34),11,15(33),16,24,26,28-decaene-2,13-dione

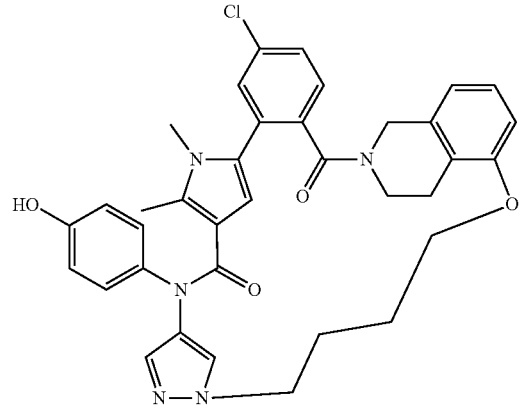 [SMILES: Cc1c2cc(n1C)-c1cc(Cl)ccc1C(=O)N1CCc3c(cccc3OCCCCn3cc(cn3)N(c3ccc(O)cc3)C2=O)C1]

Step 0.4: tert-Butyl 5-(4-{4-[({5-[2-(tert-butoxycarbonyl)-5-chlorophenyl]-1,2-dimethyl-1H-pyrrol-3-yl}carbonyl)(4-{[tert-butyl(dimethyl)silyl]oxy}phenyl)amino]-1H-pyrazol-1-yl}butoxy)-3,4-dihydroisoquinoline-2(1H)-carboxylate The title compound is obtained in accordance with the process described in Step B of Example 14, using the compound of Preparation 1b (acid) and the compound of Preparation 2b" (amine).

$^1$H NMR (400 MHz, dmso-d6, 300 K) δ ppm: 7.83 (s, 1H), 7.73 (d, 1H), 7.51 (dd, 1H), 7.15 (s, 1H), 7.14-7.06 (m, 3H), 7.1 (s, 1H), 6.82 (d, 2H), 6.73 (dd, 2H), 4.97 (s, 1H), 4.46 (s, 2H), 4.1 (t, 2H), 3.91 (t, 2H), 3.53 (t, 2H), 3.15 (s, 3H), 2.59 (t, 2H), 2.47 (s, 3H), 1.9 (m, 2H), 1.64 (m, 2H), 1.41 (s, 9H), 1.27 (s, 9H), 0.86 (s, 9H). 0.07 (s, 6H).

IR: ν: >C=O: 1695 cm$^{-1}$; >C—O: 1633 cm$^{-1}$.

Step B: 6-Chloro-14-(4-hydroxyphenyl)-10,11-dimethyl-23-oxa-1,10,14,17,18-pentaazahexacyclo[26.3.1.1~9,12~.1~15,18~.0~3,8~.0~24,29~]tetratriaconta-3,5,7,9(34),11,15(33),16,24,26,28-decaene-2,13-dione To a solution of the compound obtained in Step A (0.13 g; 0.14 mmol) in dioxane (5 mL) there are added triethylamine (0.1 mL; 0.71 mmol) and trimethylsilyl trifluoromethanesulphonate (0.13 mL; 0.71 mmol). The reaction mixture is stirred at reflux for 1 hour and then poured into ice-water. After extraction with ethyl acetate, the organic phases are combined, dried over magnesium sulphate, filtered and concentrated.

To a solution of the residue obtained in dichloromethane (85 mL) there are added in succession 1-hydroxybenzotriazole (0.046 g; 0.34 mmol), 1-(3-dimethylaminopropyl)-3-ethylcarbodiimide hydrochloride (0.065 g; 0.34 mmol) and diisopropylethylamine (0.243 mL; 1.42 mmol). The whole is then stirred for 20 hours at ambient temperature. The reaction mixture is diluted with a mixture of dichloromethane and water. After decantation, the organic phase is dried over magnesium sulphate, filtered and concentrated to dryness. The residue is purified by chromatography over silica gel using dichloromethane and methanol as eluants.

To a solution of the residue obtained in methanol (3 mL) there is added 1 N potassium hydroxide solution in methanol (0.11 mL; 0.11 mmol). The whole is then stirred for 18 hours at ambient temperature. After concentration of the methanol, the reaction mixture is diluted in a mixture of dichloromethane and water. After decantation, the organic phase is dried over magnesium sulphate, filtered and concentrated to dryness. The residue is purified by chromatography over Oasis® phase using acetonitrile and water as eluants. The solid so obtained is dissolved in a mixture of water and acetonitrile and then lyophilised to obtain the title product.

High-resolution mass spectroscopy (ESI+):
Empirical formula: $C_{36}H_{34}ClN_5O_4$
[M+H]+ calculated 636.2372,
[M+H]+ measured 636.2375.

Example 16: 11-chloro-4-(4-hydroxyphenyl)-1,7,8-trimethyl-1,4,16,17,23,24-hexahydro-14H-15,18-methano-6,9-(metheno)dibenzo[l,r]pyrazolo[3,4-d][1,6,10,15]oxatriaza-cyclononadecine-5,14(8H)-dione

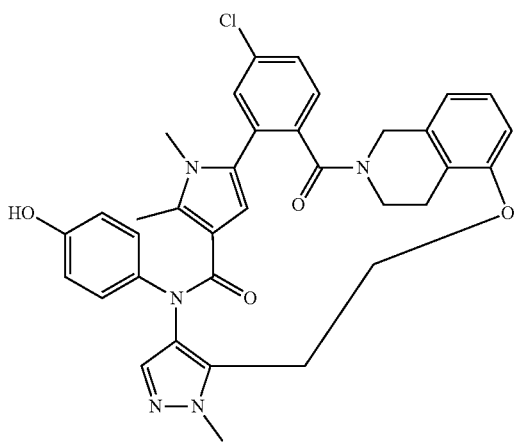 [SMILES: Cc1c2cc(n1C)-c1cc(Cl)ccc1C(=O)N1CCc3c(cccc3OCCc3c(cnn3C)N(c3ccc(O)cc3)C2=O)C1]

The title compound is obtained in accordance with the process of 15 using the acid of Preparation 1 b and the amine of Preparation 3b".

Elemental microanalysis: (% theoretical: measured)
% C=67.57: 67.70; % H=5.18: 4.89; % N=11.26: 11.16.
High-resolution mass spectroscopy (ESI+):
Empirical formula: $C_{35}H_{32}ClN_5O_4$
[M+H]+ calculated 622.2209,
[M+H]+ measured 622.2216.

Example 17: 11-Chloro-4-(4-hydroxyphenyl)-1,7,8-trimethyl-16-(morpholin-4-ylmethyl)-4,16,17,23,24,25-hexahydro-1H,14H-15,18-methano-6,9-(metheno)dibenzo-[b,h]pyrazolo[4,3-p][1,6,11,15]oxatriazacycloicosine-5,14(8H)-dione

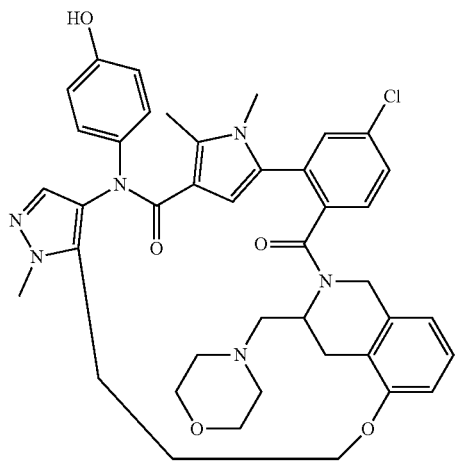 [SMILES: Cc1c2cc(n1C)-c1cc(Cl)ccc1C(=O)N1Cc3cccc(c3CC1CN1CCOCC1)OCCCc1c(cnn1C)N(c1ccc(O)cc1)C2=O]

Step A: tert-Butyl 2-{4-[(4-{[tert-butyl(dimethyl)silyl]oxy}phenyl){1-methyl-5-[3-(tetrahydro-2H-pyran-2-yloxy)propyl]-1H-pyrazol-4-yl}carbamoyl]-1,5-dimethyl-1H-pyrrol-2-yl}-4-chlorobenzoate The title compound is obtained in accordance with the process described in Step B of Example 14 using the acid of Preparation 1b and the amine or Preparation 4b".

¹H NMR (400 MHz, dmso-d6, 300 K) δ ppm: 7.75 (d, 1H), 7.52 (dd, 1H), 7.21 (s, 1H), 7.1 (d, 1H), 7.02 (d, 2H), 6.71 (d, 2H), 6.19 (s, 1H), 4.5 (t, 1H), 3.71 (s, 3H), 3.7-3.2 (4m, 4H), 3.15 (s, 3H), 2.55 (m, 2H), 2.41 (s, 3H), (m, 8H), 1.3 (s, 9H), 0.85 (s, 9H), 0.1 (s, 6 II).
IR: ν: >C=O: 1706 cm⁻¹; >C=O: 1640 cm⁻¹.

Step B: tert-Butyl 2-(4-{(4-{[tert-butyl(dimethyl)silyl]oxy}phenyl)[5-(3-hydroxypropyl)-1-methyl-1H-pyrazol-4-yl]carbamoyl}-1,5-dimethyl-1H-pyrrol-2-yl)-4-chlorobenzoate Pyridinium para-toluenesulphonate (1.5 g; 0.42 mmol) is added to a solution of the compound obtained in Step A (3.28 g; 4.21 mmol) in methanol (30 mL), and then the whole is stirred for 4 hours at 80° C. After returning to ambient temperature, the reaction mixture is diluted with dichloromethane and saturated aqueous ammonium chloride solution. After decantation, the organic phase is washed with water and then dried over magnesium sulphate, filtered and concentrated to dryness. The residue is purified by chromatography over silica gel using dichloromethane and methanol as eluants to obtain the title product.

¹H NMR (400 MHz, dmso-d6, 300 K) δ ppm: 7.75 (d, 1H), 7.59 (dd, 1H), 7.22 (s, 1H), 7.12 (d, 1H), 7.05 (d, 2H), 6.75 (d, 2H), 5.15 (s, 1H), 4.5 (m, 1H), 3.71 (s, 3H), 3.3 (t, 2H), 3.2 (s, 3H), 2.5 (t, 2H), 2.45 (s, 3H), 1.5 (m, 2H), 1.31 (s, 9H), 0.9 (s, 9H), 0.1 (s, 6H).
IR: ν: —OH: 3421 cm⁻¹; >C=O: 1708 cm⁻¹; >C=O: 1634 cm⁻¹.

Step C: tert-Butyl 5-(3-{4-[({5-[2-(tert-butoxycarbonyl]-5-chlorophenyl]-1,2-dimethyl-1H-pyrrol-3-yl}carbonyl)(4-{[tert-butyl(dimethyl)silyl]oxy}phenyl)amino]-1-methyl-1H-pyrazol-5-yl}propoxy)-3-(morpholin-4-ylmethyl)-3,4-dihydroisoquinoline-2(1H)-carboxylate A solution of diisopropyl azodicarboxylate (1 mL; 3.5 mmol) in tetrahydrofuran (20 mL) is added dropwise to a solution of the compound obtained in Step B (1.67 g; 2.9 mmol), triphenylphosphine (1.26 g; 3.5 mmol) and the compound of Preparation 4' (0.84 g; 2.9 mmol) in tetrahydrofuran (20 mL). The reaction mixture is stirred at ambient temperature for 2 hours and then diluted in a mixture of ethyl acetate and water. After extraction of the aqueous phase with ethyl acetate, the organic phases are combined, washed with saturated aqueous ammonium chloride solution, saturated aqueous sodium chloride solution, and then dried over magnesium sulphate, filtered and concentrated to dryness. The residue is purified by chromatography over RP-18 phase using acetonitrile and water as eluants to obtain the title product.

$^1$H NMR (400 MHz, dmso-d6, 300 K) δ ppm: 7.74 (d, 1H), 7.54 (d, 1H), 7.26 (s, 1H), 7.26 (s, 1H), 7.1 (t, 1H), 7.03 (d, 2H), 6.74 (d, 1H), 6.73 (d, 1H), 6.69 (d, 2H), 5.15 (s, 1H), 4.64/4.08 (d+m, 1+1 H), 4.59/4.46 (m+m, 1H), 3.9 (m, 2H), 3.74 (s, 3H), 3.49 (m, 4H), 3.16 (s, 3H), 2.73/2.58 (m+m, 1+1H), 2.69 (m, 2H), 2.5-2.2 (m, 4H), 2.42 (s, 3H), 2.24/1.98 (m+m, 1+1H), 1.79 (m, 2H), 1.42 (s, 9H), 1.25 (s, 9H), 0.85 (s, 9H), 0.07 (s, 6H).

IR: ν: >C=O: 1693 cm$^{-1}$; >C=O: 1641 cm$^{-1}$.

Step D: 11-Chloro-4-(4-hydroxyphenyl)-1,7,8-trimethyl-16-(morpholin-4-ylmethyl)-4,16,17,23,24,25-hexahydro-1H,14H-15,18-methano-6,9-(metheno)dibenzo[b,h]-pyrazolo[4,3-p][1,6,11,15]oxatriazacycloicosine-5,14(8H)-dione To a solution of the compound obtained in Step C (0.315 g; 0.31 mmol) in dichloroethane (12.5 mL) there are added triethylamine (0.13 mL; 0.92 mmol) and zinc bromide (0.34 g; 1.53 mmol). The reaction mixture is stirred at 120° C. for 2 hours under microwaves (150 W) 3 times and is then poured into a mixture of dichloromethane and ice-water. After extraction with dichloromethane, the organic phases are combined, dried over magnesium sulphate, filtered and concentrated.

To a solution of the residue so obtained in dichloromethane (15 mL) there are added in succession 1-hydroxybenzotriazole (0.052 g; 0.23 mmol), 1-(3-dimethylaminopropyl)-3-ethylcarbodiimide hydrochloride (0.072 g; 0.23 mmol) and diisopropylethylamine (0.2 mL; 0.6 mmol). The whole is then stirred for 16 hours at ambient temperature. The reaction mixture is diluted with a mixture of dichloromethane and water. After decantation, the organic phase is dried over magnesium sulphate, filtered and concentrated to dryness.

To a solution of the residue so obtained in tetrahydrofuran (14 mL) there is added 1 M tetrabutylammonium fluoride solution in tetrahydrofuran (0.5 mL; 0.5 mmol). The whole is then stirred for 30 minutes at ambient temperature. After concentration, the residue is taken up in a mixture of ethyl acetate and saturated aqueous sodium chloride solution. After decantation, the organic phase is dried over magnesium sulphate, filtered and concentrated to dryness. The residue is purified by chromatography over silica gel using dichloromethane and ammonia in methanol as eluants. The solid so obtained is dissolved in a mixture of water and acetonitrile and then lyophilised to obtain the title product.

High-resolution mass spectroscopy (ESI+):
Empirical formula: $C_{41}H_{43}ClN_6O_5$
[M+H]+ calculated 735.3056,
[M+H]+ measured 735.3061.

Example 18: 11-Chloro-4-(4-hydroxyphenyl)-1,7,8-trimethyl-5,14-dioxo-4,5,8,16,17,23,24,25-octahydro-1H,14H-15,18-methano-6,9-(metheno)dibenzo[b,h]-pyrrolo[3,2-p][1,6,11,15]oxatriazacycloicosine-2-carbonitrile

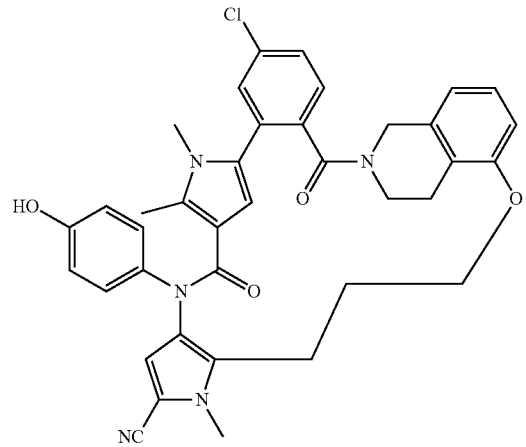 [SMILES: Cc1c2cc(n1C)-c1cc(Cl)ccc1C(=O)N1CCc3c(cccc3OCCCc3c(cc(C#N)n3C)N(c3ccc(O)cc3)C2=O)C1]

The title compound is obtained in accordance with the process of Example 15 using the acid of Preparation 1 b and the amine of Preparation 5b".

Elemental microanalysis: (% theoretical: measured)
% C=69.14: 68.70; % H=5.19: 5.16; % N=10.61: 9.97.
High-resolution mass spectroscopy (ESI+):
Empirical formula: $C_{38}H_{34}ClN_5O_4$
[M+H]+ calculated 660.2372,
[M+H]+ measured 660.2374.

Example 19: 11-Chloro-4-(4-hydroxyphenyl)-1,7,8-trimethyl-5,14-dioxo-1,4,5,8,16,17,23,24-octahydro-14H-15,18-methano-6,9-(metheno)dibenzo[l,r]pyrrolo-[2,3-d][1,6,10,15]oxatriazacyclononadecine-2-carbonitrile

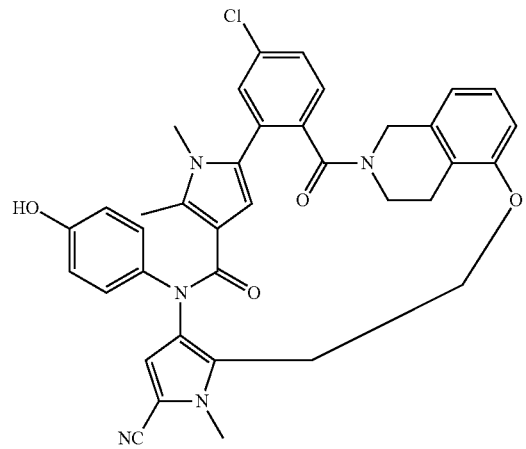 [SMILES: Cc1c2cc(n1C)-c1cc(Cl)ccc1C(=O)N1CCc3c(cccc3OCCc3c(cc(C#N)n3C)N(c3ccc(O)cc3)C2=O)C1]

The title compound is obtained in accordance with the process of Example 15 using the acid of Preparation 1b and the amine of Preparation 6b".
Elemental microanalysis: (% theoretical: measured)
% C=68.78: 68.64; % H=4.99: 5.01; % N=10.84: 10.66.
High-resolution mass spectroscopy (ESI+):
Empirical formula: $C_{37}H_{32}ClN_5O_4$
[M+H]+ calculated (46.2217,
[M+H]+ measured 646.2216.

Example 20: 11-Fluoro-4-(4-hydroxyphenyl)-1,8-trimethyl-1,4,16,17,23,24-hexahydro-14H-15,18-methano-6,9-(metheno)dibenzo[l,r]pyrazolo[3,4-d][1,6,10,15]oxatriazacyclo-nonadecine-5,14(8H)-dione

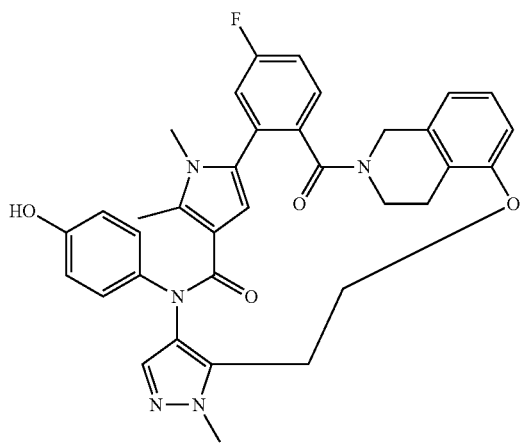 [SMILES: Cc1c2cc(n1C)-c1cc(F)ccc1C(=O)N1CCc3c(cccc3OCCc3c(cnn3C)N(c3ccc(O)cc3)C2=O)C1]

The title compound is obtained in accordance with the process or Example 15 using the acid of Preparation 2b and the amine of Preparation 3b".
High-resolution mass spectroscopy (ESI+):
Empirical formula: $C_{35}H_{33}FN_1O_4$
[M+H]+ calculated 606.2511,
[M+H]+ measured 606.2517.

Example 21: 11-Chloro-4-(4-hydroxyphenyl)-1,7,8-trimethyl-1,4,16,17,23,24-hexahydro-14H-15,18-methano-6,9-(metheno)dibenzo[m,s]pyrazolo[3,4-e][1,4,7,11,16]dioxa-triazacycloeicosin-5,14(8H)-dione

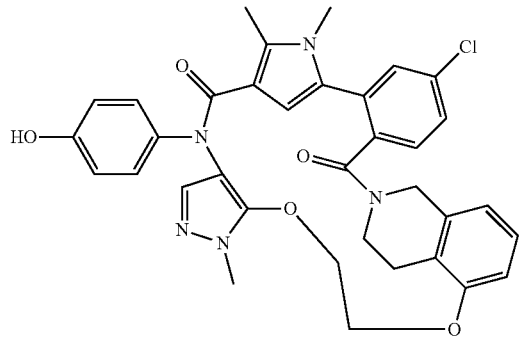 [SMILES: Cc1c2cc(n1C)-c1cc(Cl)ccc1C(=O)N1CCc3c(cccc3OCCOc3c(cnn3C)N(c3ccc(O)cc3)C2=O)C1]

The title compound is obtained in accordance with the process of Example 15 using the acid of Preparation 1b and the amine of Preparation 7b".
Elemental microanalysis: (% theoretical: measured)
% C=65.88: 65.61; % H=5.05: 4.98; % N=10.60: 10.94.
High-resolution mass spectroscopy (ESI+):
Empirical formula: $C_{35}H_{32}ClN_5O_5$
[M+H]+ calculated 638.2165,
[M+H]+ measured 638.2166.

Example 22: 11-Chloro-4-(4-hydroxyphenyl)-1,7,8-trimethyl-1,4,16,21,22,23-hexahydro-14H-15,21-methano-6,9-(metheno)dibenzo[j,o]pyrazolo[3,4-b][1,4,8,13]oxatriaza-cyclononadecine-5,14(8H)-dione

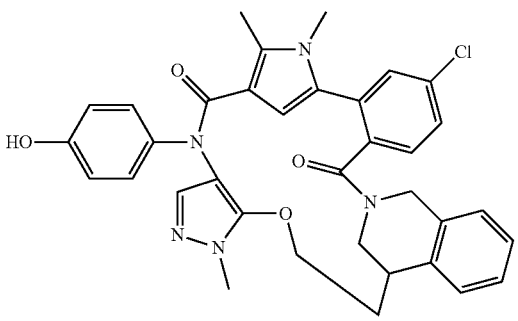 [SMILES: Cc1c2cc(n1C)-c1cc(Cl)ccc1C(=O)N1Cc3ccccc3C(CCOc3c(cnn3C)N(c3ccc(O)cc3)C2=O)C1]

The title compound is obtained in accordance with the process of Example 15 using the acid of Preparation 1b and the amine of Preparation 8b".
High-resolution mass spectroscopy (ESI+):
Empirical formula: $C_{35}H_{32}ClN_5O_4$
[M+H]+ calculated 622.2216,
[M+H]+ measured 622.2208.

Example 23: 11-Chloro-4-(4-hydroxyphenyl)-7,8-dimethyl-1-(tetrahydrofuran-3-yl)-1,4,16,17,23,24-hexahydro-14H-15,18-methano-6,9-(metheno)dibenzo[l,r]pyrazolo[3,4-d][1,6,10,15]oxatriazacyclononadecine-5,14(8H)-dione

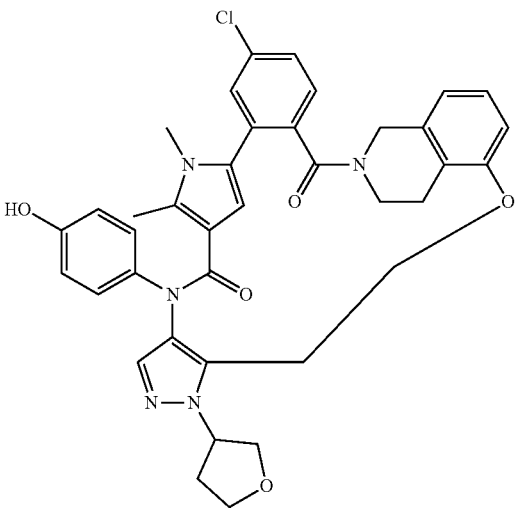 [SMILES: Cc1c2cc(n1C)-c1cc(Cl)ccc1C(=O)N1CCc3c(cccc3OCCc3c(cnn3C3CCOC3)N(c3ccc(O)cc3)C2=O)C1]

The title compound is obtained in accordance with the process of Example 15 using the acid of Preparation 1b and the amine of Preparation 9b".
Elemental microanalysis: (% theoretical: measured)
% C=67.30: 67.12: % H=5.35: 5.08: % N=10.33: 10.31.
High-resolution mass spectroscopy (ESI+):
Empirical formula: $C_{38}H_{36}ClN_5O_5$
[M+H]+ calculated 678.2478.
[M+H]+ measured 678.2481.

Example 24: 11-Chloro-4-(4-hydroxyphenyl)-1,7,8-trimethyl-1,4,22,23-tetrahydro-14H,16H-15,17-methano-6,9-(metheno)dibenzo[b,g]pyrazolo[4,3-o][1,5,10,14]oxatriaza-cyclooctadecine-5,14(8H)-dione

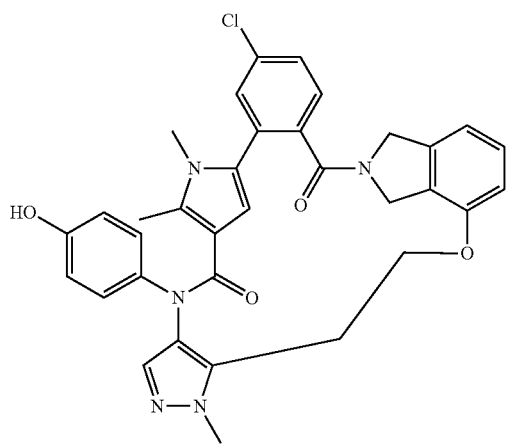 [SMILES: Cc1c2cc(n1C)-c1cc(Cl)ccc1C(=O)N1Cc3cccc(c3C1)OCCc1c(cnn1C)N(c1ccc(O)cc1)C2=O]

The title compound is obtained in accordance with the process of Example 15 using the acid of Preparation 1b and the amine of Preparation 10b".
Elemental microanalysis: (% theoretical: measured)
% C=67.16: 67.31; % H=4.97: 4.91% N=11.52: 11.30.
High-resolution mass spectroscopy (ESI+):
Empirical formula: $C_{34}H_{30}ClN_5O_4$
[M+H]+ calculated 608.2059,
[M+H]+ measured 608.2074.

Example 25: (16R or S)-11-Chloro-4-(4-hydroxyphenyl)-1,7,8,16-tetramethyl-5,14-dioxo-4,5,8,16,17,23,24,25-octahydro-1H,14H-15,18-methano-6,9-(metheno)dibenzo[b,h]-pyrrolo[3,2-p][1,6,11,15]oxatriazacycloicosine-2-carbonitrile enantiomer 1

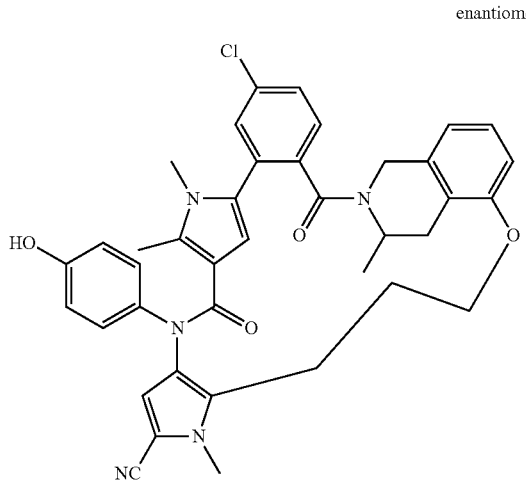

The title compound is obtained in accordance with the process of Example 15 using the acid of Preparation 1b and the amine of Preparation 11b".
Elemental microanalysis: (% theoretical: measured)
% C=69.48: 69.13% H=5.38: 5.37% N=10.39: 10.05.
High-resolution mass spectroscopy (ESI+):
Empirical formula: $C_{39}H_{36}ClN_5O_4$
[M+H]+ calculated 674.2529,
[M+H]+ measured 674.253.

Example 26: (16S or R)-11-Chloro-4-(4-hydroxyphenyl)-1,7,8,16-tetramethyl-5,14-dioxo-4,5,8,16,17,23,24,25-octahydro-1H,14H-15,18-methano-6,9-(metheno)-dibenzo[b,h]pyrrolo[3,2-p][1,6,11,15]oxatriazacycloicosine-2-carbonitrile enantiomer 2

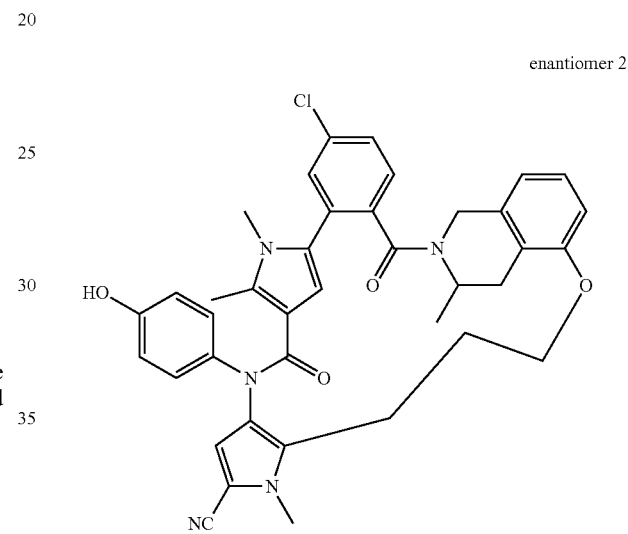

The title compound is obtained in accordance with the process of Example 15 using the acid of Preparation 1 b and the amine of Preparation 12b".
Elemental microanalysis: (% theoretical: measured)
% C=69.48: 68.73; % H=5.38: 5.47; % N=10.39: 10.13.
High-resolution mass spectroscopy (ESI+):
Empirical formula: $C_{39}H_{36}ClN_5O_4$
[M+H]+ calculated 674.2529,
[M+H]+ measured 674.2532.

Example 27: 4-[15-Chloro-3-hydroxy-18,19-dimethyl-12,21-dioxo-7,8,9,10,18,21-hexahydro-6H,12H,22H-8,11-ethano-20,17-(metheno)dibenzo[b,j][1,4,8,13]oxatriaza-cyclooctadecin-22-yl]-1,5-dimethyl-1H-pyrrole-2-carbonitrile

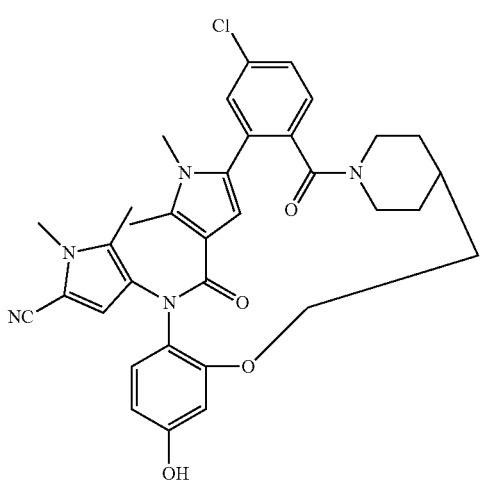 [SMILES: Cc1c(N2C(=O)c3cc(n(C)c3C)-c3cc(Cl)ccc3C(=O)N3CCC(CCOc4cc(O)ccc42)CC3)cc(C#N)n1C]

Step A: tert-Butyl 4-(2-{5-(benzyloxy)-2-[({5-[2-tert-butoxycarbonyl)-5-chlorophenyl]-1,2-dimethyl-1H-pyrrol-3-yl}carbonyl)(5-cyano-1,2-dimethyl-1H-pyrrol-3-yl)amino]-phenoxy}ethyl)piperidine-1-carboxylate The title compound is obtained in accordance with the process described in Step B of Example 14 using the acid of Preparation 1b and the amine of Preparation 13b".

$^1$H NMR (500 MHz, dmso-d6, 300 K) δ ppm: 7.8 (d, 1H), 7.55 (dd, 1H), 7.45-7.25 (m, 5H), 7.05 (d, 1H), 7_05 (s, 1H), 6.65 (br. s, 1H), 6.65 (s, 1H), 6.5 (d, 1H), 5.35 (hr. s, 1H), 5.05 (s, 2H), 3.95 (br. s, 2H), 3.85/2.55 (2br. s, 4H), 3.55 (s, 3H), 3.15 (s, 3H), 2.35 (s, 3H), 2.1 (br. s, 3H), 1.6/0.95 (m+m, 2+2 H), 1.55 (m, 1H), 1.55 (m., 2H), 1.35 (s, 9H), 1.25 (s, 9H).

IR: ν: —CN: 2209 cm$^{-1}$; >C=O: 1715, 1688 and 1640 cm$^{-1}$.

Step B: 4-[15-Chloro-3-hydroxy-18,19-dimethyl-12,21-dioxo-7,8,9,10,18,21-hexahydro-6H,12H,22H-8,11-ethano-20,17-(metheno)dibenzo[b,j][1,4,8,13]oxatriazacycloocta-decin-22-yl]-1,5-dimethyl-1H-pyrrole-2-carbonitrile Zinc bromide (1.45 g; 6.44 mmol) is added to a solution of the compound obtained in Step A (1.3 g; 1.29 mmol) in dichloromethane (12 mL). The reaction mixture is stirred at reflux for 17 hours and then poured into water. The reaction mixture is then stirred for 2 hours and extracted with dichloromethane. The organic phases are combined, dried over magnesium sulphate, filtered and concentrated. The residue is purified by chromatography over silica gel using dichloromethane and methanol as eluants.

To a solution of the residue obtained in dichloromethane (470 mL) there are added in succession 1-hydroxybenzotriazole (0.252 g; 1.86 mmol), 1-(3-dimethylaminopropyl)-3-ethylcarbodiimide hydrochloride (0.320 g; 1.86 mmol) and diisopropylethylamine (1.28 mL; 7.77 mmol). The whole is then stirred for 20 hours at ambient temperature. The reaction mixture is diluted with a mixture of dichloromethane and water. After decantation, the organic phase is dried over magnesium sulphate, filtered and concentrated to dryness. The residue is purified by chromatography over silica gel using dichloromethane and methanol as eluants.

To a solution of the residue so obtained in a mixture of methanol (25 mL) and ethyl acetate (25 mL) there is added palladium on carbon (15% by mass), and then the whole is hydrogenated for 4 hours at ambient temperature under 0.6 bar. The reaction mixture is filtered and concentrated to dryness. The residue is purified by chromatography over silica gel using dichloromethane and methanol as eluants and then by chromatography over RP-18 in supercritical phase using ethanol with 0.1% diethylamine as eluant. The solid so obtained is dissolved in a mixture of water and acetonitrile and then lyophilised to obtain the title product.

Elemental microanalysis: (% theoretical: measured)

% C=66.71: 66.25; % H=5.60: 5.52; % N=11.44: 11.37.

High-resolution mass spectroscopy (ESI+):

Empirical formula: $C_{34}H_{34}ClN_5O_4$

[M+H]+ calculated 612.2367,

[M+H]+ measured 612.2372.

Example 28: 4-[3-Hydroxy-18,19-dimethyl-12,21-dioxo-7,8,9,10,18,21-hexahydro-6H,12H,22H-8,11-ethano-20,17-(metheno)dibenzo[b,j][1,4,8,13]oxatriazacycloocta-decin-22-yl]-1,5-dimethyl-1H-pyrrole-2-carbonitrile

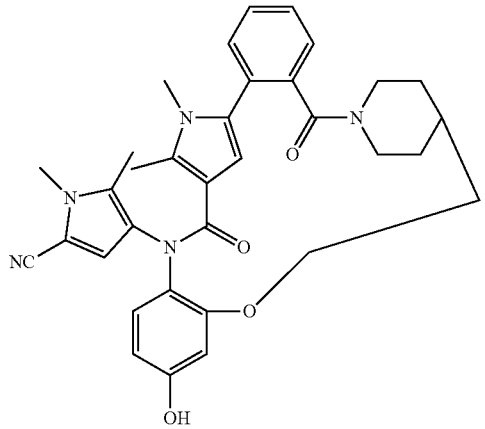 [SMILES: Cc1c(N2C(=O)c3cc(n(C)c3C)-c3ccccc3C(=O)N3CCC(CCOc4cc(O)ccc42)CC3)cc(C#N)n1C]

The title compound is obtained as secondary product in Step B of Example 27

Elemental microanalysis: (% theoretical: measured)

% C=70.69: 70.15; % H=6.11: 6.13; % N=12.12: 12.86.

High-resolution mass spectroscopy (ESI+):

Empirical formula: $C_{34}H_{35}N_5O_4$

[M+H]+ calculated 578.2773.

[M+H]+ measured 578.2762.

Example 29: 4-[16-Chloro-3-hydroxy-19,20-dimethyl-13,22-dioxo-6,7,8,9,10,11,19,22-octahydro-13H,23H-8,12-methano-21,18-(metheno)dibenzo[b,j][1,4,8,13]oxatriazacyclo-nonadecin-23-yl]-1,5-dimethyl-1H-pyrrole-2-carbonitrile

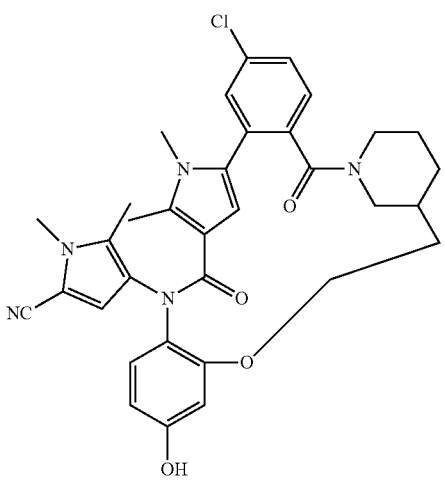 [SMILES: Cc1c(N2C(=O)c3cc(n(C)c3C)-c3cc(Cl)ccc3C(=O)N3CCCC(CCOc4cc(O)ccc42)C3)cc(C#N)n1C]

The title compound is obtained in accordance with the process of Example 27 using the acid of Preparation 1b and the amine of Preparation 14b".

High-resolution mass spectroscopy (ESI+):
Empirical formula: $C_{34}H_{34}ClN_5O_4$
[M+H]+ calculated 612.2372,
[M+H]+ measured 612.2367.

Example 30: 6-Chloro-14-(4-hydroxyphenyl)-10,11-dimethyl-2,13-dioxo-23-oxa-1,10,14-triaza-19-azoniahexacyclo[26.3.1.1~9,12~.1~15,19~.0~3,8~.0~24,29~]tetratriaconta-3,5,7,9(34),11,15(33),16,18,24,26,28-undecaene trifluoromethanesulphonate

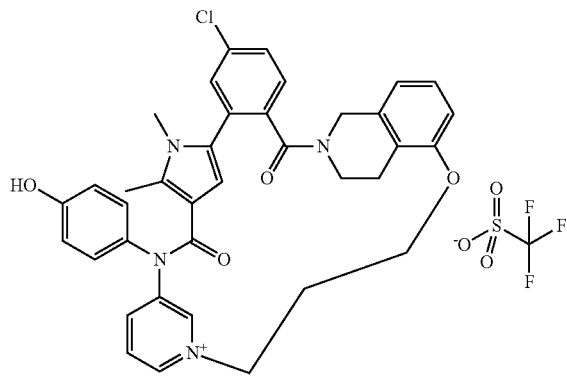

Step A: 3-{({5-[2-(tert-Butoxycarbonyl)-5-chlorophenyl]-1,2-dimethyl-1H-pyrrol-3-yl}carbonyl)[4-(prop-2-en-1-yloxy)phenyl]amino}-1-(3-{[2-(tert-butoxycarbonyl)-1,2,3,4-tetrahydroisoquinolin-5-yl]oxy}propyl)pyridinium 1-Chloro-N,N-2-trimethyl-prop-1-en-1-amine (0.183 mL; 1.49 mmol) is added to a solution of the compound obtained in Preparation 1b (0.47 g; 1.36 mmol) in dichloromethane (34 mL). The reaction mixture is stirred at ambient temperature for 1 hour and then concentrated. The residue is taken up in tetrahydrofuran (14 mL).

In parallel, a solution of sodium hydride (65 mg; 1.63 mmol) in tetrahydrofuran (5 mL) and of compound of Preparation 1.5b" (960 mg; 1.49 mmol) in tetrahydrofuran (15 mL) is prepared, which solution is stirred at ambient temperature for 30 minutes. The residue obtained previously is added thereto and the whole is stirred for 3 hours. The reaction mixture is diluted in a mixture of dichloromethane and water. After extraction of the aqueous phase with dichloromethane, the organic phases are combined, dried over magnesium sulphate, filtered and concentrated to dryness. The residue is purified by chromatography over silica gel using dichloromethane and methanol as eluants to obtain the title product.

$^1$H NMR (400 MHz, dmso-d6, 300 K) δ ppm: 9.14 (br. s, 1H), 8.87 (d, 1H), 8.18 (d, 1H), 8.06 (dd, 1H), 7.81 (d, 1H), 7.58 (d, 1H), 7.17 (d, 2H), 7.13 (t, 1H), 7.01 (s, 1H), 6.95 (d, 2H), 6.77 (d, 1H), 6.77 (d, 1H), 6.01 (m, 1H), 5.34 (d, 1H), 5.21 (d, 1H), 5.2 (s, 1H), 4.8 (t, 2H), 4.57 (d, 2H), 4.45 (br. s, 2H), 4.05 (t, 2H), 3.48 (m, 2H), 3.16 (s, 3H), 2.46 (m, 2H), 2.46 (s, 3H), 2.4 (m, 2H), 1.41/1.3 (2s, 18H).

Step B: 6-Chloro-14-(4-hydroxyphenyl)-10,11-dimethyl-2,13-dioxo-23-oxa-1,10,14-triaza-19-azoniahexacyclo[26.3.1.1~9,12~.1~15,19~.0~3,8~.0~24,29~]tetratriaconta-3,5,7,9(34),11,15(33),16,18,24,26,28-undecaene trifluoromethanesulphonate The title compound is obtained in accordance with the process described in Step C of Example 14 using the compound obtained in the preceding step.

Elemental microanalysis: (% theoretical: measured)
% C=58.27: 58.74; % H=4.38: 4.35; % N=7.15: 7.71.
High-resolution mass spectroscopy (ESI+):
Empirical formula: $C_{38}H_{34}ClF_3N_4O_7S$
[M-CF3SO3]+ calculated 633.2249,
[M-CF3SO3]+ measured 633.2263.

Example 31: 6-Chloro-14-(4-hydroxyphenyl)-10,11,18-trimethyl-22-oxa-1,10,14,17,19-pentaazahexacyclo[25.3.1.1~9,12~.1~15,19~.0~3,8~.0~23,28~]tritriaconta-3,5,7,9(33),11,15,17,23,25,27-decaene-2,13,32-trione

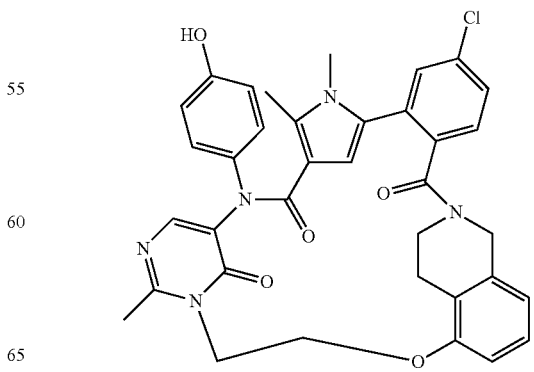

Step A: tert-Butyl 4-chloro-2-[1,5-dimethyl-4-({2-methyl-4-[2-(tetrahydro-2H-pyran-2-yloxy)ethoxy]pyrimidin-5-yl}[4-(prop-2-en-1 yloxy)phenyl]carbamoyl)-1H-pyrrol-2-yl]-benzoate The title compound is obtained in accordance with the process described in Step A of Example 30 using the compound of Preparation 1b and that of Preparation 16b".

¹H NMR (500 MHz, dmso-d6, 300 K) δ ppm: 8.36 (s, 1H), 7.79 (d, 1H), 7.56 (dd, 1H), 7.21 (d, 2H), 7.05 (d, 1H), 6.87 (d, 2H), 5.99 (m, 1H), 5.33 (d, 1H), 5.29 (s, 1H), 5.2 (d, 1H), 4.56 (m, 1H), 4.53 (d, 2H), 4.45 (m, 2H), 3.83/3.61 (2m, 2H), 3.69/3.35 (2m, 2H), 3.15 (s, 3H), 2.5 (s, 3H), 2.39 (s, 3H), 1.63/1.37 (2m, 2H), 1.51/1.38 (2m, 2H), 1.42/1.32 (2m, 2H), 1.29 (s, 9H).

IR: ν: >C=O: 1703 cm⁻¹; >C=O: 1644 cm⁻¹.

Step B: tert-Butyl 5-{2-[5-{(({5-[2-(tert-butoxycarbonyl)-5-chlorophenyl]-1,2-dimethyl-1H-pyrrol-3-yl}carbonyl)[4-(prop-2-en-1-yloxy)phenyl]amino}-2-methyl-6-oxopyrimidin-1(6H)-yl]ethoxy}-3,4-dihydroisoquinoline-2(1H)-carboxylate Pyridinium para-toluenesulphonate (0.34 g; 1.35 mmol) is added to a solution of the compound obtained in Step A (0.97 g; 1.35 mmol) in methanol (7 mL), and then the whole is stirred for 4 hours at 80° C. After returning to ambient temperature, the reaction mixture is concentrated and then diluted with ethyl acetate and water. After decantation, the organic phase is washed with water and saturated aqueous sodium chloride solution and then dried over magnesium sulphate, filtered and concentrated to dryness.

To a solution of the residue obtained (0.579 g; 0.915 mmol) in dichloromethane (5 mL) there are added tosyl chloride (0.349 g; 1.83 mmol) and triethylamine (514 μL; 3.66 mmol), and then the whole is stirred for 16 hours at ambient temperature. The reaction mixture is diluted with dichloromethane and water. After decantation, the organic phase is washed with water and saturated aqueous sodium chloride solution and then dried over magnesium sulphate, filtered and concentrated to dryness.

To a solution of the residue obtained (0.7 g; 0.752 mmol) in N,N-dimethylformamide (5 mL) there are added the compound of Preparation 3b' (0.225 g; 0.903 mmol) and potassium carbonate (0.313 g; 2.26 mmol), and then the whole is stirred for 2 hours at 125° C. The reaction mixture is diluted with ethyl acetate and water. After decantation, the organic phase is washed with water and saturated aqueous lithium chloride solution and then dried over magnesium sulphate, filtered and concentrated to dryness. The residue is purified by chromatography over silica gel using dichloromethane and methanol as eluants to obtain the title product.

¹H NMR (500 MHz, dmso-d6, 300 K) δ ppm: 7.88 (s, 1H), 7.72 (d, 1H), 7.5 (dd, 1H), 7.15 (d, 2H), 7.08 (t, 1H), 7.07 (d, 1H), 6.84 (d, 2H), 6.74 (d, 1H), 6.74 (d, 1H), 5.99 (m, 1H), 5.36 (s, 1H), 5.33 (d, 1H), 5.2 (d, 1H), 4.52 (d, 2H), 4.43 (br. s, 2H), 4.39 (t, 2H), 4.2 (t, 2H), 3.48 (t, 2H), 3.11 (s, 3H), 2.62 (s, 3H), 2.47 (t, 2H), 2.36 (s, 3H), 1.41/1.28 (2s, 18H).

IR: ν: >C=O: 1682 cm⁻¹; >C=O: 1639 cm⁻¹.

Step C: 6-Chloro-14-(4-hydroxyphenyl)-10,11,18-trimethyl-22-oxa-1,10,14,17,19-penta-azahexacyclo[25.3.1.1~9,12~.1~15,19~.0~3,8~.0~23,28~]tritriaconta-3,5,7,9(33),11,15,17,23,25,27-decaene-2,13,32-trione The title compound is obtained in accordance with the process described in Step C of Example 14 using the compound of the preceding step.

Elemental microanalysis: (% theoretical: measured)
% C=66.51: 66.29; % H=4.96: 4.95; % N=10.77: 10.38.
High-resolution mass spectroscopy (ESI+):
Empirical formula: C₃₆H₃₂ClN₅O₅
[M+H]+ calculated 650.2169,
[M+H]+ measured 650.2165.

Example 32: 18-Chloro-11-(4-hydroxyphenyl)-2,14,15-trimethyl-1,12-dioxo-1,2,3,4,12,15-hexahydro-11H-6,10:13,16-di(metheno)-5,2,11,15-benzoxatriazacyclo-octadecine-8-carbonitrile

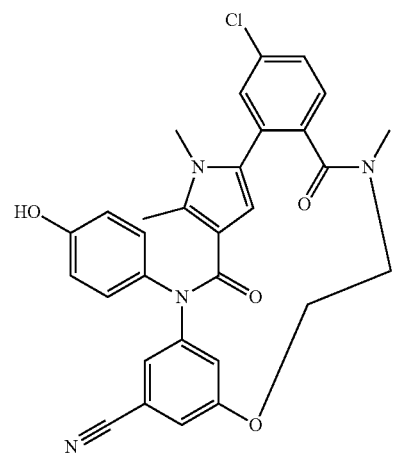 [SMILES: Cc1c2cc(n1C)-c1cc(Cl)ccc1C(=O)N(C)CCOc1cc(C#N)cc(c1)N(c1ccc(O)cc1)C2=O]

Step A: tert-Butyl 2-(4-{(3-{2-[(tert-butylcarbonyl)(methyl)amino]ethoxy}-5-cyanophenyl)[4-(prop-2-en-1-yloxy)phenyl]carbamoyl}-1,5-dimethyl-1H-pyrrol-2-yl)-4-chlorobenzoate The title compound is obtained in accordance with the process described in Step B of Example 14 using the compound of Preparation 1b and that of Preparation 17b".

¹H NMR (400 MHz, dmso-d6, 300 K) δ ppm: 7.78 (d, 1H), 7.56 (dd, 1H), 7.28 (br. s, 1H), 7.19 (br. s, 1H). 7.14 (d, 2H), 7.07 (d, 1H), 6.99 (unresolved peak, 1H). 6.92 (d, 2H), 6 (m, 1H), 5.34/5.21 (2dquad, 2H), 5.26 (s, 1H), 4.55 (m, 2H), 4.11 (m, 2H), 3.48 (t, 2H), 3.16 (s, 3H), 2.8 (s, 3H), 2.43 (s, 3H), 1.3 (m, 18H).

IR: ν: >CN: 2230 cm⁻¹; >C=O: 1697 and 1645 cm⁻¹.

Step B: 18-Chloro-11-(4-hydroxyphenyl)-2,14,15-trimethyl-1,12-dioxo-1,2,3,4,12,15-hexahydro-11H-6,10:13,16-di(metheno)-5,2,11,15-benzoxatriazacyclooctadecine-8-carbonitrile The title compound is obtained in accordance with the process described in Step C of Example 14 using the compound of the preceding step.

Elemental microanalysis: (% theoretical: measured)
% C=66.60: 65.92; % H=4.66: 4.62; % N=10.36: 10.08.
High-resolution mass spectroscopy (ESI+):
Empirical formula: C₃₀H₂₅ClN₄O₄
[M+H]+ calculated 541.1642,
[M+H]+ measured 541.1637.

Example 33: 21-Chloro-6-(4-hydroxyphenyl)-2,3,17-trimethyl-5,18-dioxo-5,6,13,14,15,16,17,18-octahydro-2H-4,1:11,7-di(metheno)-12,2,6,17-benzoxatriazacyclo-icosine-9-carbonitrile

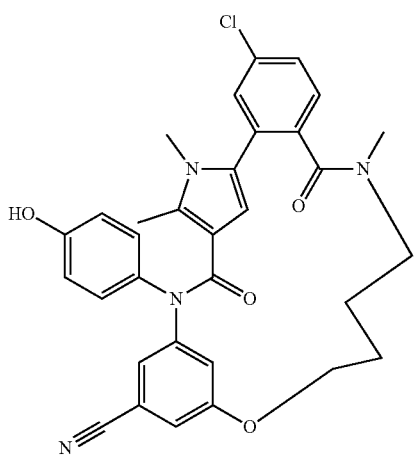 [SMILES: Cc1c2cc(n1C)-c1cc(Cl)ccc1C(=O)N(C)CCCCOc1cc(C#N)cc(c1)N(c1ccc(O)cc1)C2=O]

The title compound is obtained in accordance with the process of Example 32 using the acid of Preparation 1b and the amine of Preparation 18b".

Elemental microanalysis: (% theoretical: measured)
% C=67.54: 67.16; % H=5.14: 5.05; % N=9.85: 9.27
High-resolution mass spectroscopy (ESI+):
Empirical formula: $C_{32}H_{29}ClN_4O_4$.
[M+H]+ calculated 569.1955,
[M+H]+ measured 569.1950.

Example 34: 18-chloro-11-(4-hydroxyphenyl)-14,15-dimethyl-6,7,10,11,23,24-hexahydro-9H,21H-1,22-methano-13,16-(metheno)dibenzo[m,s][1,4,7,11,16]dioxatriaza-cycloicosine-12,21(15H)-dione

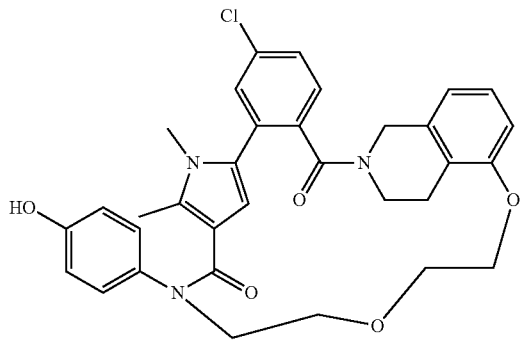 [SMILES: Cc1c2cc(n1C)-c1cc(Cl)ccc1C(=O)N1CCc3c(cccc3OCCOCCN(c3ccc(O)cc3)C2=O)C1]

Step A: tert-Butyl 5-(2-{2-[({5-[2-(tert-butoxycarbonyl)-5-chlorophenyl]-1,2-dimethyl-1H-pyrrol-3-yl}carbonyl)(4-{[tert-butyl(dimethyl)silyl]oxy}phenyl)amino]ethoxy}ethoxy)-3,4-dihydroisoquinoline-2(1H)-carboxylate The title compound is obtained in accordance with the process described in Step B of Example 14 using the acid of Preparation 1b and the amine of Preparation 19b".

$^1$H NMR (500 MHz, dmso-d6, 300 K) δ ppm: 7.7 (d, 1H), 7.5 (dd, 1H), 7.11 (d, 1H), 7.05 (m, 2H), 6.8 (t, 1H), 6.7 (d, 2H), 6.65 (m, 2H), 4.85 (s, 1H), 4.42 (s, 2H), 4.05 (m, 2H), 3.87 (m, 2H), 3.7 (m, 2H), 3.65 (m, 2H), 3.45 (m, 2H), 3.15 (s, 3H), 2.6 (m, 2H), 2.4 (s, 3H), 1.4-0.8 (s, 27H), 0.1 (s, 6H).

Step B: 18-Chloro-11-(4-hydroxyphenyl)-14,15-dimethyl-6,7,10,11,23,24-hexahydro-9H,21H-1,22-methano-13,16-(metheno)dibenzo[m,s][1,4,7,11,16]dioxatriazacyclo-icosine-12,21(15H)-dione The title compound is obtained in accordance with the process described in Step D of Example 17 using the compound of the preceding step.

High-resolution mass spectroscopy (ESI+):
Empirical formula: $C_{33}H_{32}ClN_3O_5$
[M+H]+ calculated 586.2103,
[M+H]+ measured 586.2124.

Example 35: 21-Chloro-29-(4-hydroxyphenyl)-25,26-dimethyl-17,28-dioxo-2,3,4,16,25,29-hexaazaheptacyclo[28.3.1.1~2,5~.1~12,16~.1~24,27~.0~8,13~.0~18,23~]-heptatriaconta-1(34),3,5(37),8,10,12,18,20,22,24(35),26,30,32-tridecaene-32-carbonitrile

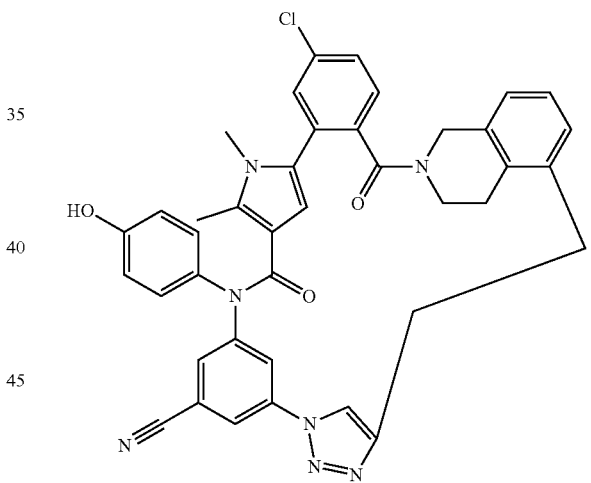

The title compound is obtained in accordance with the process of Example 34 using the acid of Preparation 1b and the amine of Preparation 20b".

High-resolution mass spectroscopy (ESI+):
Empirical formula: $C_{40}H_{32}ClN_7O_3$
[M+H]+ calculated 694.2328,
[M+H]+ measured 694.233.

Example 36: 10-Chloro-2-(4-hydroxyphenyl)-5,6-dimethyl-23,26,29-trioxa-2,6,15,31,34-pentaaza-hexacyclo[28.2.2.1~4,7~.1~15,18~.0~8,13~.0~17,22~]hexatriaconta-1(32),4,7(36),8,10,12,17,19,21,30,33-undecaene-3,14-dione

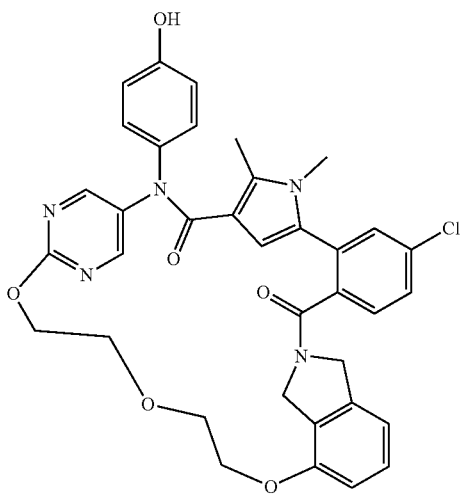 [SMILES: Cc1c2cc(n1C)-c1cc(Cl)ccc1C(=O)N1Cc3cccc(c3C1)OCCOCCOc1ncc(cn1)N(c1ccc(O)cc1)C2=O]

Step A: tert-Butyl 4-(2-{2-[(5-{({5-[2-(tert-butoxycarbonyl)-5-chlorophenyl]-1,2-dimethyl-1H-pyrrol-3-yl}carbonyl)[4-(prop-2-en-1-yloxy)phenyl]amino}pyrimidin-2-yl)oxy]ethoxy}ethoxy)-1,3-dihydro-2H-isoindole-2-carboxylate The title compound is obtained in accordance with the process described in Step B of Example 14 using the acid of Preparation 1b and the amine of Preparation 21b".

$^1$H NMR (500 MHz, dmso-d6, 300 K) δ ppm: 8.46/8.45 (s, 2H), 7.77 (d, 1H), 7.54 (dd, 1H), 7.26-6.83 (m, 3H), 7.21 (m, 2H), 7.08 (d, 1H), 6.92 (m, 2H), 5.99 (m, 1H), 5.33/5.2 (m+m, 2H), 5.23/5.22 (s, 1H), 4.6-4.41 (m, 4H), 4.54 (m, 2H), 4.45-3.75 (m, 8H), 3.15 (s, 3H), 2.43 (s, 3H), 1.46-1.25 (s, 18H).

Step B: 4-Chloro-2-(4-{(2-{2-[2-(2,3-dihydro-1H-isoindol-4-yloxy)ethoxy]ethoxy}-pyrimidin-5-yl)[4-(prop-2-en-1-yloxy)phenyl]carbamoyl}-1,5-dimethyl-1H-pyrrol-2-yl)-benzoic acid To a solution of the compound obtained in Step A (1.2 g; 1.36 mmol) in dioxane (18 mL) there are added triethylamine (1.9 mL; 13.6 mmol) and trimethylsilyl trifluoromethanesulphonate (2.46 mL; 13.6 mmol). The reaction mixture is stirred at ambient temperature for 20 minutes and then poured into ice-water. The precipitate obtained is filtered off and then purified by chromatography over RP-18 phase using acetonitrile, water and ammonium acetate as eluants to obtain the title product.

$^1$H NMR (500 MHz, dmso-d6, 300 K) δ ppm: 10.98 (brs, 2H), 8.36 (s, 2H), 7.58 (d, 1H), 7.3 (dd, 1H), 7.28 (t, 1H), 7.16 (m, 2H), 6.97 (d, 1H), 6.95 (m, 2H), 6.95 (d, 1H), 6.92 (d, 1H), 6.03 (m, 1H), 5.41 (s, 1H), 5.38/5.25 (m+m, 2H), 4.57 (m, 2H), 4.41 (brs, 2H), 4.4-3.72 (m, 8H), 4.33 (brs, 2H), 3.15 (s, 3H), 2.31 (s, 3H).

Step C: 10-Chloro-2-(4-hydroxyphenyl)-5,6-dimethyl-23,26,29-trioxa-2,6,15,31,34-penta-azahexacyclo[28.2.2.1~4,7~.1~15,18~.0~8,13~. 0~17,22~]hexatriaconta-1(32),4,7(36),8,10,12,17,19,21,30,33-undecaene-3,14-dione 4-(4,6-Dimethoxy-1,3,5-triazin-2-yl)-4-methyl-morpholin-4-ium tetrafluoroborate (237 mg; 0.7 mmol) is added to a solution of the compound obtained in Step B (370 mg; 0.61 mmol) in dichloromethane (50 mL). The reaction mixture is stirred at ambient temperature for 1 hour. After washing with water, the organic phase is dried over magnesium sulphate, filtered and concentrated.

To a solution of the residue so obtained in a mixture of dichloromethane (10 mL) and methanol (5 mL) there is added 1,3-dimethylbarbituric acid (0.159 g; 1 mmol). The reaction mixture is degassed with argon for 10 minutes, and tetrakis-(triphenyl-phosphine)palladium(0) (0.030 g; 0.02 mmol) is added. The mixture is then stirred for 16 hours at ambient temperature. After concentration of the solvents, the residue is purified by chromatography over RP-18 phase using acetonitrile, water and ammonium acetate as eluants to obtain the title product.

High-resolution mass spectroscopy (ESI+):

Empirical formula: $C_{36}H_{32}ClN_5O_6$

[M+H]+ calculated 666.2198,

[M+H]+ measured 666.2108.

Example 37: 10-Fluoro-2-(4-hydroxyphenyl)-5,6-dimethyl-24,27,30-trioxa-2,6,15,32,35-pentaazahexacyclo[29.2.2.1~4,7~.1~15,19~.0~8,13~.0~18,23~]heptatriaconta-1(33),4,7(37),8,10,12,18,20,22,31,34-undecuene-3,14-dione

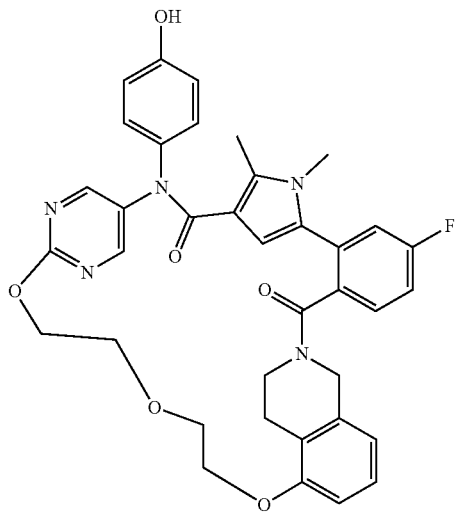 [SMILES: Cc1c2cc(n1C)-c1cc(F)ccc1C(=O)N1CCc3c(cccc3OCCOCCOc3ncc(cn3)N(c3ccc(O)cc3)C2=O)C1]

The title compound is obtained in accordance with the process of Example 36 using the acid of Preparation 2b and the amine of Preparation 22b".

High-resolution mass spectroscopy (ESI+):

Empirical formula: $C_{37}H_{34}FN_5O_6$

[M+H]+ calculated 664.2559,

[M+H]+ measured 664.2571.

Example 38: 10-Chloro-2-(4-hydroxyphenyl)-5,6-dimethyl-24,27,30-trioxa-2,6,15,32,35-pentaazahexacyclo[29.2.2.1~4,7~.1~15,19~.0~8,13~.0~18,23~]heptatriaconta-1(33),4,7(37), 8,10,12,18,20,22,31,34-undecuene-3,14-dione

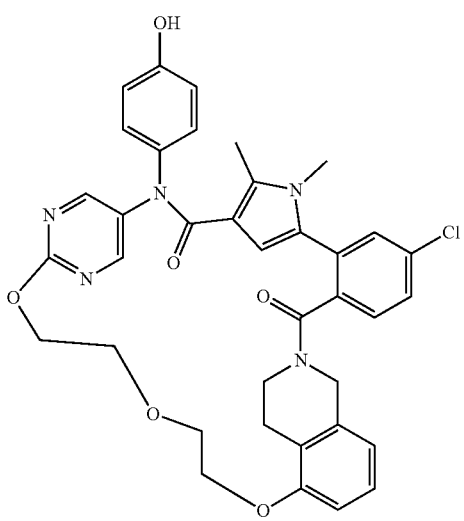 [SMILES: Cc1c2cc(n1C)-c1cc(Cl)ccc1C(=O)N1CCc3c(cccc3OCCOCCOc3ncc(cn3)N(c3ccc(O)cc3)C2=O)C1]

The title compound is obtained in accordance with the process of Example 36 using the acid of Preparation 1b and the amine of Preparation 22b".
High-resolution mass spectroscopy (ESI+):
Empirical formula: $C_{37}H_{34}ClN_5O_6$
[M+H]+ calculated 680.2276,
[M+H]+ measured 680.2280.

Example 39: 10-Chloro-2-(4-hydroxyphenyl)-5,6-dimethyl-24,31-dioxa-2,6,15,33,36-pentaazahexacyclo[30.2.2.1~4,7~.1~15,19~.0~8,13~.0~18,23~]octatriaconta-1(34),4,7(38),8,10,12,18,20,22,32,35-undecuene-3,14-dione

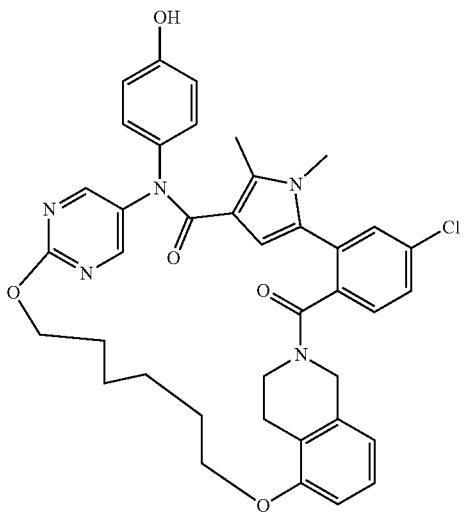 [SMILES: Cc1c2cc(n1C)-c1cc(Cl)ccc1C(=O)N1CCc3c(cccc3OCCCCCCOc3ncc(cn3)N(c3ccc(O)cc3)C2=O)C1]

The title compound is obtained in accordance with the process of Example 38 using the amine of Preparation 23b".

High-resolution mass spectroscopy (ESI+):
Empirical formula: $C_{39}H_{38}ClN_5O_5$
[M+H]+ calculated 692.2640,
[M+H]+ measured 692.2646.

Example 40: 10-Chloro-2-(4-hydroxyphenyl)-5,6-dimethyl-24,30-dioxa-2,6,15,32,35-pentaazahexacyclo[29.2.2.1~4,7~.1~15,19~.0~8,13~.0~8,23~]heptatriaconta-1(33),4,7(37),8,10,12,18,20,22,31,34-undecuene-3,14-dione

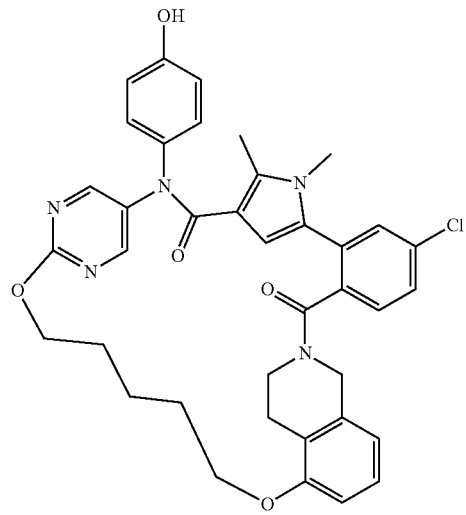 [SMILES: Cc1c2cc(n1C)-c1cc(Cl)ccc1C(=O)N1CCc3c(cccc3OCCCCCOc3ncc(cn3)N(c3ccc(O)cc3)C2=O)C1]

The title compound is obtained in accordance with the process of Example 38 using the amine of Preparation 24b".
High-resolution mass spectroscopy (ESI+):
Empirical formula: $C_{37}H_{36}ClN_5O_5$
[M+H]+ calculated: 678.2484,
[M+H]+ measured: 678.2488.

Example 41: 10-Chloro-2-(4-hydroxyphenyl)-5,6-dimethyl-24,29-dioxa-2,6,15,31,34-pentaazahexacyclo[28.2.2.1~4,7~.1~15,19~.0~8,13~.0~18,23~]hexatriaconta-1(32),4,7(36),8,10,12,18,20,22,30,33-undecaene-3,14-dione

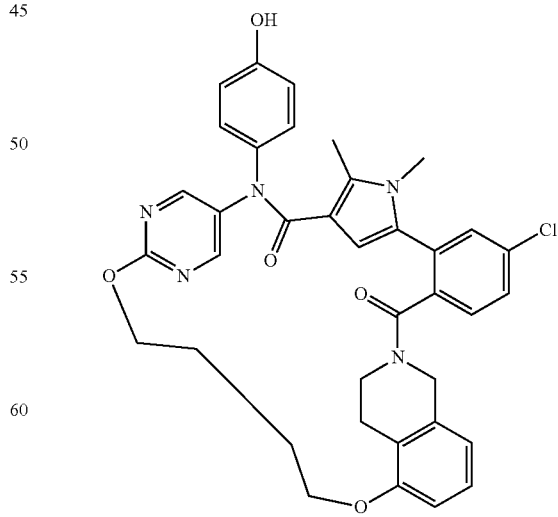

The title compound is obtained in accordance with the process of Example 38 using the amine of Preparation 25b".

High-resolution mass spectroscopy (ESI+):
Empirical formula: $C_{37}H_{34}ClN_5O_5$.
[M+H]+ calculated: 664.2328
[M+H]+ measured: 664.2331

Example 42: 10-Chloro-2-(4-hydroxyphenyl)-5,6-dimethyl-21,24,27-trioxa-2,6,15,29,32-pentaazapentacyclo[26.2.2.1~4,7~.1~15,19~.0~8,13~]tetratriaconta-1(30),4, 7(34),8,10,12,28,31-octaene-3,14-dione

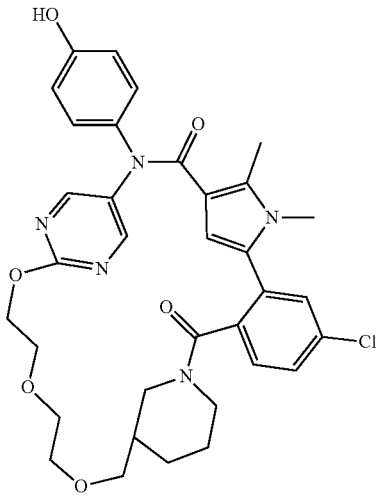 [SMILES: Cc1c2cc(n1C)-c1cc(Cl)ccc1C(=O)N1CCCC(COCCOCCOc3ncc(cn3)N(c3ccc(O)cc3)C2=O)C1]

The title compound is obtained in accordance with the process of Example 38 using the amine of Preparation 26b".
High-resolution mass spectroscopy (ESI+):
Empirical formula: $C_{34}H_{36}ClN_5O_6$
[M+H]+ calculated: 646.2433
[M+H]+ measured: 646.2427.

Example 43: 6-Chloro-14-(4-hydroxyphenyl)-10,11-dimethyl-19,22,25-trioxa-1,10,14,17,32-pentaazapentacyclo[25.2.2.2~15,18~. 1~9,12~.0~3,8~]tetratriaconta-3,5,7,9(34),11,15,17,32-octaene-2,13-dione

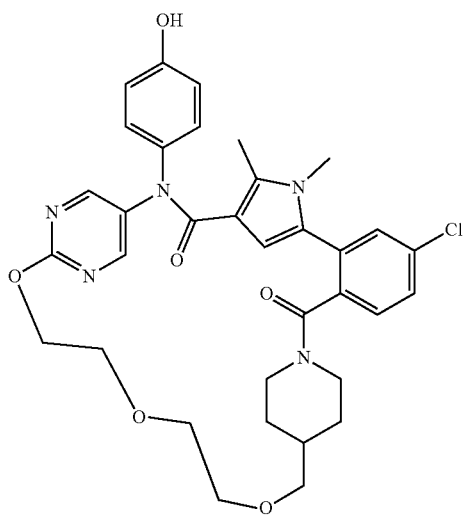 [SMILES: Cc1c2cc(n1C)-c1cc(Cl)ccc1C(=O)N1CCC(CC1)COCCOCCOc1ncc(cn1)N(c1ccc(O)cc1)C2=O]

The title compound is obtained in accordance with the process of Example 38 using the amine of Preparation 27b".
High-resolution mass spectroscopy (ESI+):
Empirical formula: $C_{34}H_{36}ClN_5O_6$
[M+H]+ calculated: 646.2433
[M+H]+ measured: 646.2426.

Example 44: 10-Chloro-2-(4-hydroxyphenyl)-5,6,27-trimethyl-24,30-dioxa-2,6,15,27,32,35-hexaazahexacyclo[29.2.2.1~4,7~.1~15,19~.0~8,13~.0~18, 23~]hepta-triaconta-1(33),4,7(37),8,10,12,18,20,22,31,34-undecaene-3,14-dione

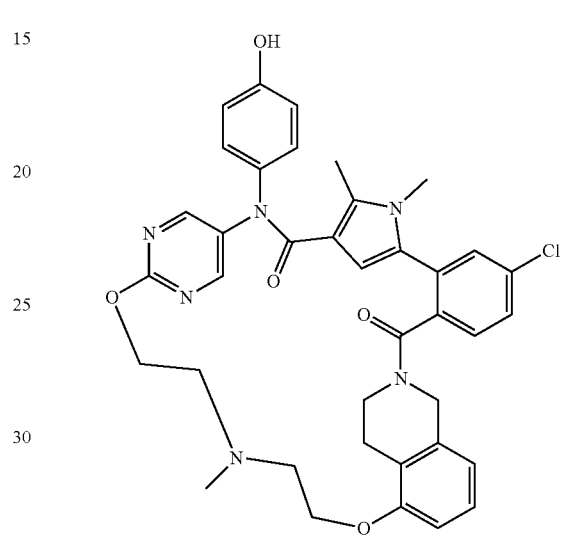

The title compound is obtained in accordance with the process of Example 38 using the amine of Preparation 28b".
High-resolution mass spectroscopy (ESI+):
Empirical formula: $C_{38}H_{37}ClN_5O_5$
[M+H]+ calculated: 693.2593
[M+H]+ measured: 693.2583.

Pharmacological Study

Example A: Inhibition of Bcl-2 by the Fluorescence Polarisation Technique

The fluorescence polarisation tests were carried out on microplates (384 wells). The Bcl-2 protein, labelled (histag-Bcl-2 such that Bcl-2 corresponds to the UniProtKB® primary accession number: P10415), at a final concentration of $5 \times 10^{-9}$M, is mixed with a fluorescent peptide (Fluorescein-REIGAQLRRMADDLNAQY), at a final concentration of $1.00 \times 10^{-9}$M in a buffer solution (Hepes 10 mM, NaCl 150 mM, Tween20 0.05%, pH 7.4), in the presence or absence of increasing concentrations of test compounds. After incubation for 2 hours, the fluorescence polarisation is measured.

The results are expressed in $IC_{50}$ (the concentration of compound that inhibits fluorescence polarisation by 50%) and are presented in Table 1 below.

The results show that the compounds of the invention inhibit interaction between the Bcl-2 protein and the fluorescent peptide described hereinbefore.

Example B: In Vitro Cytotoxicity

The cytotoxicity studies were carried out on the RS4; 11 leukaemia tumour line.

The cells are distributed onto microplates and exposed to the test compounds for 48 hours.

The cell viability is then quantified by a colorimetric assay, the Microculture Tetrazolium Assay (Cancer Res., 1987, 47, 939-942).

The results are expressed in $IC_{50}$ (the concentration of compound that inhibits cell viability by 50%) and are presented in Table 1 below.

The results show that the compounds of the invention are cytotoxic.

TABLE 1

$IC_{50}$ of Bcl-2 inhibition (fluorescence polarisation test) and of cytotoxicity for RS4; 11 cells

|  | $IC_{50}$ (μM) Bcl-2 FP | $IC_{50}$ (M) MTT RS4; 11 |
|---|---|---|
| Example 1 | 0.0067 | 1.07E−07 |
| Example 2 | 0.0044 | 1.79E−07 |
| Example 3 | 0.0655 | 7.49E−07 |
| Example 4 | 0.0023 | 7.73E−09 |
| Example 5 | 0.00205 | 2.14E−08 |
| Example 6 | 0.0052 | 2.66E−08 |
| Example 7 | 0.003 | 4.94E−09 |
| Example 8 | 0.00615 | 4.93E−08 |
| Example 9 | 0.0023 | 5.24E−09 |
| Example 10 | 0.299 | >3E−07 |
| Example 11 | 0.157 | 4.48E−07 |
| Example 12 | not tested | not tested |
| Example 13 | 0.0332 | 2.39E−07 |
| Example 14 | 0.0147 | 1.46E−08 |
| Example 15 | 0.0037 | 1.16E−08 |
| Example 16 | 0.00555 | 5.33E−08 |
| Example 17 | 0.0123 | 6.28E−08 |
| Example 18 | 0.00365 | 8.36E−09 |
| Example 19 | 0.0055 | 1.03E−08 |
| Example 20 | 0.0123 | 8.12E−08 |
| Example 21 | 0.0148 | 1.31E−07 |
| Example 22 | 0.0153 | 1.18E−08 |
| Example 23 | 0.0143 | 7.33E−08 |
| Example 24 | 0.0149 | 1.06E−07 |
| Example 25 | 0.268 | 8.09E−07 |
| Example 26 | 0.0041 | 1.66E−09 |
| Example 27 | 0.0098 | 1.04E−07 |
| Example 28 | 0.0288 | 4.01E−06 |
| Example 29 | not tested | 7.05E−08 |
| Example 30 | 0.0314 | >1.88E−06 |
| Example 31 | 74.55% @1.1 μM | 1.33E−06 |
| Example 34 | 0.0693 | 1.24E−06 |
| Example 36 | 41.5% @10 μM | >6E−07 |
| Example 37 | 0.0102 | 4.96E−08 |
| Example 38 | 0.00385 | 2.31E−08 |
| Example 39 | 0.0768 | 1.49E−07 |
| Example 40 | 0.0064 | 2.99E−08 |
| Example 41 | 0.0467 | 1.97E−07 |
| Example 42 | 39.2% @10 μM | >6E−07 |
| Example 43 | 34.8% @10 μM | >1.88E−06 |
| Example 44 | 0.00497 | 3.54E−08 |

Example C: Quantification of the Cleaved Form of Caspase 3 In Vivo

The ability of the compounds of the invention to activate caspase 3 is evaluated in a xenograft model of RS4; 11 leukaemia cells.

$1 \times 10^7$ RS4; 11 cells are grafted sub-cutaneously into immunosuppressed mice (SCID strain). 25 to 30 days after the graft, the animals are treated orally with the various compounds. After 2 hours' treatment, the tumour masses are recovered and lysed, and the cleaved (activated) form of caspase 3 is quantified in the tumour lysates.

This quantification is carried out using the "Meso Scale Discovery (MSD) ELISA platform" test, which specifically assays the cleaved form of caspase 3. It is expressed in the form of an activation factor corresponding to the ratio between the quantity of cleaved caspase 3 in the treated mice divided by the quantity of cleaved caspase 3 in the control mice.

The results show that the compounds of the invention are capable of inducing apoptosis in RS4; 11 tumour cells in vivo.

TABLE 2

Caspase activation factors (cleaved caspase 3 MSD test in the tumours of treated mice versus control mice) in vivo, after treatment by the oral route (exact doses in brackets)

| Compound tested | Formulation | Dose (mg/kg) | Activation factor ± SEM (versus control) |
|---|---|---|---|
| Example 6 | PEG/EtOH/Water | 12.5 | 6.8 ± 4.2 |
| Example 6 | PEG/EtOH/Water | 25 | 32.3 ± 9.1 |
| Example 16 | PEG/EtOH/Water | 25 | 31.7 ± 2.9 |
| Example 16 | PEG/EtOH/Water | 50 | 75.1 ± 13.2 |
| Example 18 | PEG/EtOH/Phosal | 6.25 | 7.8 ± 2.5 |
| Example 18 | PEG/EtOH/Phosal | 12.5 | 31.7 ± 6.0 |
| Example 29 | PEG/EtOH/Phosal | 25 | 13.3 ± 6.3 |
| Example 29 | PEG/EtOH/Phosal | 50 | 54.4 ± 9.7 |

Example D: Pharmaceutical Composition: Tablets 100 tablets containing a dose of 5 mg of a compound selected from Examples 1 to 44 5 g Wheat starch . . . 20 g Maize starch . . . 20 g Lactose . . . 30 g Magnesium stearate . . . 2 g Silica . . . 1 g Hydroxypropylcellulose . . . 2 g

The invention claimed is:

1. A compound of formula (I):

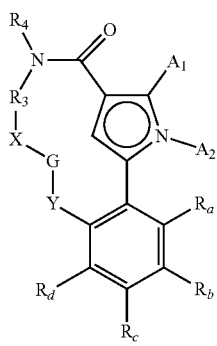

wherein:

A₁ and A₂, independently of one another, represent a hydrogen or halogen atom, a linear or branched polyhalo-$(C_1$-$C_6)$alkyl, a linear or branched $(C_1$-$C_6)$alkyl group or a cycloalkyl group, or A₁ and A₂, together with the atoms to which they are attached, form an aromatic or non-aromatic heterocycle Het composed of 5, 6 or 7 ring members, which optionally has, in addition to nitrogen, from one to 3 hetero atoms selected independently from oxygen, sulphur and nitrogen, wherein the nitrogen in question is substituted by a hydrogen atom, a linear or branched $(C_1$-$C_6)$alkyl group or a group —C(O)—O-Alk, wherein Alk is a linear or branched $(C_1$-$C_6)$alkyl group, G represents —NR₇—, a 1,2,3,4-tetrahydroisoquinolinylene group optionally substituted by a group T, a 2,3-dihydro-1H-isoindolylene group optionally substituted by a group T, or a piperidinylene group, T represents a hydrogen atom, a linear or branched $(C_1$-$C_6)$alkyl optionally substituted by from one to three halogen atoms, a $(C_1$-$C_4)$alkyl-NR₁R₂ group, or a $(C_1$-$C_4)$alkyl-OR₆ group, X represents a $(C_2$-$C_8)$alkylene group in which from 1 to 3 carbon atoms are optionally replaced by a hetero atom selected from oxygen, sulphur and N—R₅, or by an arylene or heteroarylene group, Y represents —CH₂— or —CO—, R₁ and R₂, independently of one another, represent a hydrogen atom or a linear or branched $(C_1$-$C_6)$alkyl group, or R₁ and R₂, together with the nitrogen atom to which they are attached, form a heterocycloalkyl, R₃ and R₄ are such that:
one of them represents a phenyl group of the following formula:

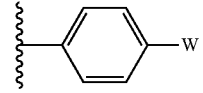

wherein W represents a hydroxy group or a phosphate group selected from —OPO(OM)(OM'), —OPO(OM)(O⁻M₁⁺), —OPO(O⁻M₁⁺)(O⁻M₂⁺), —OPO(O⁻)(O⁻)M₃²⁺, —OPO(OM)(O[CH₂CH₂O]₁CH₃) and —OPO(O⁻M₁⁺)(O[CH₂CH₂O]ₙCH₃), wherein M and M' independently of one another represent a hydrogen atom, a linear or branched $(C_1$-$C_6)$alkyl group, a linear or branched $(C_2$-$C_6)$alkenyl group, a linear or branched $(C_2$-$C_6)$alkynyl group, a cycloalkyl or a heterocycloalkyl, both the cycloalkyl and heterocycloalkyl being composed of from 5 to 6 ring members, $M_1^+$ and $M_2^+$, independently of one another, represent a pharmaceutically acceptable monovalent cation, $M_3^{2+}$ represents a pharmaceutically acceptable divalent cation and n is an integer from 1 to 5, and the other represents an aryl, heteroaryl, heterocycloalkyl, cycloalkyl or linear or branched $(C_1$-$C_6)$ alkyl group, wherein one or more carbon atoms of the preceding groups, or of their possible substituents, are optionally deuterated, R₅ represents a hydrogen atom or a linear or branched $(C_1$-$C_6)$alkyl group, R₆ and R₇, independently of one another, represent a hydrogen atom or a linear or branched $(C_1$-$C_6)$alkyl group, R_a, R_b, R_c and R_d, independently of one another, represent a hydrogen atom, a linear or branched $(C_1$-$C_6)$alkyl group, a halogen atom, a linear or branched $(C_1$-$C_6)$alkoxy group, a hydroxy group, a linear or branched polyhalo-$(C_1$-$C_6)$alkyl group, a trifluoromethoxy group, or the substituents of one of the pairs (R_a,R_b), (R_b,R_c) or (R_c,R_d), together with the carbon atoms to which they are attached, form a ring composed of from 5 to 7 ring members, wherein the ring optionally has from one to 2 hetero atoms selected from oxygen and sulphur, and wherein one or more carbon atoms of the ring defined hereinbefore is optionally deuterated or optionally substituted by from one to 3 groups selected from halogen and linear or branched $(C_1$-$C_6)$alkyl, wherein:
"aryl" means a phenyl, naphthyl, biphenyl or indenyl group,
"heteroaryl" means any mono- or bi-cyclic group composed of from 5 to 10 ring members, having at least one aromatic moiety and having from 1 to 4 hetero atoms selected from oxygen, sulphur, nitrogen and quaternary nitrogen,
"cycloalkyl" means any mono- or bi-cyclic, non-aromatic, carbocyclic group containing from 3 to 10 ring members,
"heterocycloalkyl" means any mono- or bi-cyclic, fused or spiro, non-aromatic group composed of from 3 to 10 ring members, which has from 1 to 3 hetero atoms selected from oxygen, sulphur, SO, $SO_2$ and nitrogen, arylene, heteroarylene, 1,2,3,4-tetrahydroisoquinolinylene, 2,3-dihydro-1H-isoindolylene or piperidinylene mean a divalent aryl, heteroaryl, 1,2,3,4-tetrahydroiso-quinoline or piperidine group, wherein the aryl, heteroaryl, cycloalkyl and heterocycloalkyl groups so defined and the groups alkyl, alkenyl, alkynyl and alkoxy are optionally substituted by from 1 to 3 groups selected from: linear or branched ($C_1$-$C_6$)alkyl optionally substituted by a hydroxy, morpholinyl, 3,3-difluoropiperidinyl or 3,3-difluoropyrrolidinyl group; ($C_3$-$C_6$)spiro; linear or branched ($C_1$-$C_6$)alkoxy optionally substituted by a morpholinyl group; ($C_1$-$C_6$)alkyl-S—; hydroxy; oxo; N-oxide; nitro; cyano; —COOR'; —OCOR'; NR'R"; linear or branched polyhalo-($C_1$-$C_6$)alkyl; trifluoromethoxy; ($C_1$-$C_6$) alkylsulphonyl; halogen; aryl optionally substituted by one or more halogen atoms; heteroaryl; aryloxy; arylthio; cycloalkyl; heterocycloalkyl optionally substituted by one or more halogen atoms or linear or branched ($C_1$-$C_6$)alkyl groups; wherein R' and R", independently of one another, represent a hydrogen atom or a linear or branched ($C_1$-$C_6$) alkyl group optionally substituted by a methoxy group, its enantiomers and diastereoisomers, or addition salts thereof with a pharmaceutically acceptable acid or base.

2. The compound according to claim 1, wherein $A_1$ and $A_2$ each represent a methyl group.

3. The compound according to claim 1, wherein $A_1$ and $A_2$, together with the atoms to which they are attached, form a heterocycle composed of 6 ring members.

4. The compound according to claim 1, wherein $R_a$, $R_c$ and $R_d$ each represent a hydrogen atom and $R_b$ represents a hydrogen or halogen atom.

5. The compound according to claim 1, wherein Y represents —CO—.

6. The compound according to claim 1, wherein G represents a group selected from the following groups:

wherein T represents a methyl group or a (4-morpholinyl) methyl group.

7. The compound according to claim 1, wherein X represents a group selected from the following groups:

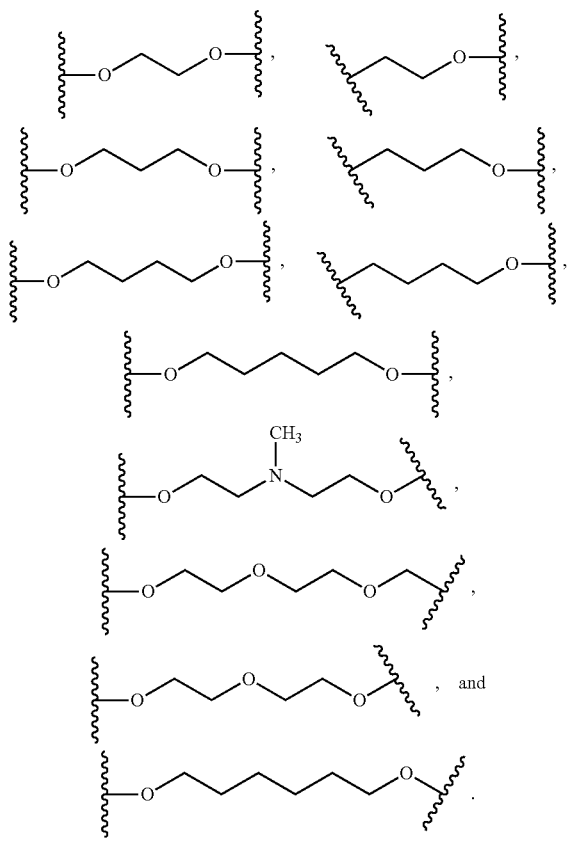

8. The compound according to claim 1, wherein one of the groups $R_3$ or $R_4$ represents a 4-hydroxyphenyl group and the other represents a group selected from the following list:
a phenyl group optionally substituted by a cyano group,
a pyrazolyl group,
a 1-methyl-1H-pyrazolyl group,
a 1-(tetrahydrofuran-3-yl)-1H-pyrazolyl group,
a 5-methyl-2-cyano-1H-pyrrolyl group,
a 1-methyl-2-cyano-1H-pyrrolyl group,
a 1,2-dimethyl-TH-pyrrolyl group,
a 1,5-dimethyl-2-cyano-1H-pyrrolyl group,
a pyrimidinyl group,
an ethyl group, and
a pyridinium group.

9. The compound according to claim 8, wherein $R_4$ represents a 4-hydroxyphenyl group.

10. The compound according to claim 8, wherein $R_3$ represents a 4-hydroxyphenyl group.

11. The compound according to claim 10, wherein $R_3$ represents a 4-hydroxyphenyl group and G represents a piperidinylene group.

12. The compound according to claim 1 is selected from the group consisting of:
6-chloro-14-(4-hydroxyphenyl)-10,11-dimethyl-2,13-dioxo-20,23-dioxa-1,10,14-triazahexacyclo[26.3.1.1~9, 12~.1~15,19.0~3,8~.0~24,29~]tetratriaconta-3,5,7,9 (34),11,15(33),16,18,24,26,28-undecaene-17-carbonitrile,
11-chloro-4-(4-hydroxyphenyl)-1,7,8-trimethyl-4,16,17, 23,24,25-hexahydro-1H,14H-15,18-methano-6,9-(metheno)dibenzo[b,h]pyrazolo[4,3-p][1,6,11,15]oxatriazacycloicosine-5,14(8H)-dione, 6-chloro-14-(4-hydroxyphenyl)-10,11-dimethyl-2,13-dioxo-23-oxa-1,10,14-triazahexacyclo[26.3.1.1~9,12~.1~15,19~.0~3,8~.0~24,29~]tetratriaconta-3,5,7,9(34),11,15(33),16,18,24,26,28-undecaene-17-carbonitrile, 11-chloro-4-(4-hydroxyphenyl)-1,7,8-trimethyl-5,14-dioxo-4,5,8,16,17,23,24,25-octahydro-1H,14H-15,18-methano-6,9-(metheno)dibenzo[b,h]pyrrolo[3,2-p][1,6,11,15]oxatriazacycloicosine-2-carbonitrile, 11-chloro-4-(4-hydroxyphenyl)-1,7,8-trimethyl-5,14-dioxo-1,4,5,8,16,17,23,24-octahydro-14H-15,18-methano-6,9-(metheno)dibenzo[l,r]pyrrolo[2,3-d][1,6,10,15]oxatriazacyclononadecine-2-carbonitrile, 11-chloro-4-(4-hydroxyphenyl)-1,7,8-trimethyl-1,4,16,21,22,23-hexahydro-14H-15,21-methano-6,9-(metheno)dibenzo[j,o]pyrazolo[3,4-b][1,4,8,13]oxatriazacyclononadecine-5,14(8H)-dione, (16S or R)-11-chloro-4-(4-hydroxyphenyl)-1,7,8,16-tetramethyl-5,14-dioxo-4,5,8,16,17,23,24,25-octahydro-1H,14H-15,18-methano-6,9-(metheno)dibenzo[b,h]pyrrolo[3,2-p][1,6,11,15]oxatriazacycloicosine-2-carbonitrile, 4-[16-chloro-3-hydroxy-19,20-dimethyl-13,22-dioxo-6,7,8,9,10,11,19,22-octahydro-13H,23H-8,12-methano-21,18-(metheno)dibenzo[b,j][1,4,8,13]oxatriazacyclononadecin-23-yl]-1,5-dimethyl-1H-pyrrole-2-carbonitrile, 10-fluoro-2-(4-hydroxyphenyl)-5,6-dimethyl-24,27,30-trioxa-2,6,15,32,35-pentaazahexacyclo[29.2.2.1~4,7~.1~15,19~.0~8,13~.0~18,23~]heptatriaconta-1(33),4,7(37),8,10,12,18,20,22,31,34-undecaene-3,14-dione, 10-chloro-2-(4-hydroxyphenyl)-5,6-dimethyl-24,30-dioxa-2,6,15,32,35-pentaazahexacyclo[29.2.2.1~4,7~.1~15,19~.0~8,13~.0~18,23~]heptatriaconta-1(33),4,7(37),8,10,12,18,20,22,31,34-undecaene-3,14-dione, 10-chloro-2-(4-hydroxyphenyl)-5,6,27-trimethyl-24,30-dioxa-2,6,15,27,32,35-hexaazahexacyclo[29.2.2.1~4,7~.1~15,19~.0~8,13~.0~18,23~]heptatriaconta-1(33),4,7(37),8,10,12,18,20,22,31,34-undecaene-3,14-dione, and 11-chloro-4-(4-hydroxyphenyl)-1,7,8-trimethyl-1,4,16,17,23,24-hexahydro-14H-15,18-methano-6,9-(metheno)dibenzo[l,r]pyrazolo[3,4-d][1,6,10,15]oxatriazacyclononadecine-5,14(8H)-dione.

13. A pharmaceutical composition comprising the compound according to claim 1, or an addition salt thereof with a pharmaceutically acceptable acid or base, in combination with one or more pharmaceutically acceptable excipients.

14. A combination of the compound according to claim 1 an anti-cancer agent selected from genotoxic agents, mitotic poisons, anti-metabolites, proteasome inhibitors, kinase inhibitors and antibodies.

15. A pharmaceutical composition comprising the combination according to claim 14 combination with one or more pharmaceutically acceptable excipients.

* * * * *

UNITED STATES PATENT AND TRADEMARK OFFICE
CERTIFICATE OF CORRECTION

| | | |
|---|---|---|
| PATENT NO. | : 11,833,162 B2 | Page 1 of 1 |
| APPLICATION NO. | : 16/757052 | |
| DATED | : December 5, 2023 | |
| INVENTOR(S) | : Jérôme-Benoît Starck et al. | |

It is certified that error appears in the above-identified patent and that said Letters Patent is hereby corrected as shown below:

In the Claims

Claim 1, Column 106, Line 19: "O]$_1$" should read -- O]$_n$ --.

Claim 8, Column 108, Line 44: "TH" should read -- 1H --.

Signed and Sealed this
Twentieth Day of February, 2024

*Katherine Kelly Vidal*

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 18
<212> TYPE: PRT
<213> ORGANISM: Homo sapiens
<220> FEATURE:
<221> NAME/KEY: BINDING
<222> LOCATION: (1)..(18)

<400> SEQUENCE: 1

```
Arg Glu Ile Gly Ala Gln Leu Arg Arg Met Ala Asp Asp Leu Asn Ala
1               5                   10                  15
Gln Tyr
```